(12) United States Patent
Spivey et al.

(10) Patent No.: US 7,857,754 B2
(45) Date of Patent: Dec. 28, 2010

(54) APPARATUS USEFUL FOR POSITIONING A DEVICE ON AN ENDOSCOPE

(75) Inventors: James T. Spivey, Loveland, OH (US); David Stefanchik, Morrow, OH (US); Omar J. Vakharia, Mason, OH (US); Rick D. Applegate, Florence, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 879 days.

(21) Appl. No.: 11/128,704

(22) Filed: May 13, 2005

(65) Prior Publication Data

US 2006/0258902 A1    Nov. 16, 2006

(51) Int. Cl.
*A61B 1/00* (2006.01)

(52) U.S. Cl. .................. 600/127; 600/104; 600/101; 606/1

(58) Field of Classification Search ............... 600/104, 600/116, 127, 115, 124, 125, 106, 121; 606/1; 128/898; 81/3.29; 49/360, 404
See application file for complete search history.

(56) References Cited

U.S. PATENT DOCUMENTS

| | | | |
|---|---|---|---|
| 3,662,451 A * | 5/1972 | Wagner | 29/237 |
| 3,858,577 A | 1/1975 | Bass et al. | |
| 3,915,157 A | 10/1975 | Mitsui | |
| 4,436,087 A | 3/1984 | Ouchi | |
| 4,580,551 A | 4/1986 | Siegmund et al. | |
| 4,646,722 A | 3/1987 | Silverstein | |
| 4,686,965 A | 8/1987 | Bonnet et al. | |
| 4,721,097 A | 1/1988 | Arnello | |
| 4,773,394 A | 9/1988 | Reichstein et al. | |
| 4,794,911 A | 1/1989 | Okada | |
| 4,947,827 A | 8/1990 | Opie et al. | |
| 5,025,778 A | 6/1991 | Silverstein et al. | |
| 5,026,377 A | 6/1991 | Burton et al. | |
| 5,217,001 A | 6/1993 | Nakao et al. | |
| 5,237,984 A | 8/1993 | Williams et al. | |
| 5,257,617 A | 11/1993 | Takahashi | |
| 5,347,995 A | 9/1994 | Slater et al. | |

(Continued)

FOREIGN PATENT DOCUMENTS

EP    1284120 A1    2/2003

(Continued)

OTHER PUBLICATIONS

Iruru Maetani, M.D. et al., "Efficacy of an Overtube for Reducing Risk of Peristomal Infection after PEG Placement: a Prospective Randomized Comparison Study", Gastrointestinal Endoscopy, vol. 61, No. 4, 2005.

(Continued)

*Primary Examiner*—John P Leubecker
*Assistant Examiner*—Victoria W Chen

(57) ABSTRACT

A medical apparatus and method useful for positioning a device, such as an endcap, on an end of an endoscope, is disclosed. The apparatus can exert a pulling force on the endoscope through the endcap while a pushing force is applied to the endcap. The apparatus can be used to press an endcap onto the distal end of an endoscope without grasping by hand a sheath in those applications where the endoscope is disposed in a sheath.

3 Claims, 48 Drawing Sheets

U.S. PATENT DOCUMENTS

| | | | |
|---|---|---|---|
| 5,363,843 A | 11/1994 | Daneshvar | |
| 5,390,663 A | 2/1995 | Schaefer | |
| 5,411,022 A | 5/1995 | McCue et al. | |
| 5,458,132 A | 10/1995 | Yabe et al. | |
| 5,465,857 A * | 11/1995 | Yang | 215/228 |
| 5,476,899 A | 12/1995 | Funaki et al. | |
| 5,489,256 A | 2/1996 | Adair | |
| 5,503,616 A | 4/1996 | Jones | |
| 5,505,686 A | 4/1996 | Willis et al. | |
| 5,607,386 A | 3/1997 | Flam | |
| 5,630,730 A | 5/1997 | Wang et al. | |
| 5,630,782 A | 5/1997 | Adair | |
| 5,643,175 A | 7/1997 | Adair | |
| 5,645,519 A | 7/1997 | Lee et al. | |
| 5,665,064 A | 9/1997 | Bodicky et al. | |
| 5,690,620 A | 11/1997 | Knott | |
| 5,695,449 A | 12/1997 | Moriyama | |
| 5,725,477 A * | 3/1998 | Yasui et al. | 600/127 |
| 5,733,241 A | 3/1998 | King | |
| 5,746,694 A | 5/1998 | Wilk et al. | |
| 5,746,695 A * | 5/1998 | Yasui et al. | 600/127 |
| 5,749,889 A | 5/1998 | Bacich et al. | |
| 5,820,546 A | 10/1998 | Ouchi | |
| 5,868,662 A * | 2/1999 | Borodulin et al. | 600/116 |
| 5,882,293 A | 3/1999 | Ouchi | |
| 5,895,373 A | 4/1999 | Hirsch et al. | |
| 5,916,145 A | 6/1999 | Chu et al. | |
| 5,944,654 A | 8/1999 | Crawford | |
| 5,989,183 A | 11/1999 | Reisdorf et al. | |
| 6,053,934 A * | 4/2000 | Andrews et al. | 600/104 |
| 6,059,719 A | 5/2000 | Yamamoto et al. | |
| 6,071,233 A | 6/2000 | Ishikawa et al. | |
| 6,120,483 A | 9/2000 | Davey et al. | |
| 6,146,389 A | 11/2000 | Geitz | |
| 6,179,776 B1 | 1/2001 | Adams et al. | |
| 6,238,389 B1 | 5/2001 | Paddock | |
| 6,241,702 B1 | 6/2001 | Lundquist | |
| 6,293,909 B1 | 9/2001 | Chu et al. | |
| 6,309,346 B1 | 10/2001 | Farhadi | |
| 6,322,495 B1 | 11/2001 | Snow et al. | |
| 6,352,503 B1 | 3/2002 | Matsui et al. | |
| 6,355,034 B2 | 3/2002 | Cosmescu | |
| 6,359,379 B1 | 3/2002 | Lee et al. | |
| 6,527,753 B2 | 3/2003 | Sekine et al. | |
| 6,530,881 B1 | 3/2003 | Ailinger et al. | |
| 6,569,085 B2 | 5/2003 | Kortenbach et al. | |
| 6,638,587 B1 | 10/2003 | Wang et al. | |
| 6,689,130 B2 | 2/2004 | Aral et al. | |
| 6,699,180 B2 | 3/2004 | Kobayashi | |
| 6,740,030 B2 | 5/2004 | Martone et al. | |
| 6,761,685 B2 | 7/2004 | Adams et al. | |
| 6,878,106 B1 | 4/2005 | Hermann | |
| 6,878,108 B2 | 4/2005 | Ouchi | |
| 6,921,361 B2 | 7/2005 | Suzuki et al. | |
| 6,997,931 B2 | 2/2006 | Sauer et al. | |
| 7,081,097 B2 | 7/2006 | Martone et al. | |
| 2001/0044595 A1 | 11/2001 | Reydel et al. | |
| 2002/0014385 A1 | 2/2002 | Grosspietsch et al. | |
| 2002/0062063 A1 * | 5/2002 | Ogura et al. | 600/148 |
| 2002/0077593 A1 * | 6/2002 | Perkins et al. | 600/116 |
| 2002/0091304 A1 * | 7/2002 | Ogura et al. | 600/141 |
| 2002/0107530 A1 | 8/2002 | Sauer et al. | |
| 2002/0111534 A1 | 8/2002 | Suzuki et al. | |
| 2002/0147385 A1 | 10/2002 | Butler et al. | |
| 2002/0183591 A1 | 12/2002 | Matsuura et al. | |
| 2003/0009152 A1 | 1/2003 | O'Hara et al. | |
| 2003/0083548 A1 * | 5/2003 | Ouchi et al. | 600/121 |
| 2003/0130564 A1 | 7/2003 | Martone et al. | |
| 2003/0163025 A1 | 8/2003 | Kaji | |
| 2003/0171651 A1 | 9/2003 | Page et al. | |
| 2003/0176880 A1 * | 9/2003 | Long et al. | 600/104 |
| 2003/0191365 A1 | 10/2003 | Kobayashi | |
| 2003/0225393 A1 | 12/2003 | McMichael et al. | |
| 2004/0077927 A1 * | 4/2004 | Ouchi | 600/123 |
| 2004/0215058 A1 | 10/2004 | Zirps et al. | |
| 2004/0230095 A1 | 11/2004 | Stefanchik et al. | |
| 2004/0230096 A1 | 11/2004 | Stefanchik et al. | |
| 2004/0230097 A1 | 11/2004 | Stefanchik et al. | |
| 2005/0143625 A1 | 6/2005 | Whitmore et al. | |
| 2005/0171468 A1 | 8/2005 | Wood | |
| 2005/0256374 A1 | 11/2005 | Long et al. | |
| 2005/0256455 A1 | 11/2005 | Weststrate et al. | |
| 2006/0173422 A1 | 8/2006 | Reydel et al. | |
| 2007/0173687 A1 | 7/2007 | Shima et al. | |
| 2007/0249908 A1 | 10/2007 | Lu et al. | |

FOREIGN PATENT DOCUMENTS

| | | |
|---|---|---|
| EP | 1477105 | 11/2004 |
| WO | 91/14391 A2 | 10/1991 |
| WO | 97/29680 A2 | 8/1997 |
| WO | 00/48506 | 2/2000 |
| WO | 01/49165 A1 | 1/2001 |
| WO | 2004/021867 A2 | 3/2004 |

OTHER PUBLICATIONS

EPO Search Report dated Aug. 18, 2004 for corresponding European Patent Application No. EP04252842.2.

EPO Search Report dated Aug. 10, 2006 for corresponding European Patent Application No. EP06252511.8.

EPO Search Report dated Aug. 14, 2006 for corresponding European Patent Application No. EP06252513.4.

EPO Search Report dated Aug. 15, 2006 for corresponding European Patent Application No. EP06252515.9.

EPO Search Report dated Aug. 16, 2006 for corresponding European Patent Application No. EP06252514.2.

EPO Search Report dated Oct. 11, 2006 for corresponding European Patent Application No. EP06252498.8.

EPO Search Report dated Oct. 24, 2006 for corresponding European Patent Application No. EP06252507.6.

* cited by examiner

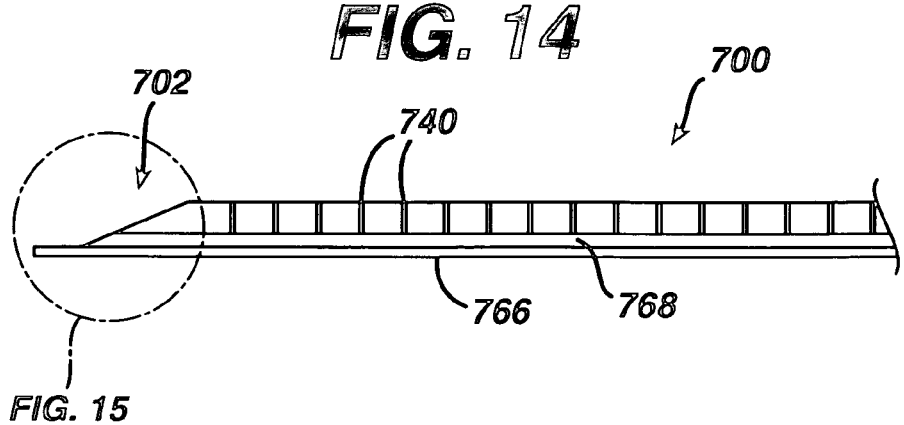
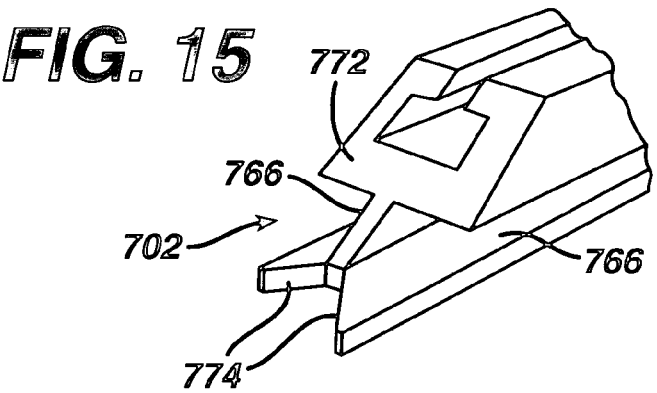
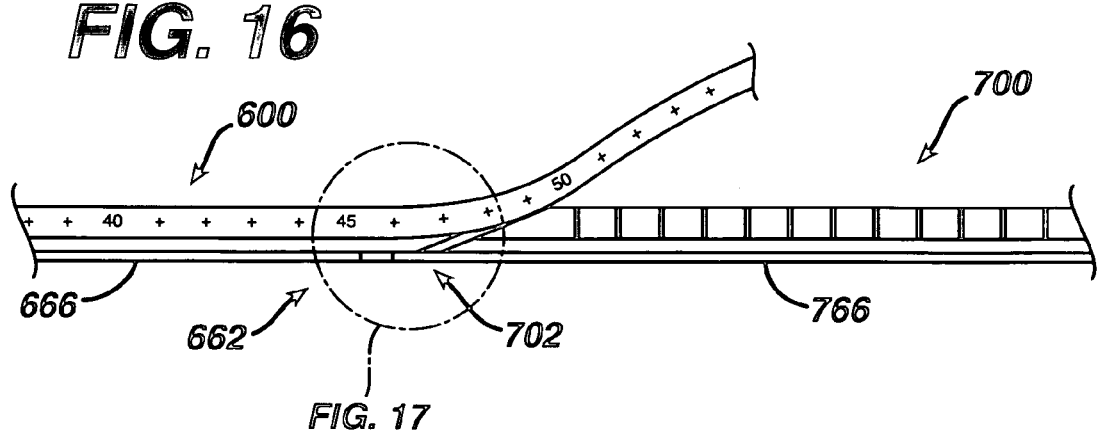
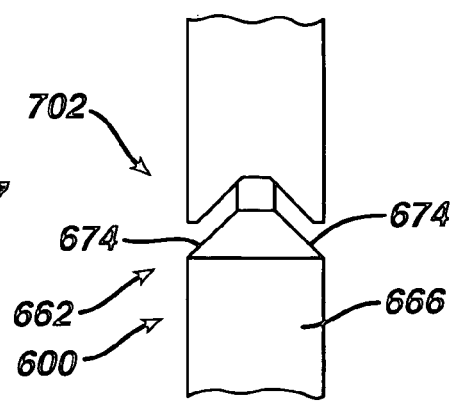

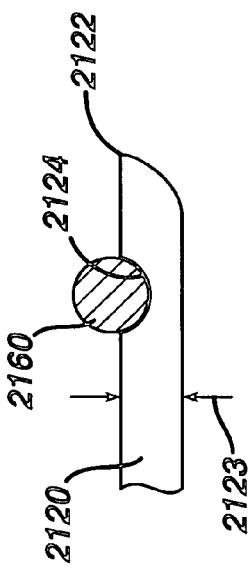
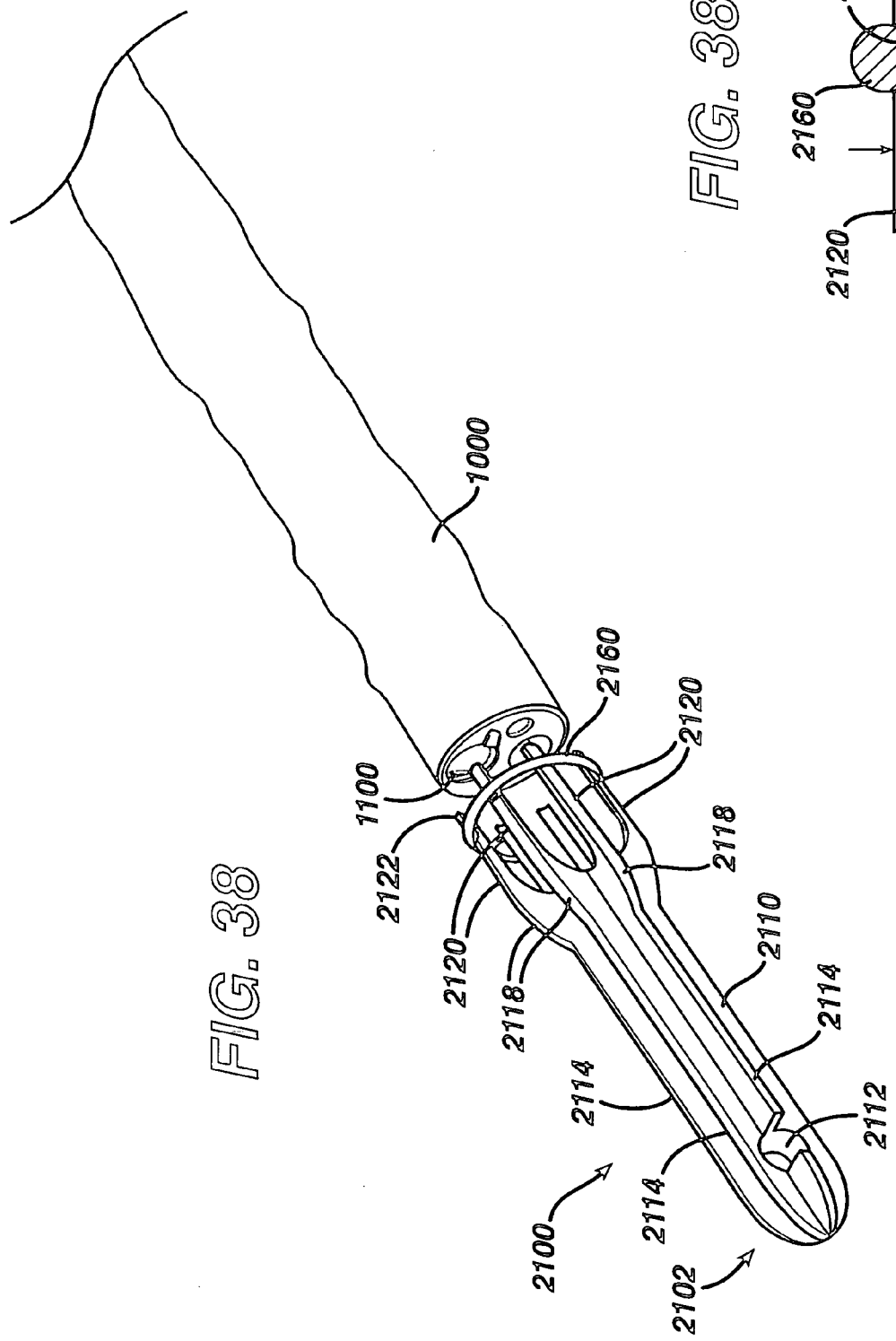

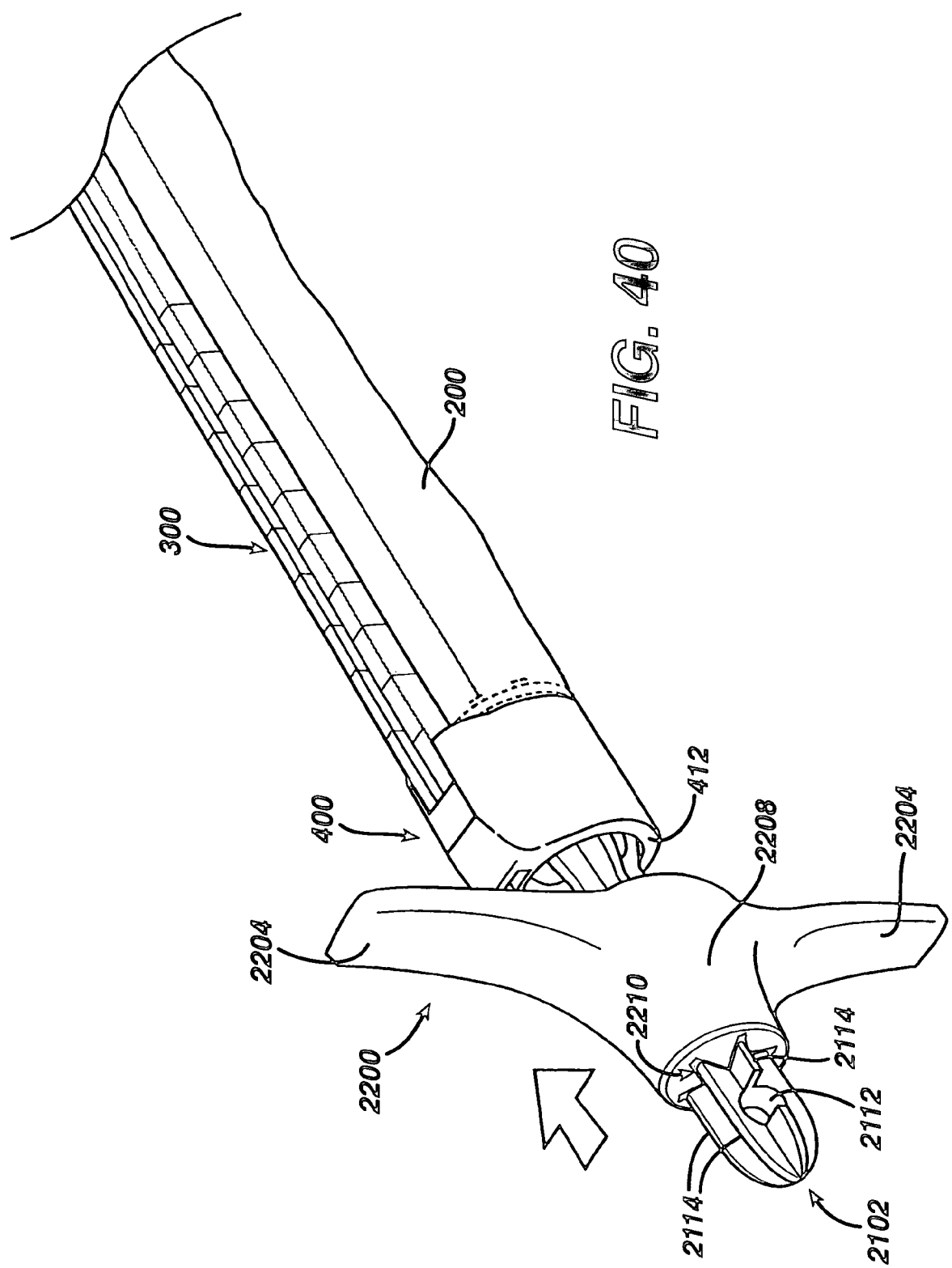

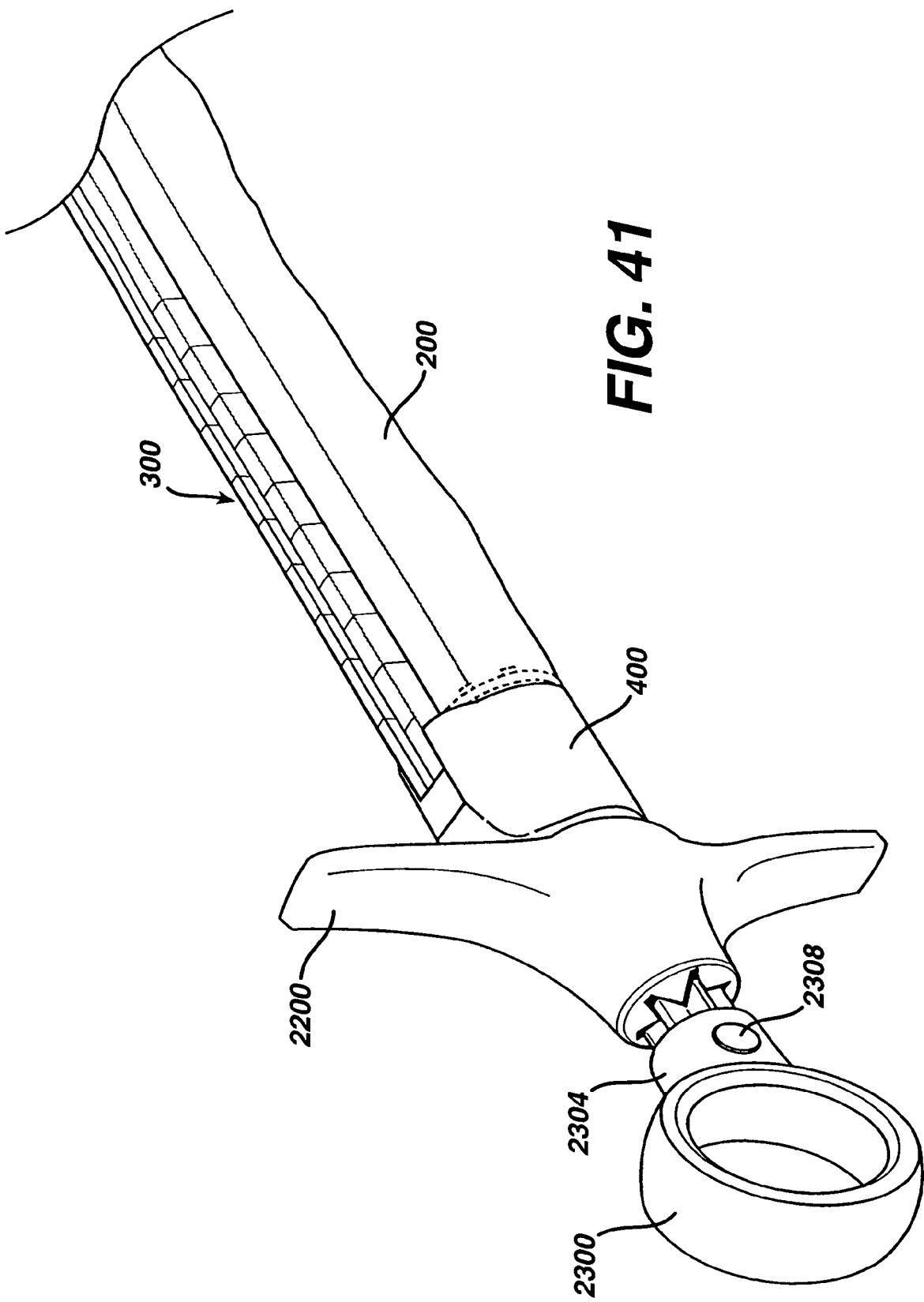

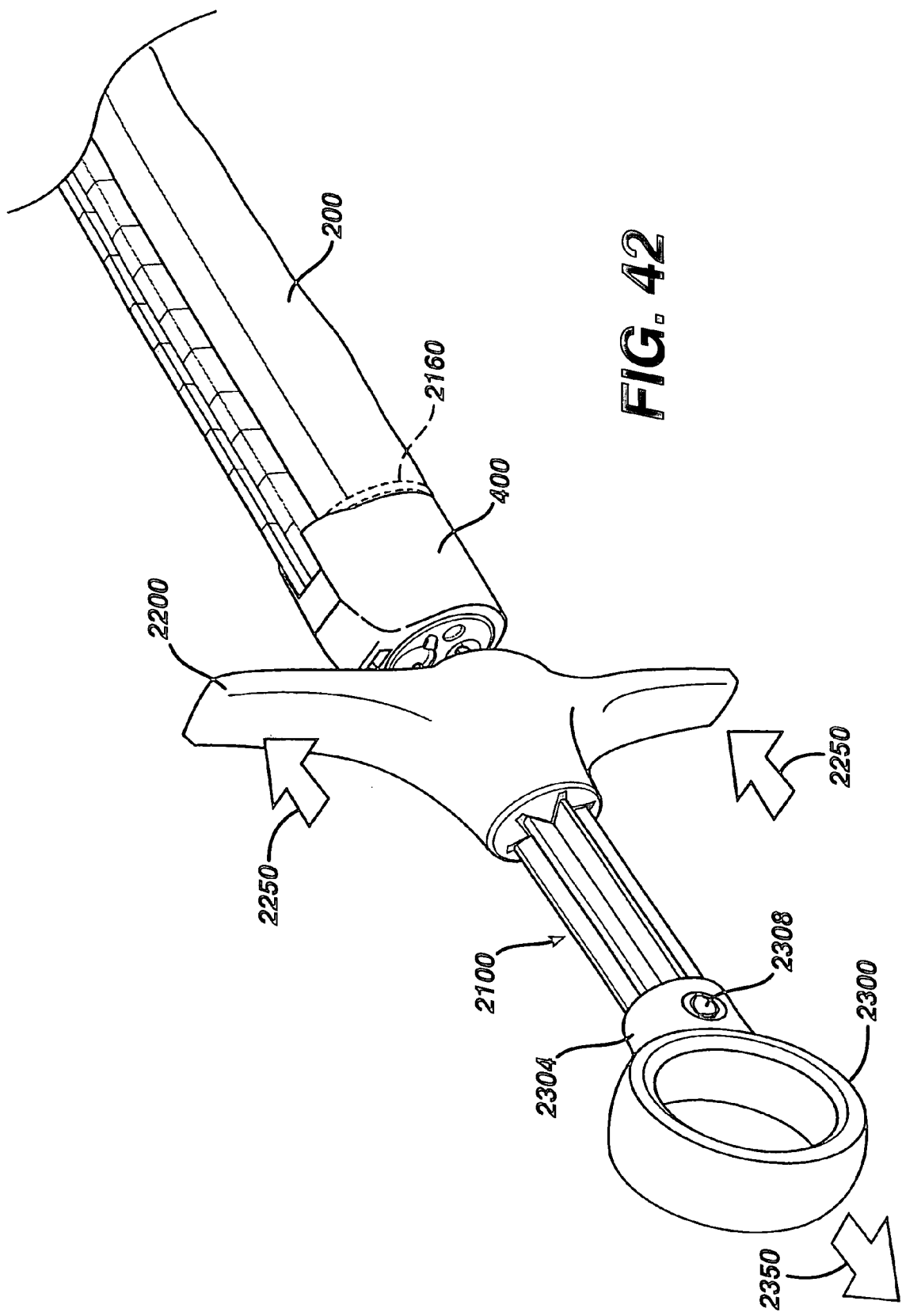

APPARATUS USEFUL FOR POSITIONING A DEVICE ON AN ENDOSCOPE

CROSS REFERENCE TO RELATED APPLICATIONS

This application claims priority to the following patent applications, which are hereby incorporated by reference: U.S. Ser. No. 10/440,957 (published as US 2004/0230095); 10/440,660 (published as US 2004/0230096); and U.S. Ser. No. 10/440,956 (published US 2004/0230097); each filed May 16, 2003.

This application claims priority to and incorporates by reference U.S. patent application "Medical Instrument Having a Guidewire and an Add-to Catheter", filed May 12, 2005 in the name of Long et al. having a Ser. No. 11/128,108.

FIELD OF THE INVENTION

The present invention is related generally to medical devices and more particularly to devices and methods useful in endoscopic procedures.

BACKGROUND OF THE INVENTION

Minimally invasive procedures are desirable because such procedures can reduce pain and provide relatively quick recovery times as compared with conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall.

Still less invasive treatments include those that are performed through insertion of an endoscope through a natural body orifice to a treatment site. Examples of this approach include, but are not limited to, cystoscopy, hysteroscopy, esophagogastroduodenoscopy, and colonoscopy. Many of these procedures employ the use of a flexible endoscope during the procedure. Flexible endoscopes often have a flexible, steerable articulating section near the distal end that can be controlled by the user by utilizing controls at the proximal end.

Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 to 3.5 mm for the purpose of introducing and removing medical devices and other accessory devices to perform diagnosis or therapy within the patient. As a result, the accessory devices used by a physician can be limited in size by the diameter of the accessory channel of the scope used. Additionally, the physician may be limited to a single accessory device when using the standard endoscope having one working channel.

Certain specialized endoscopes are available, such as large working channel endoscopes having a working channel of 5 mm in diameter, which can be used to pass relatively large accessories, or to provide capability to suction large blood clots. Other specialized endoscopes include those having two working channels. One disadvantage of such large diameter/ multiple working channel endoscopes can be that such devices can be relatively expensive. Further, such large diameter/multiple working channel endoscopes can have an outer diameter that makes the endoscope relatively stiff, or otherwise difficult to intubate.

Various references describe methods or systems related to an endoscope, such as for example: U.S. Pat. No. 5,025,778, Silverstein; U.S. Pat. No. 4,947,827, Opie; US 2002/107530 published Aug. 8, 2002 in the name of Sauer; U.S. Pat. No. 6,352,503, Matsui. One disadvantage of known systems is the potential for the distal end of a device used externally of an endoscope to move, which may cause the accessory to lack precision or the ability to be maintained within a desired field of view of the imaging capability of the endoscope.

WO 00/48506 published Aug. 24, 2000 in the name of Herrmann discloses a deformable endoscope with at least one supplementary device. The unit comprising the endoscope and the supplementary device is said to have a non-round cross-section. Such a non-circular endoscope may be disadvantageous from the point of view of cost, complexity, or ease in cleaning/sterilization. For instance, a standard endoscope with a smooth, substantially-circular cross section can be relatively easy to sanitize and clean.

WO 00/48506 published Aug. 24, 2000 in the name of Kortenbach, discloses methods and devices for delivering a medical instrument over the exterior of an endoscope to allow the use of instruments too large to fit through the lumena of the endoscope. Kortenbach discloses a collar for use with an endoscope, resilient straps, a flexible sheath having a reclosable seam, flexible polymer extrusions, and a floppy tangential sheath defining a lumen having an irregular (collapsible) cross section. Kortenbach also discloses a track with an inverted T configuration.

Endoscopes may also be used with feeding tubes. For instance, it is known to advance a feeding tube through an internal channel of an endoscope. It is also known to advance a feeding tube together with an endscope, such as by holding the distal end of the feeding tube with a pair of forceps extending from a distal end of the endoscope, and "dragging" the feeding tube along the outside of the endoscope while advancing the endoscope to a desired location.

Still, scientists and engineers continue to seek improved devices and methods for the introducing medical devices into the gastro-intestinal tract, including improved devices and methods for placing feeding tubes in patients.

SUMMARY OF THE INVENTION

The present invention provides methods and devices useful with various medical procedures, including without limitation methods and devices useful with endoscopes, methods and devices employed through naturally occurring body orifices, and methods and devices related to placement of feeding tubes. For instance, in one embodiment, the present invention can be used to quickly and consistently place an accessory, such as a feeding tube, in a desired location, such as in the stomach or the jejunum, and such that the device stays in the desired position during removal of the endoscope. In certain embodiments, the present invention can be employed to reduce the number of intubations needed for certain procedures, such as the number of intubations needed to place a feeding tube. In certain embodiments, the present invention can also be employed to reduce the number of steps required in certain medical procedures, such as by reducing the oral to nasal transfer steps in feeding tube installation, reducing the number of times tools or devices are switched or deployed in the body, reducing the number of hands required to perform a procedure, and/or reducing the number of times the medical professional must change hand position during a procedure.

In one embodiment, the present invention provides an apparatus for positioning a device, such as an endcap, on an end of an endoscope. The apparatus can include a first component for applying a force to the endcap; and a second component operatively associated with the first component and movable with respect to the first component. The second component can apply a force to the endoscope through an opening in the device. In one embodiment, the first component applies a pushing force on a distal face of the endcap, simultaneously with the second component applying a pulling force to the endoscope. In one embodiment, the apparatus includes a component that can be selectively expandable within a working channel of the endoscope to provide a pulling force on the endoscope. In another embodiment, the apparatus includes a loading element (which can be disposable and formed of a lightweight polymeric material) which has a first end sized to pass through the endcap, and a second end adapted to releasably engage the distal end of the endoscope. The loading element can have a plurality of resilient prongs for releasably engaging the distal end of the endoscope.

In certain embodiments, the invention can be employed with respect to procedures involving Percutaneous Endoscopic Gastrostomy (PEG) tubes and/or Jejunal Enteral Tube through a Percutaneous Endoscopic Gastrostomy (JET PEG) procedures.

BRIEF DESCRIPTION OF THE FIGURES

FIG. 14 is a schematic illustration of a distal portion of a member which may be employed to maintain the feeding tube in a desired position during removal of the endoscope and the carrier from the patient's GI tract.

FIG. 15 is a schematic illustration of the distal end of the member of FIG. 14 and showing contact surfaces positioned, sized, and/or shaped for engaging contact surfaces on the proximal end of a rail feature associated with a feeding tube.

FIG. 16 is a schematic illustration of the distal portion of the member of FIG. 14 positioned with respect to the proximal end of the rail feature on the feeding tube.

FIG. 17 is a schematic bottom view illustration of adjacent portions of the rail feature on the feeding tube and the member of FIG. 14.

FIG. 38 illustrates an endcap loading element which can be used to an endcap on the distal end of an endoscope.

FIG. 38A is a cross-sectional schematic illustration of a flexible prong of the endcap loading element.

FIG. 40 illustrates a handle sliding proximally on the endcap loading element to be positioned against the distal face of the endcap.

FIG. 41 illustrates a ring which can be attached to a distal portion of the endcap loading element.

FIG. 42 illustrates pulling distally on the ring while pushing proximally on the handle, to provide a pushing force on the distal face of the endcap with the handle, while providing a pulling traction force on the outer surface of the endoscope with the flexible prongs, such that the end cap and the O-ring slide off of the endcap loading element and onto the distal end of the endoscope.

DETAILED DESCRIPTION OF THE INVENTION

Figure 1:
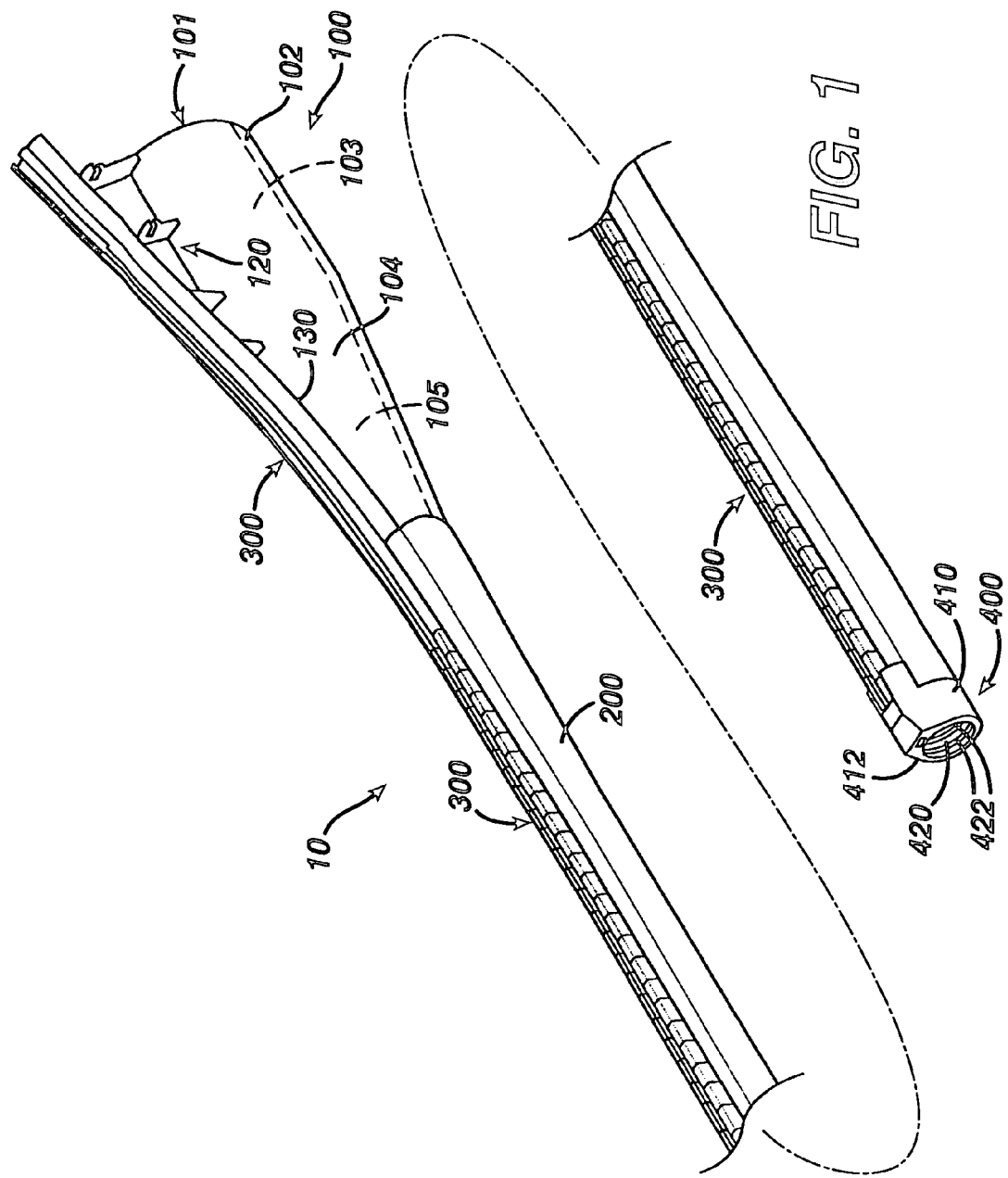
FIG. 1 is a schematic illustration of an endoscopic sheath and track.
Figure 2:
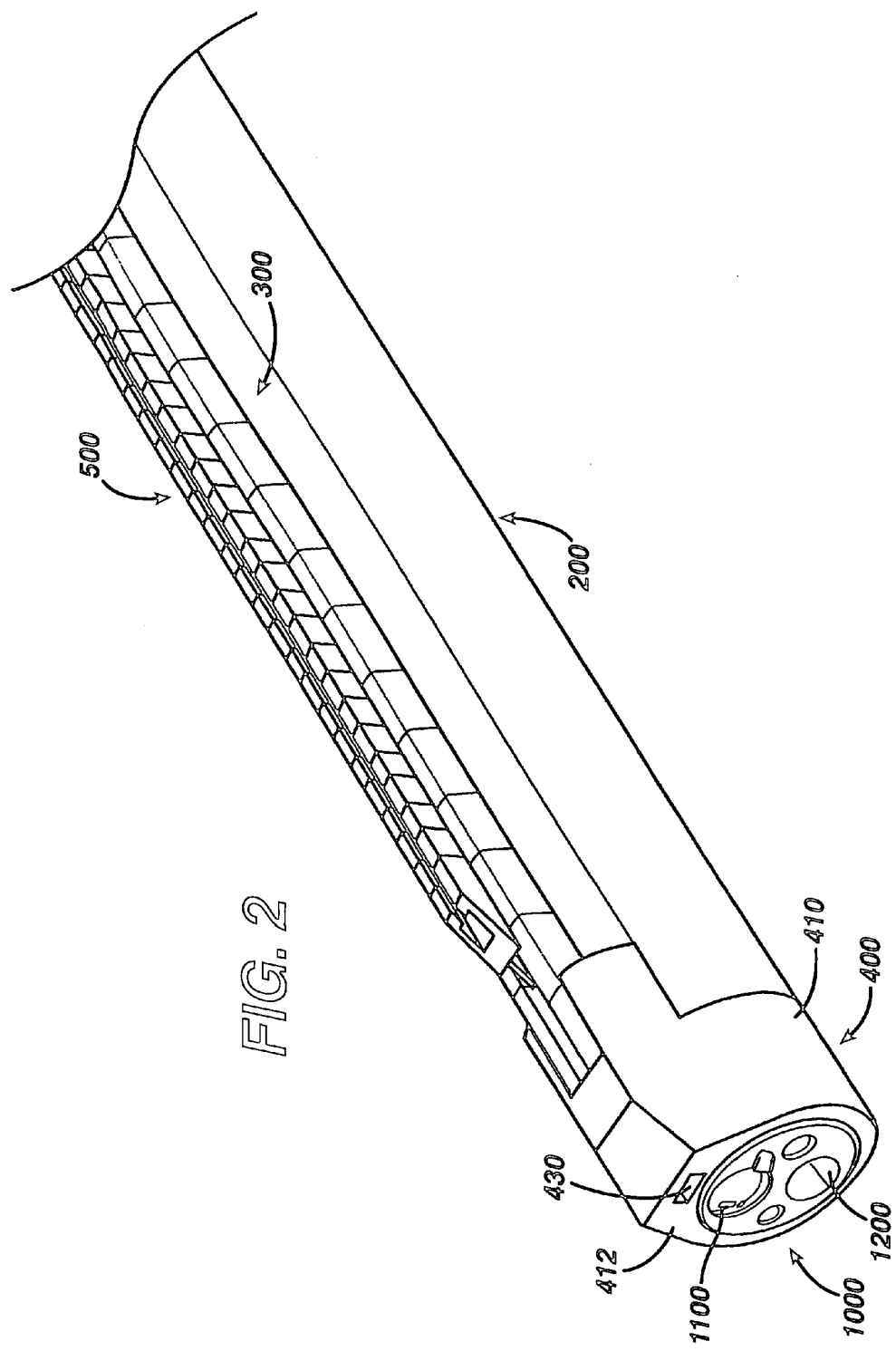
FIG. 2 is a schematic illustration of the distal end of the sheath of FIG. 1 showing a carrier being advanced on the track.

FIGS. 1 and 2 illustrate a medical apparatus 10 according to one embodiment of the present invention. In one embodiment, apparatus 10 can include a handle 100, a flexible catheter or sheath 200 extending from handle 100, a flexible track 300 disposed on the sheath 200, and an endcap 400 disposed at the distal end of sheath 200. Handle 100 and flexible sheath 200 can each be sized to receive an endoscope therethrough.

Apparatus 10 can also include a carrier 500 which is adapted to slidably engage track 300, as shown in FIG. 2. Endcap 400 can be sized and shaped to engage the distal end of an endoscope, such as an endoscope 1000 as shown in FIG. 2. Endoscope 1000 can be any commercially available endoscope, such as a gastroscope or colonoscope having an articulating distal section, and including a viewing element 1100 and a working channel 1200. Any suitable endoscope, including without limitation gastroscopes and pediatric colonscopes can be used with the present invention. Suitable endoscopes for use with the present invention include, without limitation, model PCF100, PCF130L, PCF140L, or PCF160AL endoscopes manufactured by Olympus Corporation of Japan. The handle 100, sheath 200, and endcap 400 can be sized to receive various diameter endoscopes, such as, but not limited to, endoscopes having a diameter from about 9 mm to about 14 mm.

To introduce the endoscope 1000 with the apparatus 10 into a patient, the operator may start with a clean dry endoscope. The sheath 200 is preferably formed of a thin, light weight, drapable polymeric film material which can be relatively soft and elastically extensible, and which has substantially no torsional stiffness and no torsional load carrying capability. By "drapable" it is meant that the sheath does not maintain a circular or other regular cross-sectional shape in the absence of an internal structure (such as an endoscope) supporting the sheath.

In one embodiment, the sheath 200 can be formed of a material having an elastic modulus of less than about 20 ksi, more particularly less than about 15 ksi, still more particularly less than about 10 ksi, and even more particularly less than about 7 ksi. The sheath can be formed of a material having a yield strength of less than about 500 psi, more particularly less than about 300 psi, still more particularly less than about 200 psi, and still more particularly less than about 125 psi. In one embodiment, the sheath can be formed of a material having a yield strength of between about 90 psi and about 120 psi. The elastic modulus and yield strength can be determined as an average of five or more measurements, and can be determined using ASTM test #D882 (Standard Test Methods for Tensile Properties of Thin Plastic Sheeting) using a gage length of 4.0 inch, a gage width of 1.0 inch, a test thickness equal to the thickness of the film (e.g about 0.005 inch), and a test machine speed of 0.4 in/minute. In one embodiment, the sheath can be formed of a film have a modulus of less than about 7 ksi, a yield strength of less than about 125 psi, and a tensile strength at break (measured according to ASTM D 638) of at least about 1 M Pa (mega Pascal), more particularly at least about 5 Mpa, and still more particularly about 10 Mpa or greater. The sheath can be formed of a film having a tensile elongation (measured using ASTM D 638) of at least about 200 percent, more particularly at least about 500 percent, and still more particularly about 800 percent or more. The modulus, yield strength, tensile strength, and elongation are determined as mean of at least five measurements.

In some embodiments, it can be desirable that the sheath 200 can be inserted over the insertion length of the scope without use of a lubricant. In one embodiment, the sheath 200 can have a non-smooth, textured inner surface 210 that prevents the inner surface of the flexible sheath from "sticking" to outer surface of the insertion portion of the endoscope. The textured inner surface can also aid in gripping the endoscope through the sheath 200, such as for example if it is desired to rotate the sheath and endoscope together. The inner surface can be textured and the outer surface can be generally smooth, or both the inner and outer surfaces may be textured. The inner surface of the sheath 200 may have the same texture as the outside surface, be relatively more textured than the outer surface, or be relatively less textured than the outside surface.

The textured inner surface can be provided with elevated portions, depressed portions, or combinations of elevated and depressed portions. For instance, the inner surface can include randomly spaced bumps or protrusions, or alternatively, can be provided by raised portions (such as bumps, ribs or protrusions) that occur at regularly spaced intervals, which intervals may be of generally uniform spacing. The texture of the inner surface can be measured in terms of a roughness average measurement, where "roughness average" or "Ra" is the arithmetic average of the absolute values of the measured profile height deviations divided by an evaluation length, as set forth on page 728 of the 27$^{st}$ edition of Machinery's Handbook, 2004, incorporated herein by reference. The roughness average can be measured using optical interferometry with a Zygo NewView 100 3D Imaging Surface Structure Analyzer marketed by Zygo Corporation of Middlefield, Conn. The following measurement parameters and analysis parameters can be used:

Measurement Parameters: Acquisition Mode is "Scan"; Camera Mode is 320×240 Normal; Phase Controls (AGC is "ON"; Phase res is "High"; Min Mod is 1%; Min Area size is 7; Discon Action is "Filter"; Connection Order is "Location"; Remove Fringes is "Off"; Image Zoom is 1×); Scan Controls (Scan length is "Extended"; Extended Scan Length is 11000 micro inches; FDA Res is "Low").

Analysis Parameters: Filter is "Lowpass"; Filter Type is "Average"; Filter Window Size is 13; Filter High Freq. 1/mil; Filter Low Freq. 1/mil; Filter Trim is "Off"; Remove is "Plane"; Trim is 0; Remove Spikes is "ON"; Spike Height (xRMS) is 1.25; Data Fill is "ON"; Data Fill Max is 25. The measurements can be made with a 5× Michelson Objective Lens, and the samples can be coated with gold or otherwise coated to provide an generally opaque surface that reflects light. Gold coating can be applied with a Hummer 6.2 Sputtering System.

In one embodiment, the inner surface of the sheath 200 can a have a roughness average value Ra of less than about 500 micro inch (0.000500 inch), more particularly less than about 400 micro inch, still more particularly less than about 250 micro inch, and still more particularly less than about 150 micro inch. In one embodiment, the roughness average value of the inner surface can be between about 50 and about 500 micro inch, more particularly between about 50 and about 250 micro inch, and still more particularly between about 75 and about 125 micro inch. The roughness average value is determined as a mean of at least five measurements.

The inner surface of the sheath 200 can have a coefficient of friction which is suitable for gripping the endoscope with the sheath 200, but which also allows the endoscope to be positioned within the sheath without excessive effort. A suitable inner surface can have a coefficient of static friction and a coefficient of sliding friction which can both be less than about 1.0. In one embodiment, the coefficient of static friction can be between about 0.3 and about 0.6 (more particularly between about 0.4 and 0.5) and the coefficient of sliding friction can be between about 0.3 and about 0.6 (more particularly between about 0.4 and about 0.5) using a friction sled formed of Ultem 1000 material. The coefficient of static friction can be between about 0.2 and about 0.5 (more particularly between about 0.3 and about 0.4) and the coefficient of sliding friction can be between about 0.2 and about 0.5 (more particularly between about 0.3 and about 0.4) using a friction test sled formed of 440C stainless steel. The coefficient of static and sliding friction can be measured using ASTM test #D1894 (Standard Test Method for Static and Kinetic Coefficients of Friction of Plastic Film and Sheeting). The coefficient of friction is determined as a mean of at least five measurements.

In one embodiment, the sheath 200 can be formed of a thermoplastic polyolefin film having a thickness of less than about 0.010 inch, and can comprise polypropylene, polyethylene, and mixtures thereof. In one embodiment the sheath can be formed of a film having a thickness of between about 0.004 to 0.006 inch, more particularly about 0.005 inch. One suitable film is available as Basell Softell Q020F made by Basell Nev., Hoofdorp, Netherlands, such as can be provided by Specialty Extrusion, Inc. of Royersford, Pa.

The handle 100 can be formed of any suitable material, including without limitation relatively rigid biocompatible metals and plastics. One suitable material from which handle 100 can be formed is molded polypropylene, such as is available as Huntsman 12N25ACS296 from Huntsman Corp. of Houston Tex.

As shown in FIG. 1, handle 100 can have a generally cylindrical proximal section 102 having a proximal opening for receiving an endoscope, and an adjacent distally converging conical section 104. The handle 100 includes an opening 101 at it's proximal end for receiving an endoscope. The handle's internal channel for receiving the endoscope can include a generally cylindrical channel section 103 (shown in phantom) corresponding to section 102, and a generally conical channel section 105 (shown in phantom) corresponding to section 104. The generally conical channel section 105 can taper from a relatively larger inner diameter to a relatively small inner diameter as the channel section 105 extends distally. A track support structure 120 is shown extending from sections 102 and 104 to support a track ramp 130 at an inclined angle with respect to the longitudinal axis of sections 102 and 104. Track ramp 130 can support the proximal portion of the track 300.

Figure 1A:
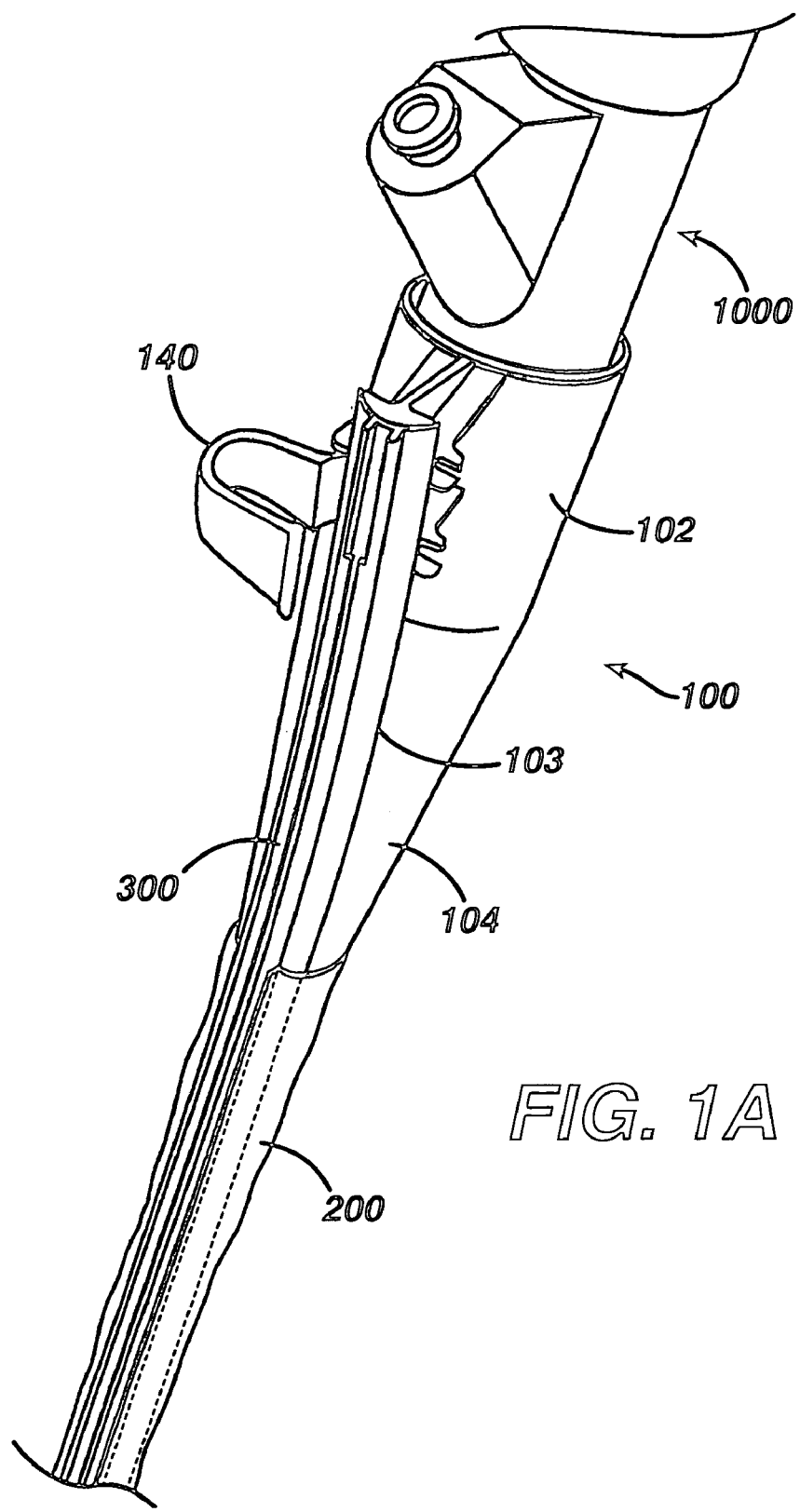
FIG. 1A is a schematic illustration of an endoscope inserted into a handle having a hinged latch in an open configuration.
Figure 1B:
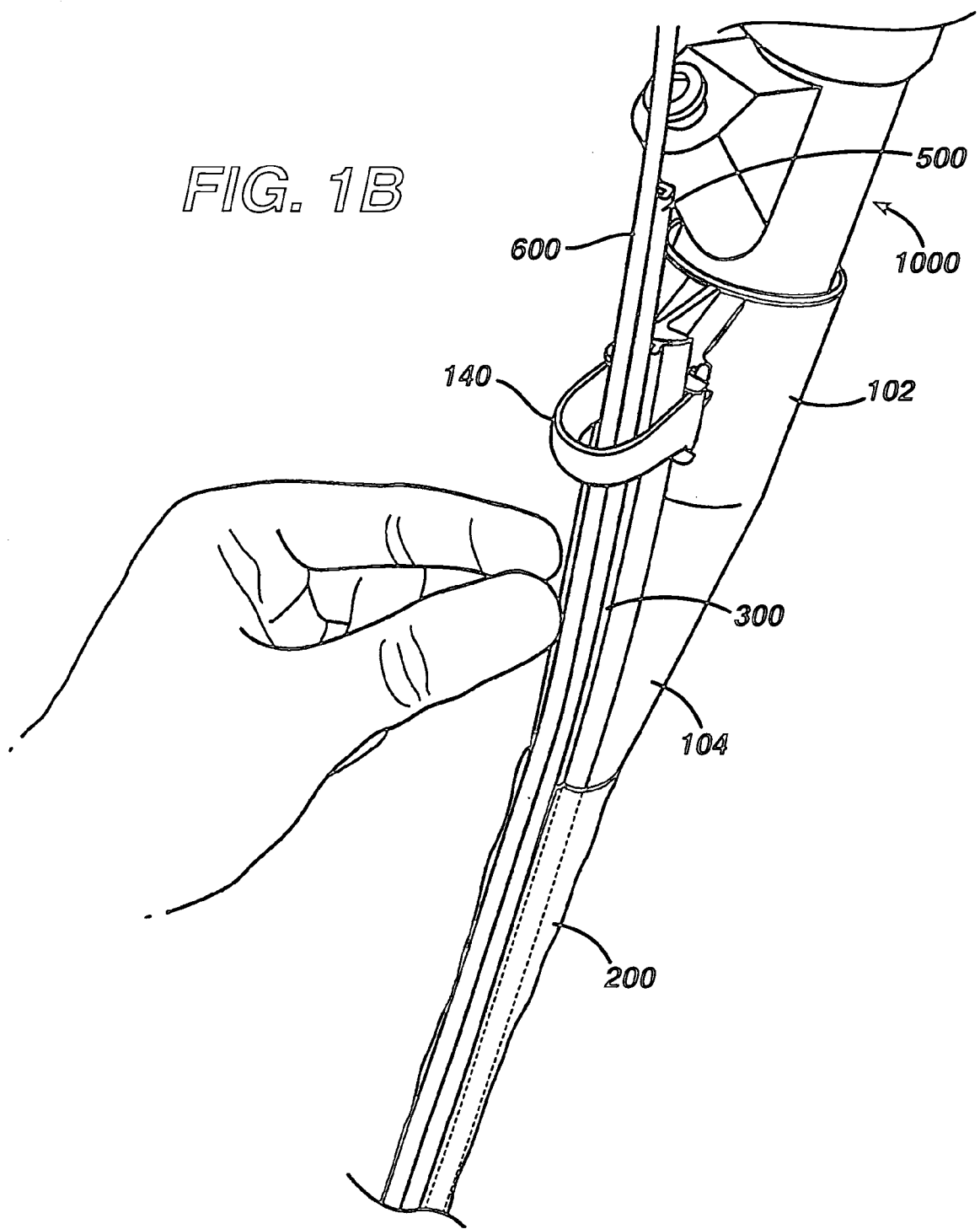
FIG. 1B is a schematic illustration similar to that of FIG. 1A showing the hinged latch in a closed position and feeding tube and carrier being advanced on a track.

FIGS. 1A and 1B illustrate isometric views of an endoscope 1000 inserted into handle 100. A hinged latch 140 can be positioned at or adjacent to the proximal end of track 300. The latch 140 can be hinged to the track ramp 130 or structure 120, such as by a living hinge or a mechanical pin type hinge. The latch is shown in an open position in FIG. 1A and a closed position in FIG. 1B. The latch, when in the closed position, extends over the track 300 at or adjacent the proximal end of the track and can assist in preventing components slidably supported on track 300 from "unzipping" from track 300 or otherwise being dislodged from track 300 during use. In FIG. 1B, a carrier 500 and feeding tube 600 (both described in more detail below) are shown being advanced by hand in a distal direction along track 300.

An elastically extensible member can be employed to provide a distal biasing force on the endoscope and a proximal biasing force on the handle 100. For instance, the handle 100 can include an elastic strap 150 (shown in FIGS. 18 and 19). The elastic strap can extend from a portion of the handle 100, such as the track ramp 130 or the structure 120, to form a loop that encircles a portion of the endoscope 1000, such an endoscope accessory channel port. The elastic strap 150 is useful for accommodating variation in endoscope lengths, assists in maintaining tautness of the sheath, and assists in maintaining engagement of the endoscope in the handle. The elastic strap can be employed to compensate for length changes due to scope bending, and to provide a reslient biasing force urging the endoscope distally into the handle and sheath. Alternatively, instead an elastic strap, a relatively inelastic strap could be used, and a biasing member could be employed in the handle or sheath to maintain the sheath and track from pleating or otherwise "bunching" on the endoscope. For instance, the strap could be generally inextensible, and the handle could be formed of an elastically extensible material or geometry, such that the length of the handle would be extended when the strap was engaged on relatively longer endoscope.

Endcap 400 can be formed of a thermoplastic elastomer for fitting on the distal end of the endoscope 1000. The endcap 400 can be formed of a material having a durometer of less than about 100, and more particularly between about 50 and about 90 (as measured using the A scale, 0.120 inch test according to ASTM D224). The endcap can be pressed onto (e.g. slightly expanded to fit over) the distal end of the endoscope with the distal end of the endoscope being gripped by the endcap 400. One suitable material from which endcap 400 can be formed is molded Santoprene brand thermoplastic elastomer. Providing an endcap 400 from a material such as a thermoplastic elastomer can be desirable in that such an endcap 400 can be pressed onto the distal end of the endoscope, as described in more detail below.

Figure 2A:
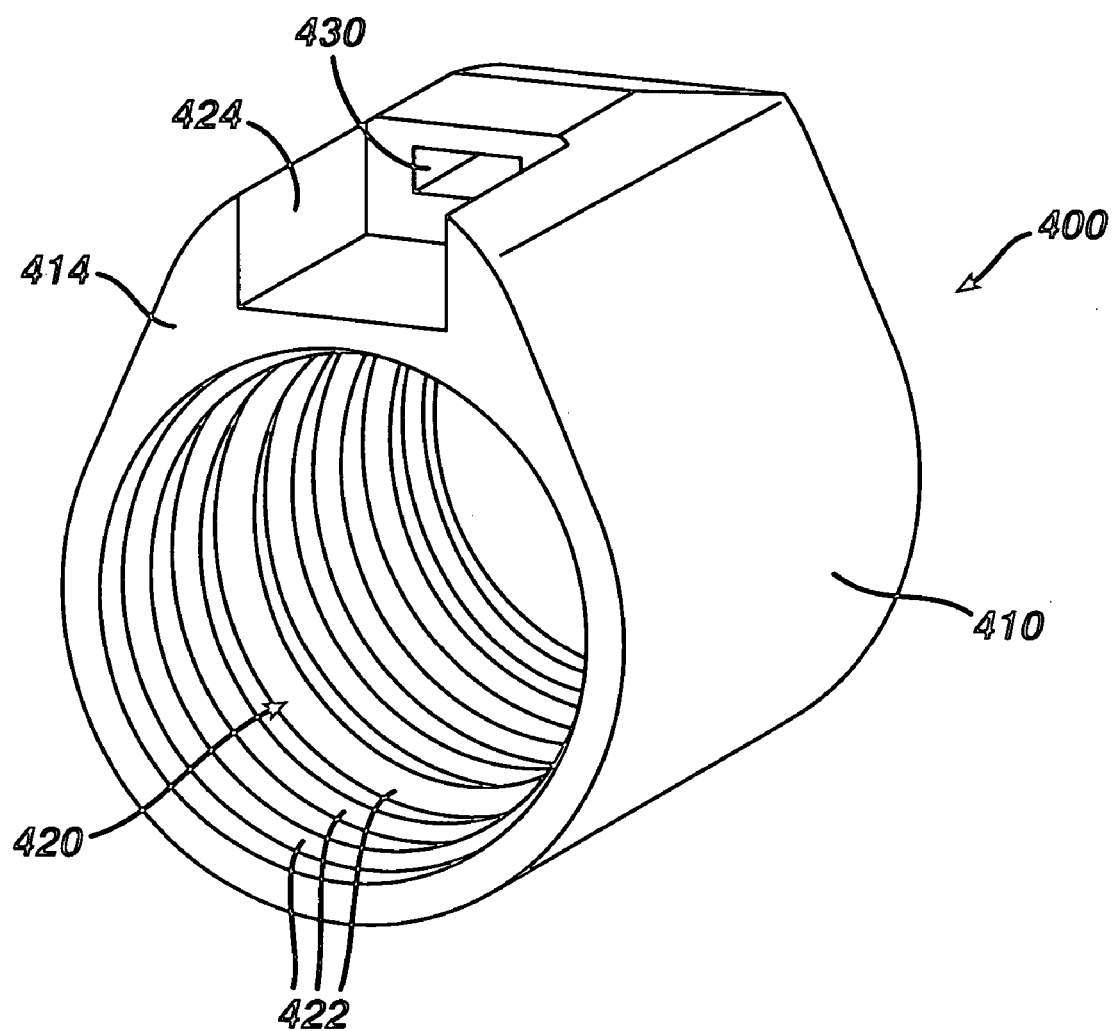
FIG. 2A is a schematic isometric illustration showing the proximal end of the endcap.

Referring to FIGS. 1, 2, and 2A, the endcap 400 can include a generally cylindrical body portion 410, a distal face 412, a proximal face 414, and a central bore opening 420 therethrough for receiving the distal end of the endoscope 1000. The endcap 400 can have internal, circumferentially extending grooves 422 spaced apart along the length of the internal surface of central bore opening 420. A track recess 424 (FIG. 2A) can provided in the upper half of body portion 410. The recess 424 can extend distally from the proximal face 414, and can be sized and shaped to receive the distal end of the track 300. If desired, the proximal edge of the bore opening 420 can be tapered or chamfered to assist in pressing the endcap onto the distal end of the endoscope.

The endcap 400 can also include a slot 430 (FIGS. 2 and 2A) extending through at least a portion of the body portion 410 and opening on the distal face 412. Slot 430 can extend distally from a surface bounding track recess 424, to be disposed with respect to track 300 to be at generally the same "o'clock" position as track 300. Slot 430 can be sized and shaped to receive a tab or other indicator device, as described below. In one embodiment, the proximal end of slot 430 can be generally aligned with channel 320 in track 300 (described below), and the distal end of slot 430 can be inclined radially inwardly as the slot 430 extends from recess 424 in the distal direction, such that a tab or other indicator device extending through slot 430 is directed distally and radially inwardly to be viewable by the optics of the endoscope 1000. The Endcap 400 can be joined to the distal end of the sheath 200 by any suitable method, such as ultrasonic welding.

Figure 3:
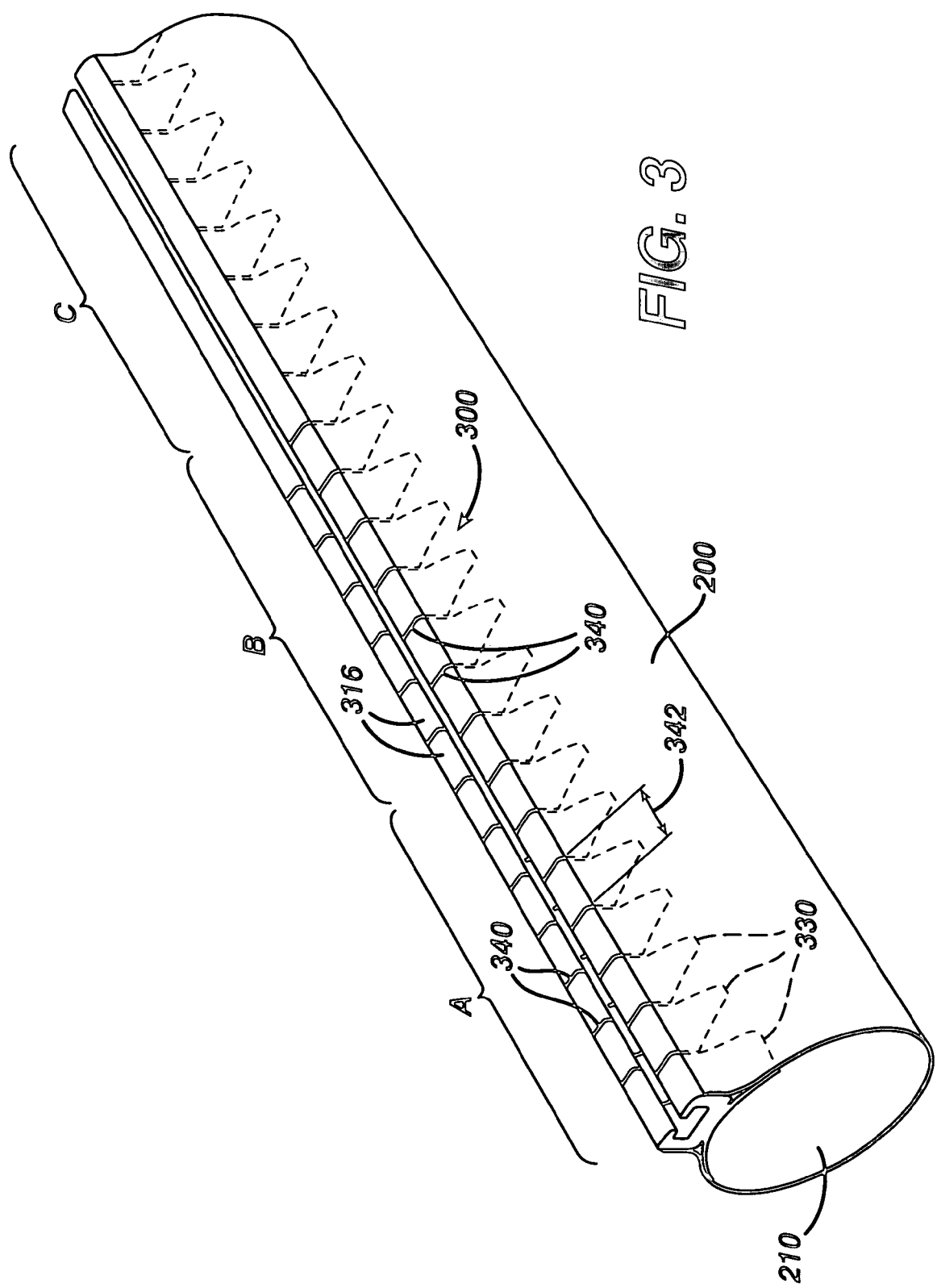
FIG. 3 illustrates different sections of a track disposed on a sheath.
Figure 4:
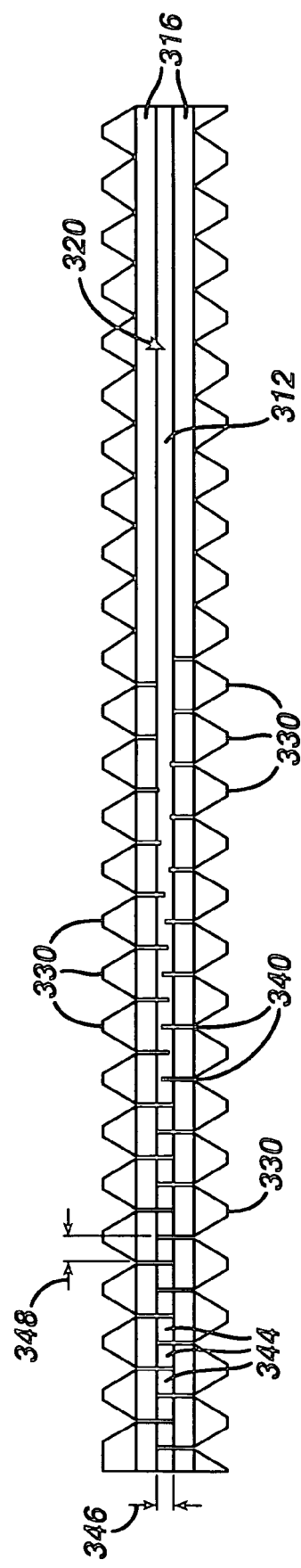
FIG. 4 is a top view illustration of a portion of a track.
Figure 5:
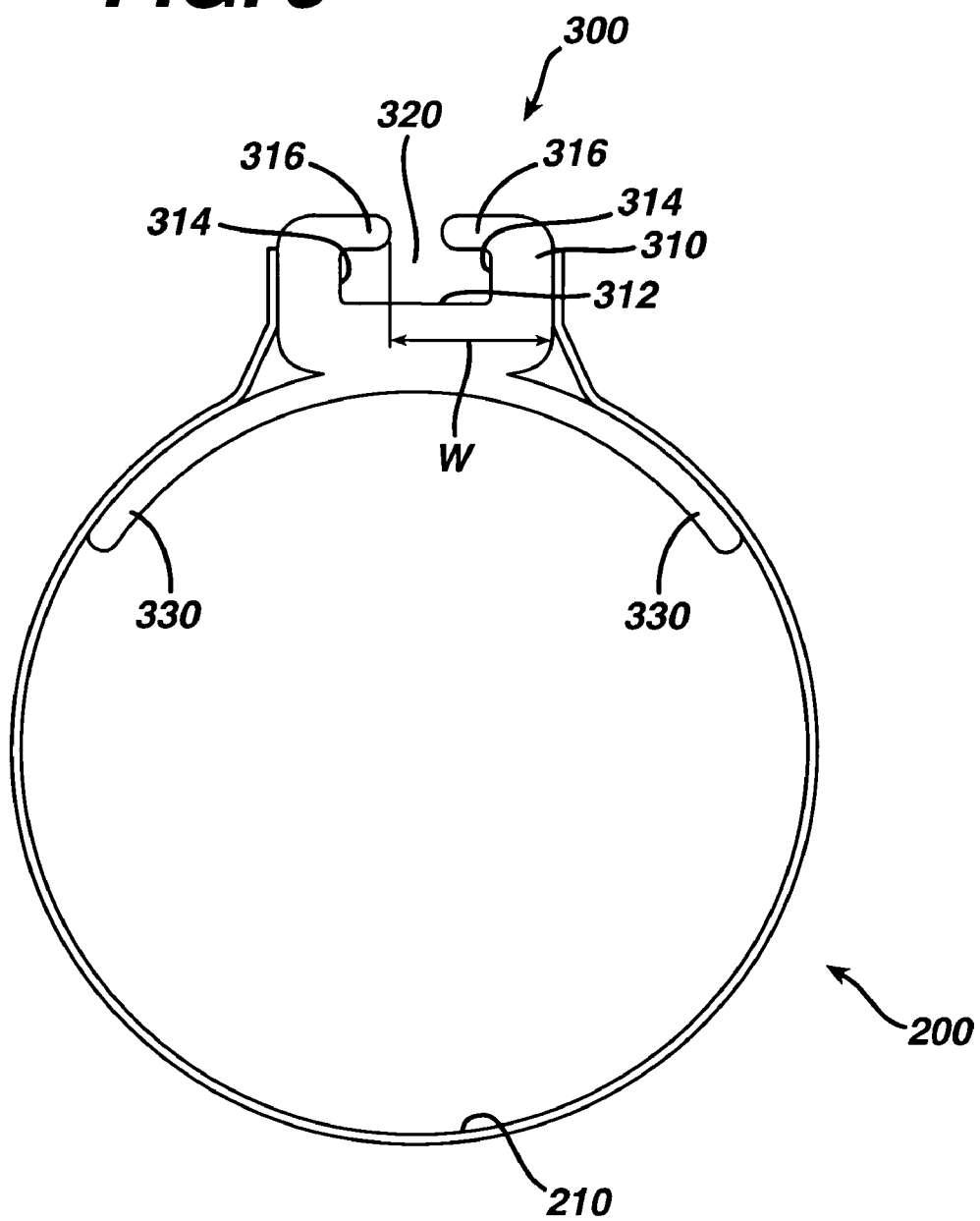
FIG. 5 is a cross-sectional illustration of a track supported on a sheath (it being understood that the sheath may be formed of a thin film that would not maintain the circular configuration shown in FIG. 5 absent an internal member, such an endoscope, being disposed within the sheath).

Track 300 can be supported by sheath 200, and can extend from handle 100 to the endcap 400. FIG. 3 shows track 300 supported on sheath 200 with a portion of the track shown in phantom. FIG. 4 illustrates a top plan view of the track 300, and FIG. 5 illustrates a cross-sectional view of track 300 supported by sheath 200. In FIG. 5, the sheath 200 is shown in cross-section as it would appear if disposed on an endoscope for illustration purposes, with it being understood that, in one embodiment, the wall of the sheath 200 can be generally flaccid and drapable, and lack sufficient stiffness to maintain the shape shown in FIG. 5 without the support of the endoscope or other internal support.

Track 300 can be a generally continuous, unitary piece of material which extends longitudinally a length sufficient to reach from a point outside the patient to a point in or distal to the stomach of the patient, such as through the pylorus and into the small intestine. Track 300 can be formed of a flexible polymeric material, such as extruded polypropelene. One suitable material from which track 300 can be formed is Huntsman 23R2Acs321 available from Huntsman Corp. of Houston Tex. The sheath 200 can be joined to the track 300 by any suitable joining method, such as by ultrasonic welding. The distal end of the track 300 can be over molded onto the end cap 400, or otherwise joined to end cap 400 in recess 424. The handle 100 can be joined to the proximal end of the sheath 200 and the proximal end of the track 300 by any suitable method, such as by ultrasonic welding.

Track 300 can include a generally C shaped channel body 310 defining an inverted T-shaped channel 320 in cross section. The body 310 can include floor 312, upstanding side walls 314, and inwardly extending prongs 316. The body 310 can also include a plurality of circumferentially extending side tabs 330 extending outwardly from body 310. Adjacent tabs 330 on each side of the track 300 can be spaced apart, such as by the scalloping (shown in FIG. 3 in phantom), or by other spacing methods, such as notching, to maintain the flexibility of the track 300. The tabs 330 are shown joined to the inner surface 210 of the sheath 200. Tabs 330 can be joined to the inner surface 210 by any suitable means, such as with adhesive or other bonding methods.

Without being limited by theory, the tabs 330 can be employed to stabilize the track 300 with respect to the endoscope when the endoscope is positioned in sheath 200. The tabs help to maintain radial alignment of the axis of symmetry of the track channel 320 with respect to the endoscope 1000. Accordingly, the sheath 200 and the track 300 can be rotated circumferentially as a unit about the endoscope 1000 to different o'clock positions, and the tabs 330 help to maintain the track 300 (and channel 320) in proper radial orientation with respect to the endoscope. The desired radial orientation of channel 320 is illustrated in FIG. 5, with the cross-sectional centerline and axis of symmetry of channel 320 being generally aligned with a radial line extending from the center of the endoscope.

According to one embodiment of the present invention, the track 300 has at least one portion which has a greater flexibility than another portion of the track. For instance, the track 300 can include a portion having a bending flexibility and axial flexibility that is greater than the bending flexibility and axial flexibility of another portion of the track. Referring to FIG. 3, the track 300 is shown schematically to have three sections of different flexibility. Section A, which can be the distal most portion of the track 300, can be the most flexible portion of the track in both bending and axial extension. Section A can be associated with the distal most portion of the endoscope, such as an articulating portion of the endoscope. Section B can be relatively less flexible (more stiff) than Section A. Section C can be the proximal portion of the track 300 and can be relatively less flexible than region B. In one embodiment, Section A can extend about 10 inches, and Section B can extend about 26 inches. In one embodiment, the length of the track 300 can be at least about 50 inches.

In the embodiment shown in the Figures, Sections A and B are interrupted at intervals along their respective lengths to reduce the bending stiffness and the axial stiffness of the regions, while Section C can be generally uninterrupted. The interruptions in Sections A and B are provided by a series of slits 340. As shown in FIGS. 3 and 4, the slits 340 on the two sides of the track body 310 are staggered (longitudinally offset) relative to each other such that the slits on one side of the track body 310 are not aligned with the slits on the other side of the track body 310. In the embodiment shown, each slit 340 on one side of the track is positioned halfway between the two adjacent slits on the opposite side of the track. Each of the tabs 330 can be positioned between a pair of adjacent slits 340. In one embodiment, the slits 340 can have a width (measured parallel to the length of channel 320) of less than about 0.010 inch, more particularly, less than about 0.005 inch. The slits 340 can be formed by any suitable knife or other cutting instrument. Without being limited by theory, the width and staggering of the slits 340 can provide sufficient flexibility of the track 300, while preventing a member slidably disposed in the track from "unzipping" from the carrier, or "popping out of" the track, such as by deflection of prongs 316, at positions where the endoscope is bent (or other configuration where the track is bent or otherwise to take on a curved configuration). The provision of selectively placed interruptions in the track permits the track to follow the curvature of the endoscope without significantly increasing the bending stiffness of the assembly of the sheath 200 and endoscope.

In one embodiment, the slits 340 extend through the full thickness of the track (thickness as measured in the vertical direction in FIG. 5). Additionally, the slits can extend from one side of the track to extend across the full the width of one of the prongs 316, and the slits can extend at least halfway across the floor 312.

In the embodiment shown in FIGS. 3 and 4, each of the slits 340 can extend through the full thickness of the track. Additionally, depending upon the location of the slits 340 along the length of the track, the slits 340 can extend more than halfway, but not fully across the width of the track. For instance, the slits 340 extend across the longitudinal centerline of the track in Section A of FIG. 3. Referring to FIG. 5, the dimension W illustrates the width of a slit extending more than halfway, but not fully across the width of the track. The spacing 342 (FIG. 3) between slits 340 on the same side of the track 3090 can be about 0.120 to about 0.130 inch in Section A and about 0.250 inch in Section B.

The staggered arrangement of slits 340 that extend beyond the centerline of the track can provide the advantage that the track 300 does not have a longitudinally continuous load path for carrying tensile loads or bending loads. Without being limited by theory, the staggered arrangement of slits 340 can be viewed as providing bending sections (indicated by reference number 344 in FIG. 4) in the track 300. The bending sections 344 can have a length 346 (FIG. 4) defined by the amount the slits 340 on opposite sides of the track overlap, and the bending sections 344 have a width 348 defined by the longitudinal spacing of one slit from the immediately adjacent slit extending from the opposite side of the track. In one embodiment, the length 346 can be about 0.038 inch to about 0.040 inch in Section A, and the width 348 can be about 0.0625 inch.

Figure 6:
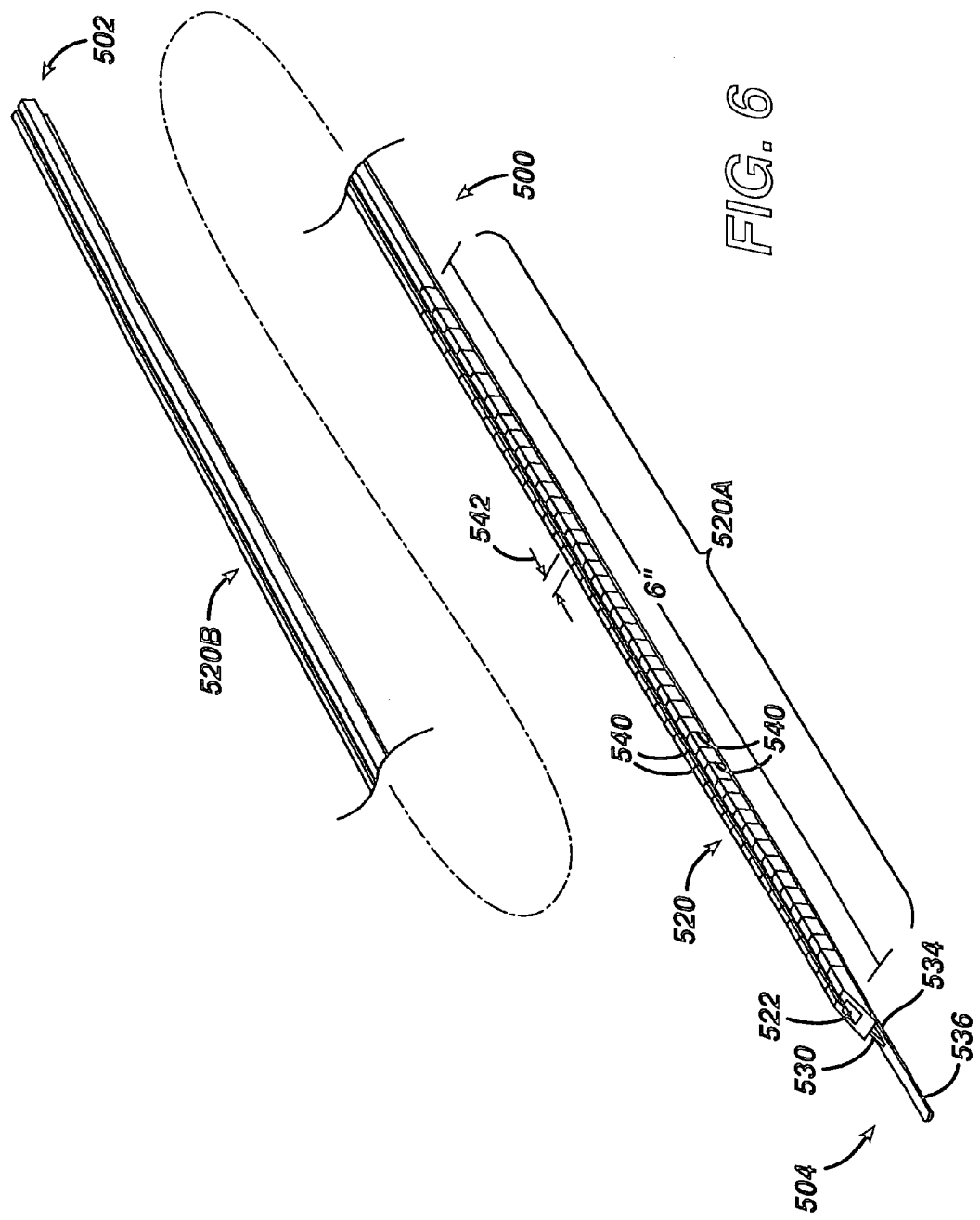
FIG. 6 is a schematic illustration of a feeding tube carrier in accordance with one embodiment of the present invention.
Figure 7:
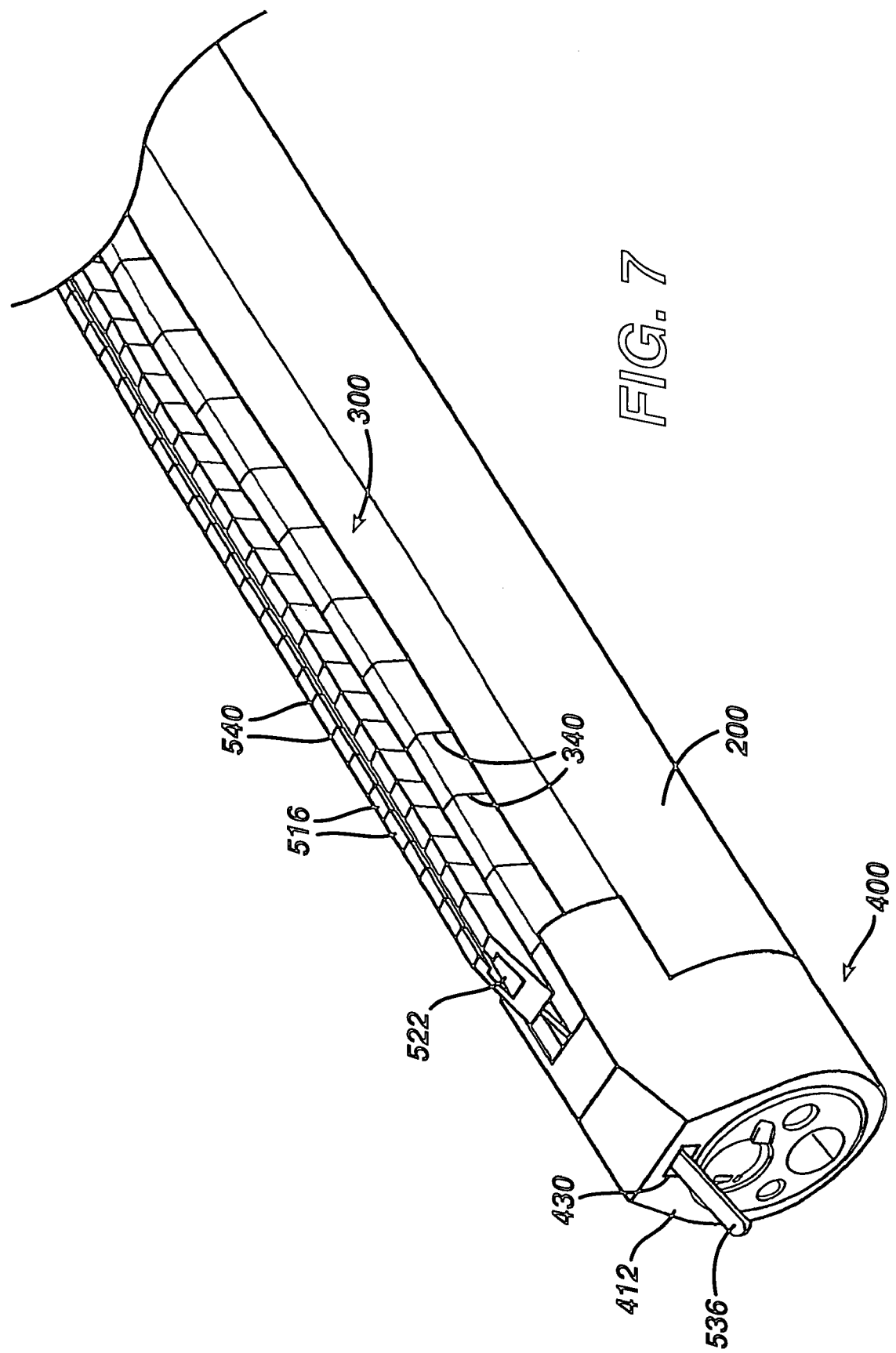
FIG. 7 is a schematic illustration of a distal portion of a sheath and track showing a carrier advanced to a distal position on the track, and with an indicator tab extending through a slot in an endcap to be viewable by an endoscope.

FIG. 6 illustrates carrier 500, and FIG. 7 illustrates carrier 500 advanced to distal most position on track 300. Carrier 500 can extend from a proximal end 502 to a distal end 504. The length of carrier 500 can be a length sufficient to reach from a point outside the patient to a point within, or distal to, the patient's stomach. In one embodiment, the length of carrier 500 can be at least about 100 cm, and more particularly at least about 72 inches. The carrier 500 can include a body 520, a generally vertically extending web 530, and a track engaging rail 534. Carrier 500 slidably engages track 300, with rail 534 being sized and shaped to be slidable within channel 320 of track 300. Carrier 500 can be of unitary construction, and can be molded or otherwise formed of a suitable material. In one embodiment, carrier 500 is formed of a relatively low friction materials, such as extruded PTFE (Teflon).

Figure 8:
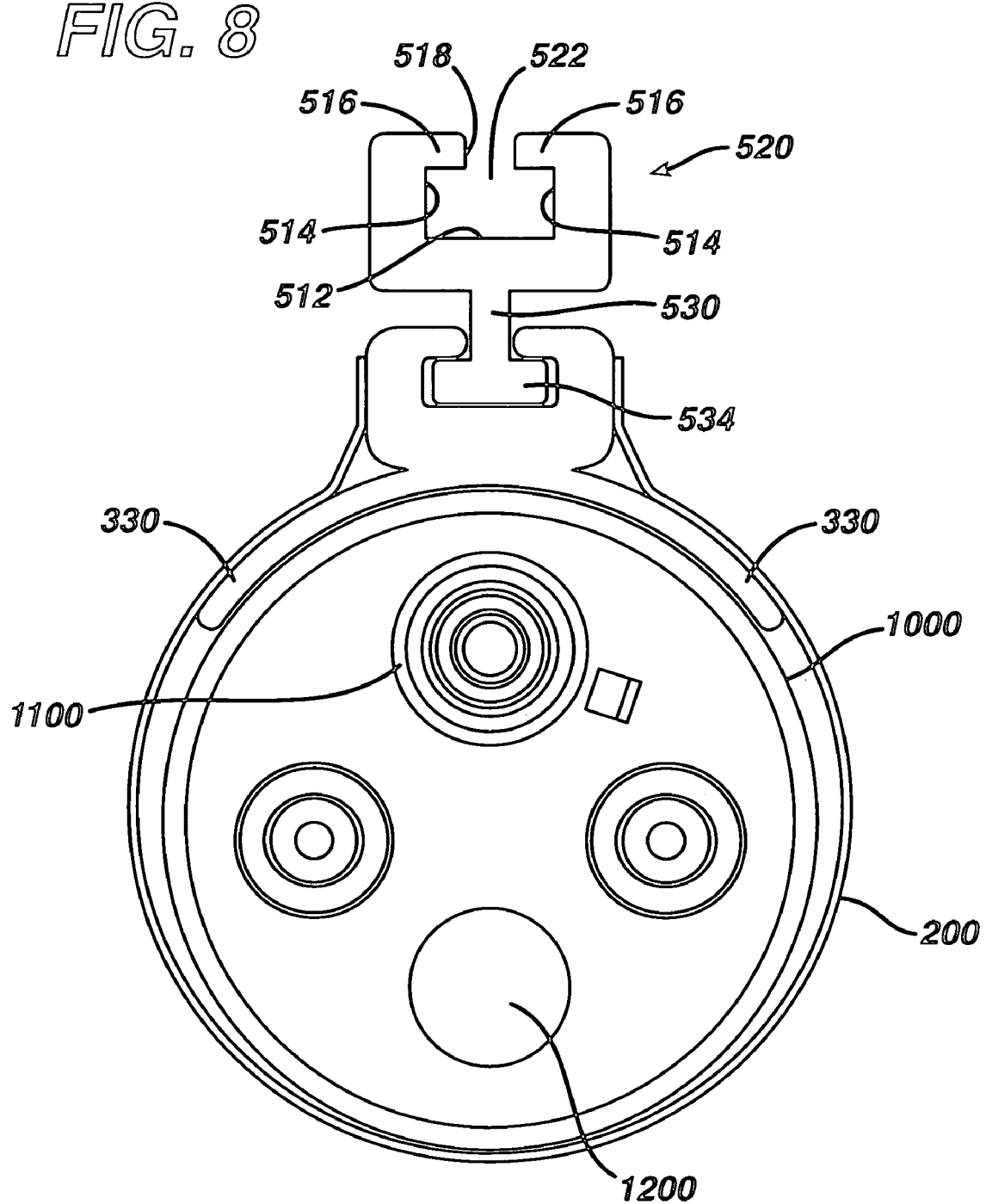
FIG. 8 is a schematic illustration showing the distal end of an endoscope being advanced through a sheath, with the sheath, track, and carrier shown in cross-section.

FIG. 8 provides a cross-sectional illustration of carrier 500 supported on track 300, with the distal end of endoscope 1000 illustrated being advanced through the cross-section to illustrate one position of components on the endoscope's distal end relative to the position of the track 300. As shown in FIG. 8, the web 530 extends generally radially inwardly from body 520, to position the rail 534 radially inward of the carrier body 520. The cross-section of web 530 and rail 534, together, can provide a generally inverted "T" configuration.

The carrier body 520 can include a channel 522. Channel 522 can extend substantially the full length of body 520. The channel 522 can be bounded by a channel floor 512 and oppositely facing sidewalls 514. The body 520 can also include inwardly extending prongs 516 having oppositely facing sides 518 which are spaced apart to define the throat of the opening of channel 522.

The distal most portion of the track engaging rail 534 can extend distally beyond body 520 to provide a flexible indicator tab 536. Tab 536 can be sized and shaped to be received by slot 430 in endcap 400. As the carrier 500 is advanced distally on track 300, the tab 536 will be viewable by the optics of endoscope 1000 once the carrier 500 has reach its distal most position on track 300. Referring to FIGS. 7 and 8, the tab 536 can be viewed through endoscope optics element 1100 as tab 536 is advanced distally and radially inwardly from the distal end of slot 430.

In one embodiment, the carrier 500 has at least one portion which has a greater flexibility than another portion of the carrier For instance, the carrier 500 can include a body 520 having a distal portion 520A having a bending flexibility and axial flexibility that is greater than a more proximal body portion 520B of the carrier. Referring to FIG. 6, the carrier is shown schematically to have two sections of different flexibility. Carrier section 520A can be the distal most portion of the carrier, and can be the most flexible portion of the carrier in both bending and axial extension. Section 520A can have a length of at least about 2 inches. In one embodiment, the length of Section 520A is between about 4 inches and about 10 inches, and more particularly, the length of section 520A can be between about 6 and about 8 inches.

In the embodiment shown in the Figures, body section 520A is shown interrupted at intervals along its length to reduce the bending stiffness and the axial stiffness of the distal portion of the body 520. The interruptions can be provided by a series of slits 540. As shown in FIGS. 6 and 7, the slits 540 on the two sides of the carrier body 520 are staggered (longitudinally offset) relative to each other such that the slits on one side of the body 520 are not aligned with the slits on the other side of the body 520. In the embodiment shown, each slit 540 on one side of the carrier body is positioned axially halfway between the two adjacent slits on the opposite side of the track. Adjacent prongs 516 can be separated by slits 540.

Without being limited by theory, the flexible tab 536 and the slits 540 can help to prevent the distal portion of the carrier 500 from "jumping out" of or "unzipping from" the track. For instance, flexible tab 536 can "bridge" the space between the slits 340 in track 300 to help prevent the carrier from being discharged radially from the track 300. Without being limited by theory, the width and staggering of the slits 540 can also provide sufficient flexibility of the carrier 500, while preventing a member slidably disposed in the carrier from "unzipping" from the carrier, or "popping out of" the carrier.

In one embodiment, the slits 540 can extend through the full thickness of the track (thickness as measured in the vertical direction in FIG. 8). Additionally, the slits can extend from one side of the track to extend across the full the width of one of the prongs 516, and the slits can continue through at least a portion of the floor 512. Each of the slits 540 can extend through the full thickness of the track body 520, and each of the slits 540 can extend more than halfway, but not fully across the width of the track. The spacing 542 (FIG. 6) between slits 540 on the same side of the carrier body can be between about 0.1 inch and about 0.6 inch in carrier body portion 520A. The staggered arrangement of slits 540 provide the advantage that the carrier body portion 520A does not have a longitudinally continuous load path for carrying tensile loads or bending loads.

FIGS. 9-13 illustrate a feeding tube 600 which can be used with the track 300 and the carrier 500. Feeding tube 600 can have a proximal end 602 and a distal end 604. Feeding tube 600 can include a feeding tube body 610 having a nutrient passageway 620 for passing nutrients, and a feature 660 adapted to provide releasable engagement of the feeding tube 600 with another member. For instance, the feature 660 can include a rail for providing sliding engagement of the feeding tube with a track or the carrier 500.

Figure 10:
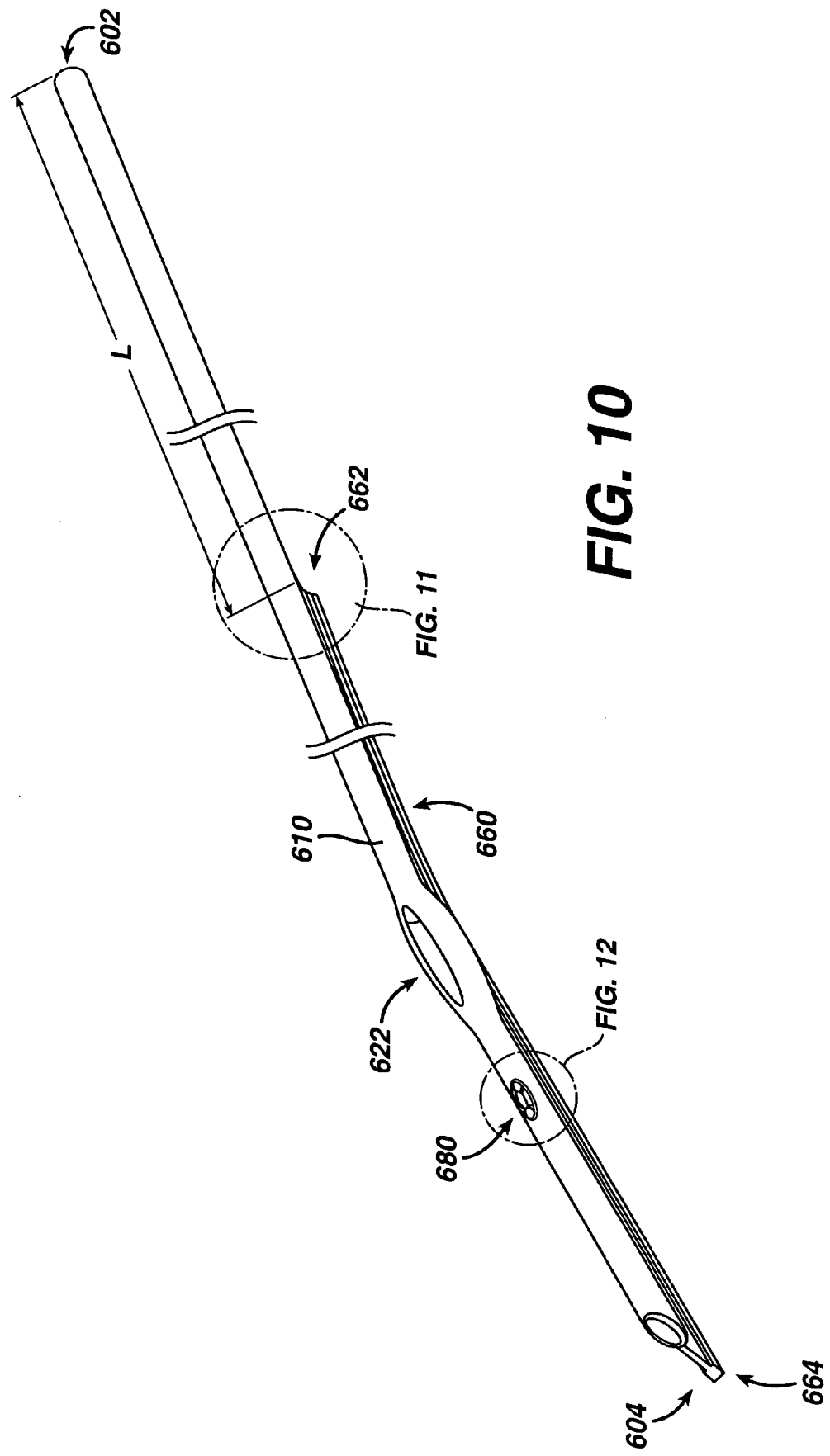
FIG. 10 is a schematic illustration of a feeding tube having a feature for providing sliding engagement with a track.
Figure 13:
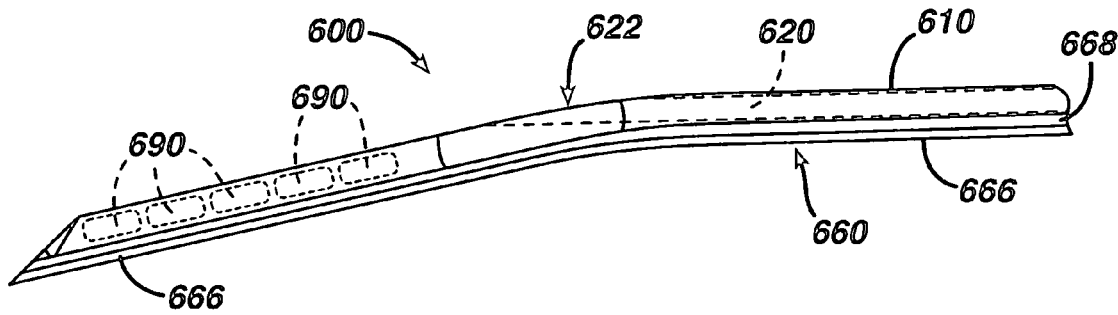
FIG. 13 is a schematic side view illustration of a distal portion of the feeding tube shown in FIG. 10, illustrating a distal portion of a passageway (in phantom) through which nutrients may be directed, such that the distal portion of the passageway does not have to bend or curve to communicate with a distal feeding port, with the portion of the feeding tube extending distally of the distal feeding port being inclined with respect to the passageway, and the figure illustrating weights (in phantom) which may be employed at a distal end of the feeding tube.

The passageway 620 can extend from proximal end 602 to an exit port 622 through which nutrients exit the passageway 620 and enter the patient's GI tract. The portion of the feeding tube 600 extending distally of exit port 622 can be inclined with respect to the longitudinal axis of the passageway 620, as shown in FIGS. 10 and 13, and with exit port 622 having a generally tapered, elongated configuration. Accordingly, as shown in FIGS. 10 and 13, the passageway 620 can be generally parallel with respect to the longitudinal axis of the feeding tube 610, and the passageway 620 does not bend or curve to communicate with the exit port 622, except to the extend the tube 610 itself is bent. Having the passageway 620 run substantially straight to exit port 622 and the distal tip portion of the feeding tube inclined with respect to the passageway 620 can provide the advantage that passageway 620 can be easily cleaned, such as by running a wire from the proximal entrance of the feeding tube through the passageway 620 and out through exit port 622.

Figure 12:
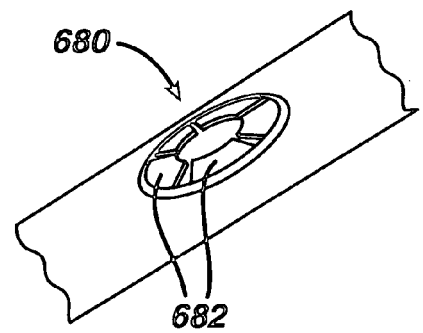
FIG. 12 is a schematic illustration of a port for use in maintaining the feeding tube in a desired position in the gastrointestinal tract after the feeding tube is positioned and the track has been withdrawn from the GI tract.

Referring to FIG. 12, feeding tube 600 can include one or more suction ports positioned either proximally or distally of exit port 622. Suction ports can be used to hold the distal end of the tube 600 in a desired position within the body once the tube 600 is placed, and prevent migration of the feeding tube 600 during feeding. In FIG. 10, a suction port 680 is shown positioned distally of exit port 622. Suction port 680 can include a plurality of radially inwardly extending tabs 682 which can engage and hold tissue when tissue is drawn into the tube 600 by vacuum applied to suction port 680. The tabs 682 can be formed by cutting or slitting the outer wall of tube body 610 to create the tabs 682, or tabs 682 can be provided in a separate member, such as a metallic or non metallic insert that is formed to include tabs 682, and which is positioned in an aperture in the wall of tube body 610. Vacuum can be communicated to suction port 680 through a vacuum passageway (not shown) which communicates with, or extends separately of, nutrient passageway 620. Weights 690 can be disposed in the distal end of tube 600 to assist in maneuvering and positioning the feeding tube 600.

The feature 660 can extend along at least a portion of the length of feeding tube 600. In FIG. 10, the feature 660 is shown extending along some, but not all of the length of the feeding tube 600. Feature 660 can extend from a proximal end 662 of feature 660 to a distal end 664. The proximal end 662 of the feature 660 can be spaced from the proximal end of the feeding tube 600 by a distance L, so that the portion of the feeding tube 600 which extends through the throat and/or nose of the patient when the feeding tube 600 is in place does not irritate the patient or interfere with feeding. The distance L can be between about six inches and about 24 inches, and in one embodiment is about 18 inches.

Figure 9:
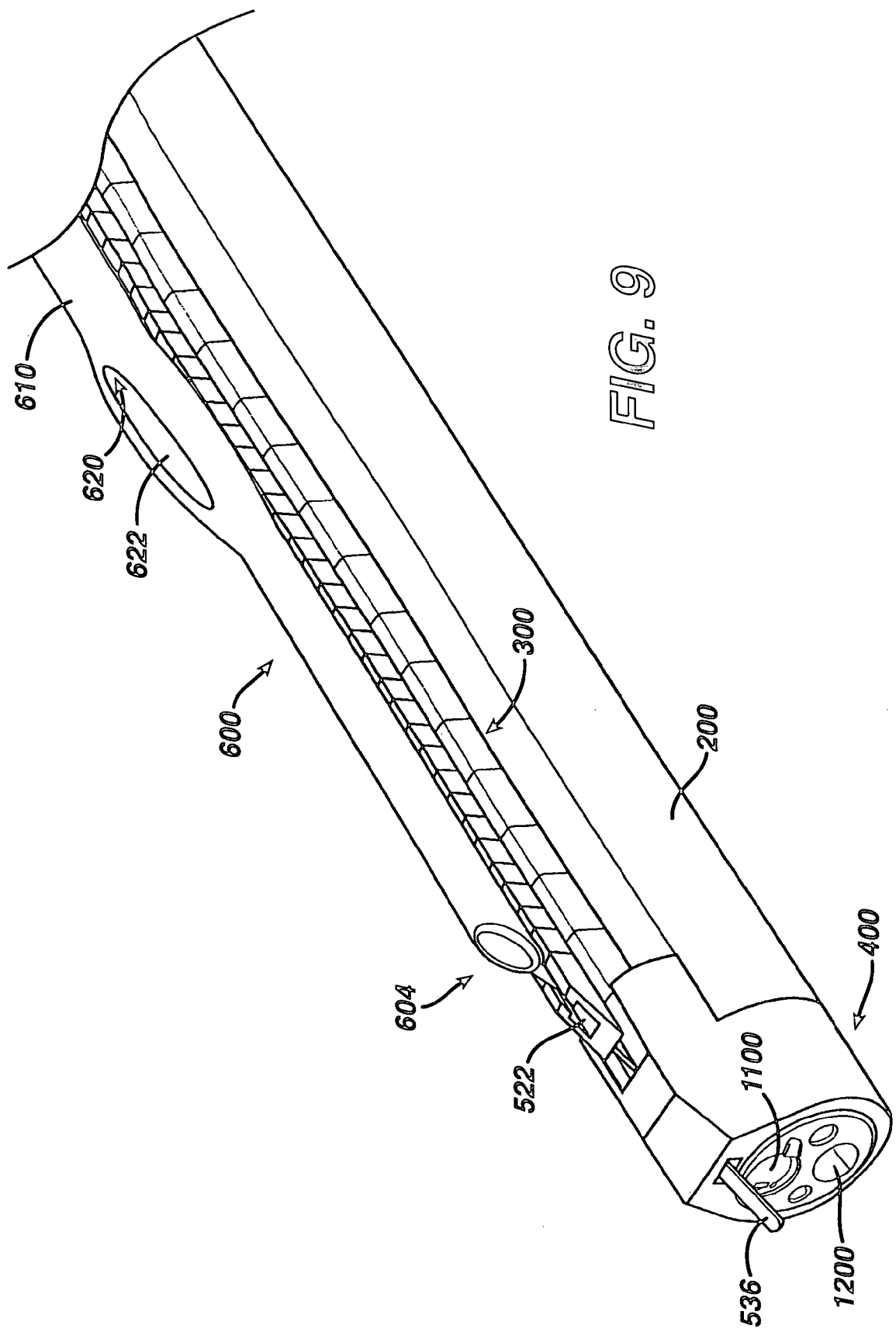
FIG. 9 is a schematic illustration of a distal portion of a sheath, track, and carrier, and illustrating the carrier and a feeding tube advanced to a distal position on the track.

The feature 660 can be integrally formed with the tube body 610 (such as by molding or extruding). Alternatively, the feature 660 could be manufactured separately from tube body 610, and subsequently attached to body 610, such as by use of any suitable bonding or joining method. Feature 660 can be sized and shaped to permit the feeding tube 600 to releasably engage another member, such as track 300 or carrier 500, such as by sliding engagement. In FIG. 9, the feeding tube 600 is shown slidably supported on carrier 500. The feature 660 can comprise a rail 666 and a web 668, with web 668 extending generally radially from tube body 610 to support rail 666 in spaced relationship from tube body 610. In FIG. 9, rail 666 is positioned in channel 522, with web 668 extending through the throat of channel 522. Without being limited by theory, it is believed that slidably supporting the feeding tube 600 on carrier 500 while slidably supporting the carrier 500 on track 300 is advantageous in providing for smooth, relatively low friction positioning of feeding tube 600 within the patient. Alternatively, feeding tube 600 could be slidably supported directly on track 300, such as by having rail 666 engage track 300 directly. For example, if desired, the track 300 could be coated with Teflon or any other suitable low friction coating.

Figure 11:
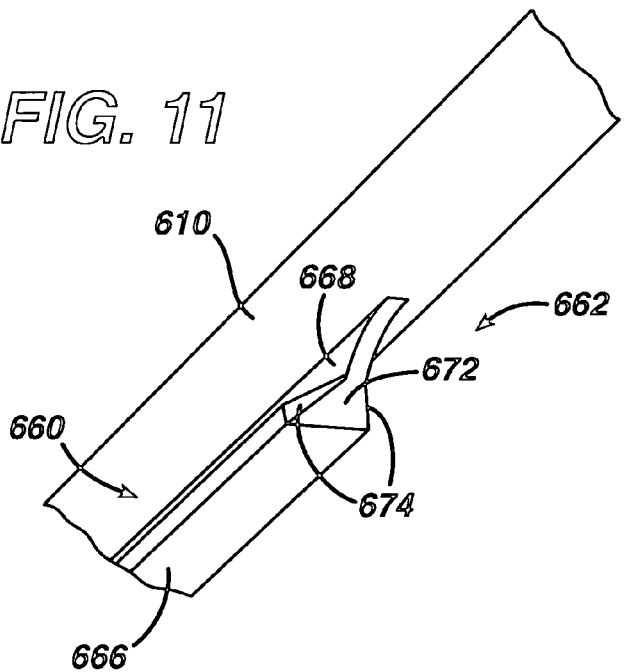
FIG. 11 is a schematic illustration of the proximal portion of the feature shown in FIG. 10.

FIG. 11 illustrates the proximal end 662 of feature 660. A tapered surface 672 can be provided at proximal end 662 to prevent tissue from being caught or pinched as web 668 and rail 666 slide with respect to the channel 522 of carrier 500. The proximal end of rail 666 can be formed, such as by tapering, to provide contact surfaces 674 disposed at the proximal end of rail 666, on either side of web 668. Contact surfaces 674 can be angled with respect to the longitudinal axis of the feeding tube 600 (in FIG. 11 the surfaces 674 are inclined to extend outwardly as they extend distally). The contact surfaces 672 provide a surface at which a force can be provided to feature 660 in order to push the feeding tube 600 distally along carrier 500. The orientation of the contact surfaces 672 can be selected with respect to the longitudinal axis of the feeding tube 600 such that the force applied to push the tube 600 distally on carrier 500 does not tend to push the feature 660 out of the channel 522 in carrier 500.

If desired, the carrier 500 and the feeding tube 600 with feature 660 can be packaged together. For instance, the carrier 500 and feeding tube 600 could be packaged together, with the feeding tube 600 pre-assembled on the carrier 500 such as by sliding engagement of the tube with the carrier 500. The assembly of the carrier 500 with the tube 600 supported along the length of the carrier can be unpackaged (such as from sterile packaging) at the point of use, and the assembly of the carrier 500 and tube 600 could be advanced along the track 300.

FIG. 14 is a side view illustration of the distal portion of a feeding tube positioning member 700. Member 700 can be used to push the feeding tube distally along the carrier 500 and/or to maintain the feed tube 600 in a desired position in the GI tract as the endoscope is withdrawn from the patient. FIG. 15 is an enlarged illustration of the distal end of the member 700. FIG. 16 illustrates the member 700 positioned to maintain the feeding tube 600 in a desired position, and FIG. 17 is an enlarged bottom view of the engagement of the distal end of member 700 with proximal end 662 of feature 660 on feeding tube 600. In one embodiment, the length of member 700 can be at least about 36 inches so that the member 700 can extend from a point outside the patient to engage the contact surface 672 on the feeding tube 600 when the feeding tube is positioned in a desired location in the patient's GI tract.

Referring to FIGS. 14 and 15, the member 700 can have a structure similar to that of the carrier 500. Alternatively, member 700 can have a different cross-sectional shape. The member 700 can include a body portion 710, which may include slits 740 to provide flexibility. The member 700 can include a rail 766 and a web 768, with web 768 extending from body 710 to support rail 766 in spaced relationship body 710. Rail 766 can be sized and shaped for sliding movement within channel 520 of carrier 500.

As shown in FIG. 15, the distal end 702 of member 700 can have a tapered surface 772 on body portion 710. The distal end of rail 766 can be formed to have a V shaped notch with two surfaces 774 being provided to engage surfaces 674 on the feeding tube 600. The surfaces 774 are positioned distally of the surface 772 and are sized and shaped to contact surfaces 674 on feeding tube 600 such that the rail 766 of member 700 can be employed to exert a force on rail 666 of the feeding tube which force is generally parallel to the rail 766 and rail 666. Such surfaces can provide a desired longitudinally directed force without a radial force component, or other force component that might urge feeding tube 600 out of the carrier 500 in an undesired manner.

The endoscope with sheath 200 and track 300 can be positioned in a patient such that the distal end of the endoscope is positioned at a desired position within the GI tract for feeding tube placement. The feeding tube 600 can be positioned on carrier 500 by sliding the feeding tube onto carrier 500 outside of the patient (or the feeding tube 600 and carrier 500 can be provided in a pre-packaged assembly), and the carrier 500 and feeding tube 600 can then be advanced together along track 300 to a desired position in the GI tract, such as with the distal portion of the feeding tube positioned in the stomach or small intestine. The tab 536 on carrier 500 can be viewed through the endoscope optics once the tab 536 extends through the endcap 400, thereby providing visual indication that the carrier and feeding tube have reached the desired position. Alternatively, the carrier 500 could be advanced to along the track 300, and then the feeding tube 600 could be advanced along the carrier 500 to the desire position.

Once distal end of the feeding tube 600 has been advanced to a desired position in the body, the endoscope, sheath 200, track 200, and carrier 500 can be removed from the GI tract leaving the feeding tube in place. In order to prevent the feeding tube from "backing out" or otherwise moving in a proximal direction as the other components are removed from the body, feeding tube positioning member 700 can be employed to maintain the position of the feeding tube during removal of the other components. After positioning of the feeding tube 600 (and prior to removal of the endoscope, sheath 200, track 300, and carrier 500), the member 700 can be inserted in carrier 500 (with rail 766 positioned in channel 520 of carrier 500 so that member 700 slidably engages carrier 500) and the member 700 can be advanced distally along the carrier 500 until the distal end of the member 700 is adjacent the proximal end 662 of the rail 666 on feeding tube 600. As the endoscope, sheath 200, track 300, and carrier 500 are withdrawn in a proximal direction from the patient's body, the member 700 can be held in place (such as by the hands of the physician, a physicians assistance, or a fixture) to maintain the member 700 stationary with respect to the endoscope, sheath, track, and carrier, and exerting a force on the feeding tube rail 666 at the interface of surfaces 774 and surfaces 674, thereby "blocking" the feeding tube 600 from backing up proximal during withdrawal of the endoscope and other components.

Figure 18:
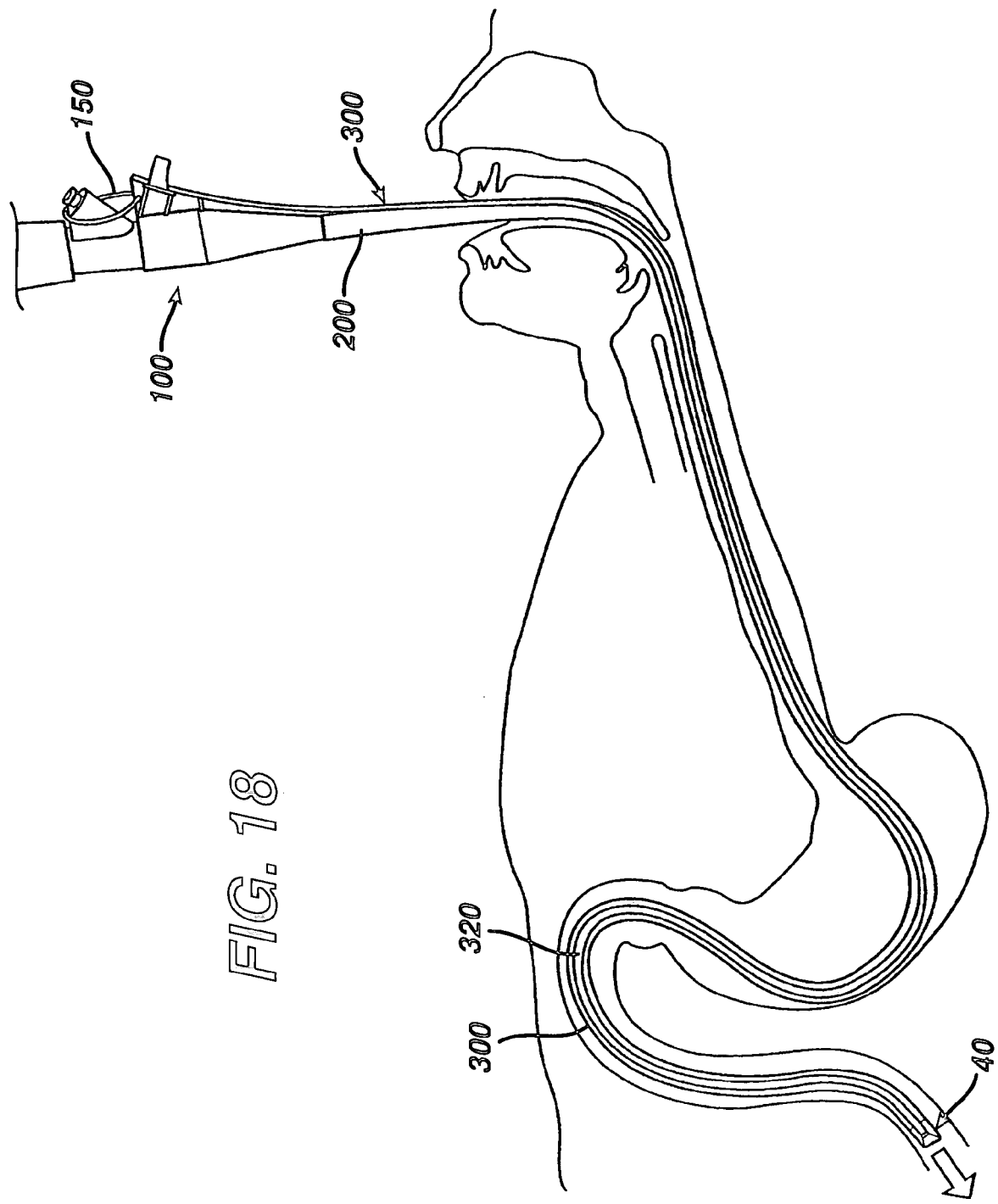
FIG. 18 illustrates introducing an endoscope in a medical device (which medical device can include a handle, sheath, endcap, and track) into the GI tract of a patient, such that the endcap and the distal end of the track are positioned in the small intestine (such as in the jejunum).

FIGS. 18-24 illustrate steps which may be employed in a method for positioning a feeding tube according to one embodiment of the present invention. The endoscope can be inserted into the sheath 200, with the endcap 400 positioned at a distal end of the sheath 200, the handle 100 positioned at a proximal end of the sheath 200, and with the track 300 extending along the sheath 200 from the endcap 400 to the handle 100. As used herein after, the term "sheath assembly" shall refer to the assembly of the sheath 200, handle 100, endcap 400, and track 300. After inserting the endoscope into the sheath assembly outside of the patient, the sheath assembly and endoscope can be inserted into a naturally occurring body opening, such as the mouth, and the sheath assembly with endoscope can be advanced so that the distal end of the endoscope and the endcap 400 are positioned at a desired location, such as the small intestine. FIG. 18 illustrates sheath assembly positioned in the GI tract of a patient, with the track 300 extending from a position outside the body to a position in the small intestine.

Figure 19:
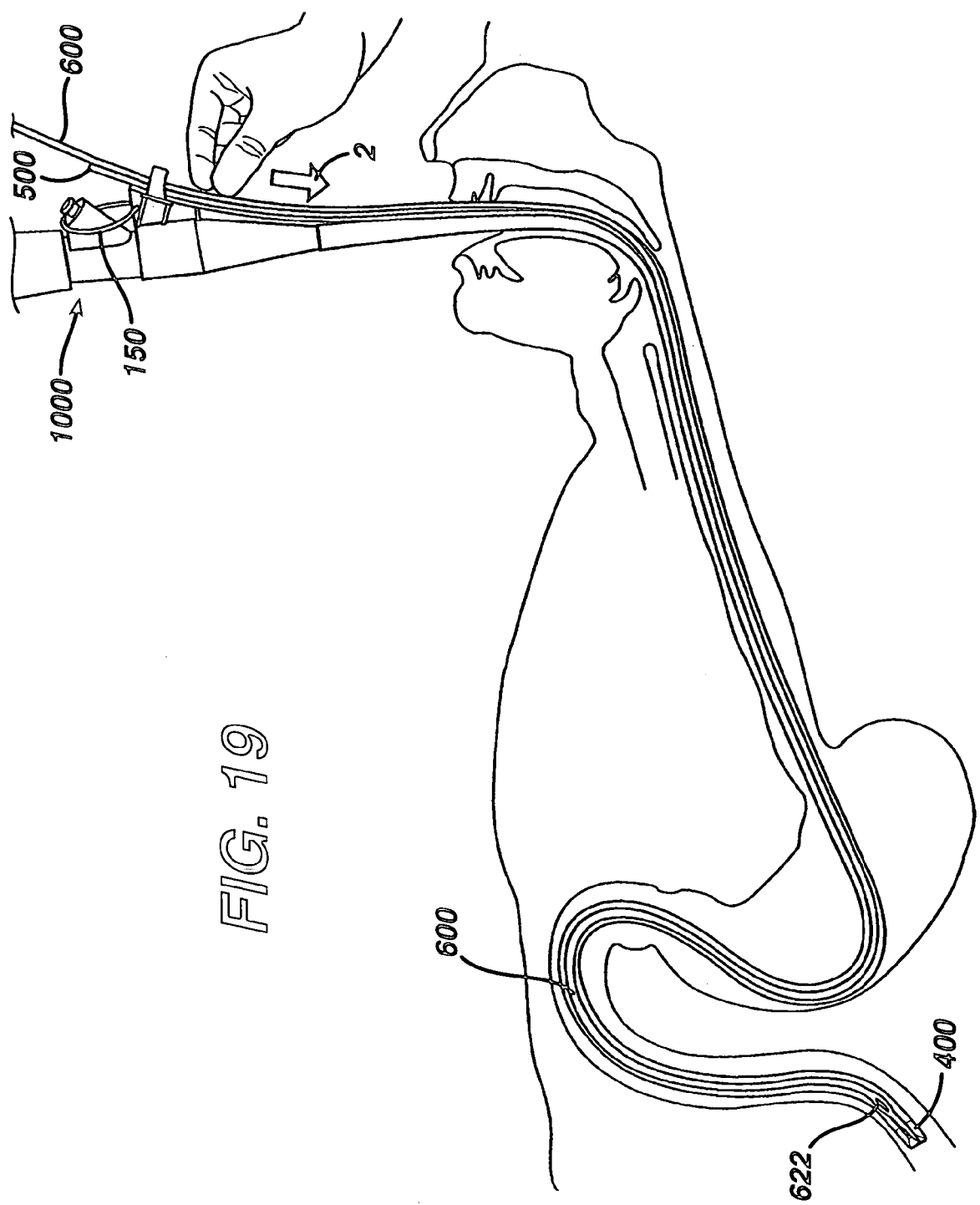
FIG. 19 illustrates advancing a carrier and a feeding tube together on the track after the endoscope and track have been positioned as shown in FIG. 18, so that the distal end of the feeding tube is positioned in the jejunum.

The feeding tube 600 can be positioned on the carrier 500 outside of the patients body, such as by sliding the feeding tube rail 666 in the channel 520 of the carrier 500 until the feeding tube 600 is positioned along the length of the carrier 500, with the distal end of the feeding tube positioned at or adjacent to the distal end of the carrier 500. Referring to FIG. 19, the carrier 500 and feeding tube 600 can then be advanced (such as by hand in the direction of arrow 2) together along track 300, with the carrier and feeding tube being advanced from a position outside the patient to a position where the distal end of the feeding tube is positioned at a desired location (the small intestine in FIG. 19). The length of feeding tube 600 can, in one embodiment, be at least about 140 cm long, and the distal end of the feeding tube can be positioned between about 130 to about 140 cm from the patients incisors. By way of non-limiting example, a 140 cm length 10 Fr Dobb-Hoff-type feeding tube (available from Viasys Healthcare, Inc.) can be modified to have the rail 666 feature, such as by bonding or otherwise attaching a web and rail to the tube. A pediatric colonoscope, such as an Olympus model PCF100 pediatric colonoscope can be employed with the sheath assembly.

Figure 20:
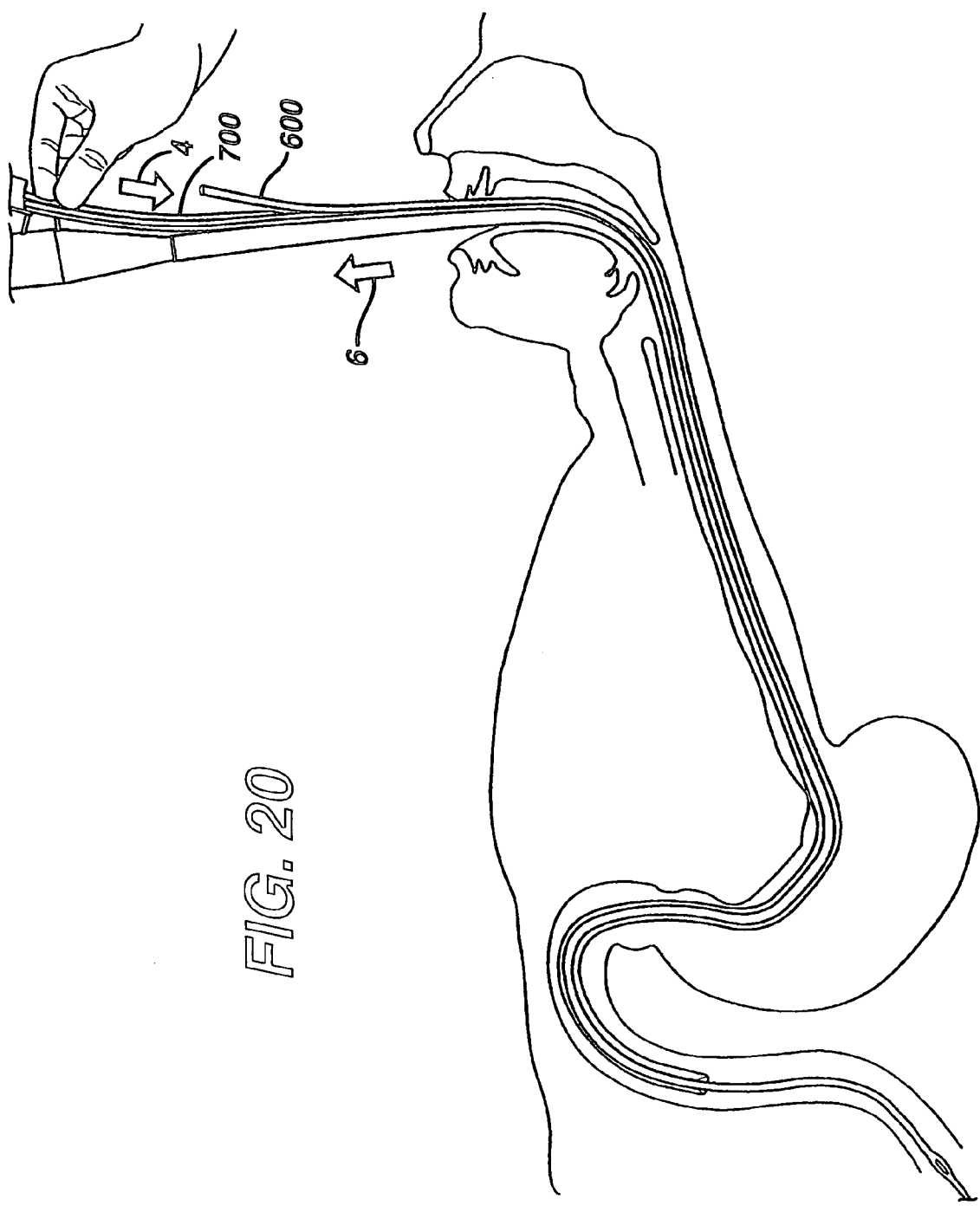
FIG. 20 illustrates feeding a member distally to a position behind the feeding tube to hold the feeding tube in place in the GI tract while the endoscope and medical device (which medical device can include a handle, sheath, endcap, and track) are removed in a proximal direction from the patient.

Referring to FIG. 20, once, the feeding tube 600 is in the desired position, the member 700 can be advanced distally (such as by hand in the direction of arrow 4) along the track 300 until the distal end 702 of the member 700 makes contact with the proximal end of the rail 666 of feeding tube 600. Then, as the member 700 is held stationary with respect to the patient's body and to the sheath assembly, the sheath assembly (with endoscope), and the carrier 500 can be withdrawn proximally from the body, in the direction indicated by arrow 6. Any tendency of the feeding tube 600 to move proximally during withdrawal of the endoscope, sheath assembly, and carrier 500 is prevented by abutting engagement of the surfaces 774 on member 700 with the surfaces 674 on the feeding tube rail 666. Accordingly, the feeding tube 600 is maintained in position by member 700 as the endoscope, the sheath assembly, and the carrier 500 are withdrawn from the body.

Figure 21:
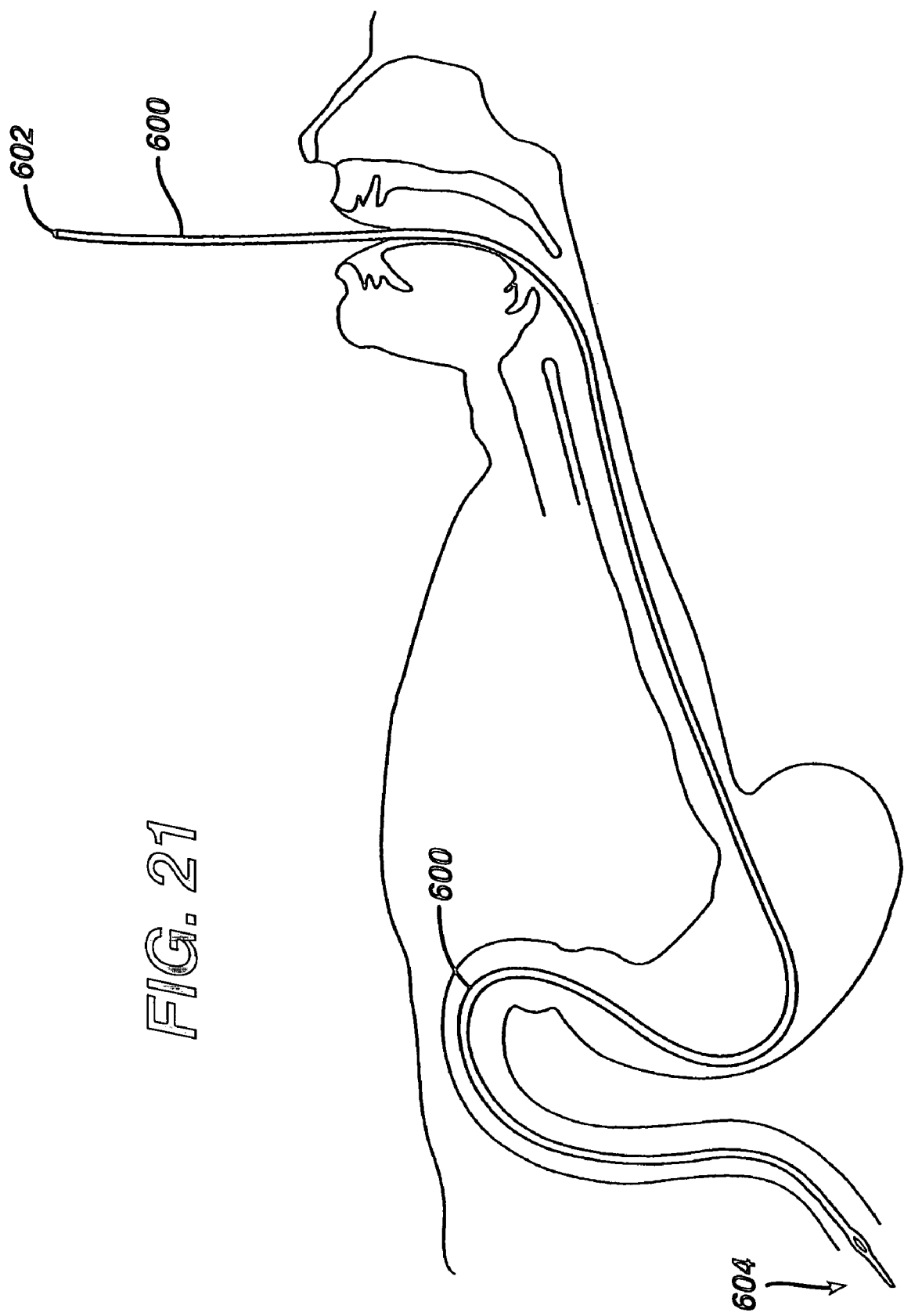
FIG. 21 illustrates the feeding tube positioned to extend from outside the mouth to the small intestine.

FIG. 21 illustrates the feeding tube in place in the patient's GI tract after removal of the endoscope, sheath assembly, and carrier 500. In FIG. 21, the feeding tube 600 extends from the feeding tube proximal end 602 (positioned outside the patient's body) to the feeding tube distal end 604 (positioned in the small intestine), with the feeding tube 600 extending through the mouth, the esophagus, the stomach, and into the small intestine.

Figure 22:
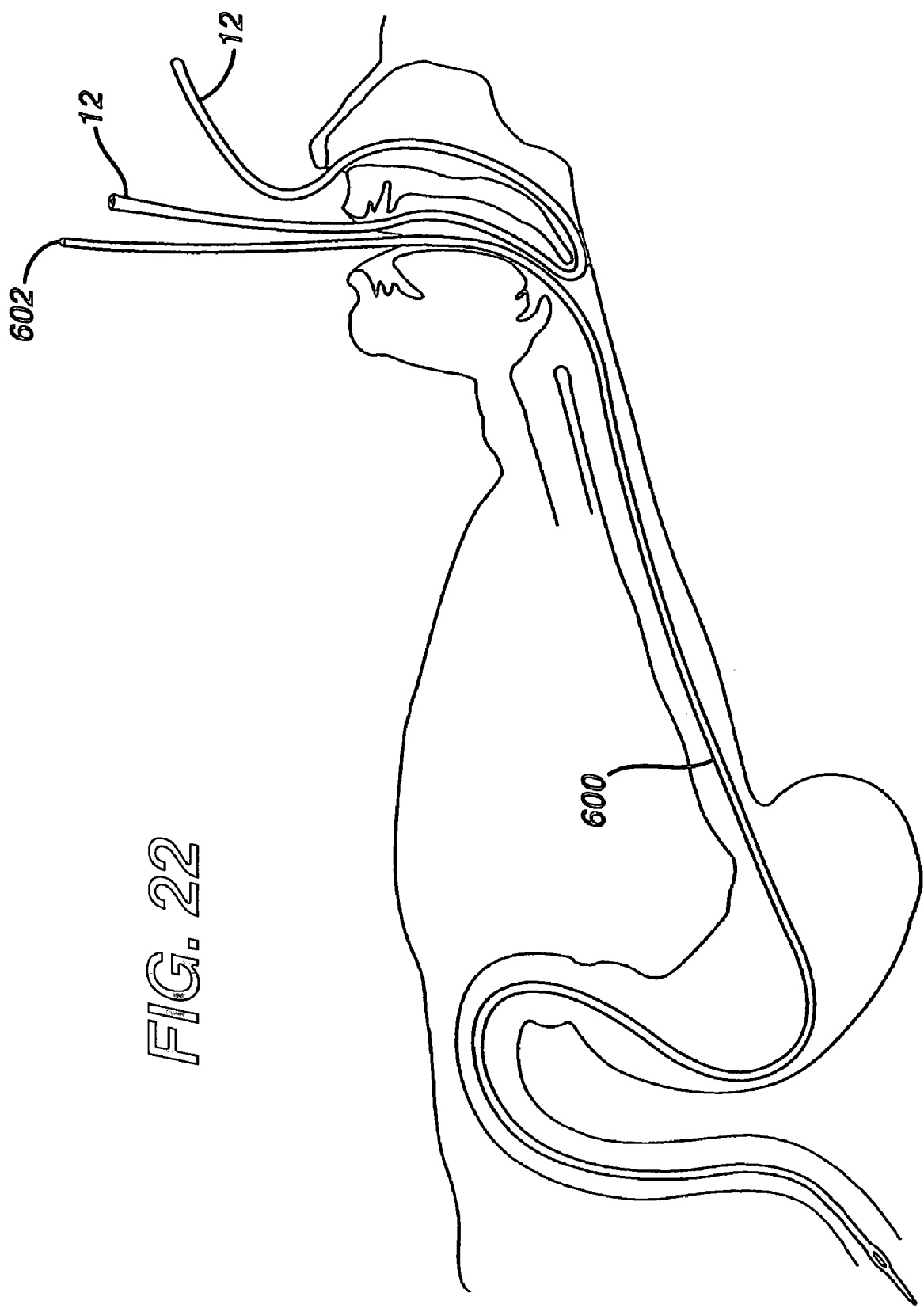
FIG. 22 illustrates providing a transfer tube through the nose.
Figure 23:
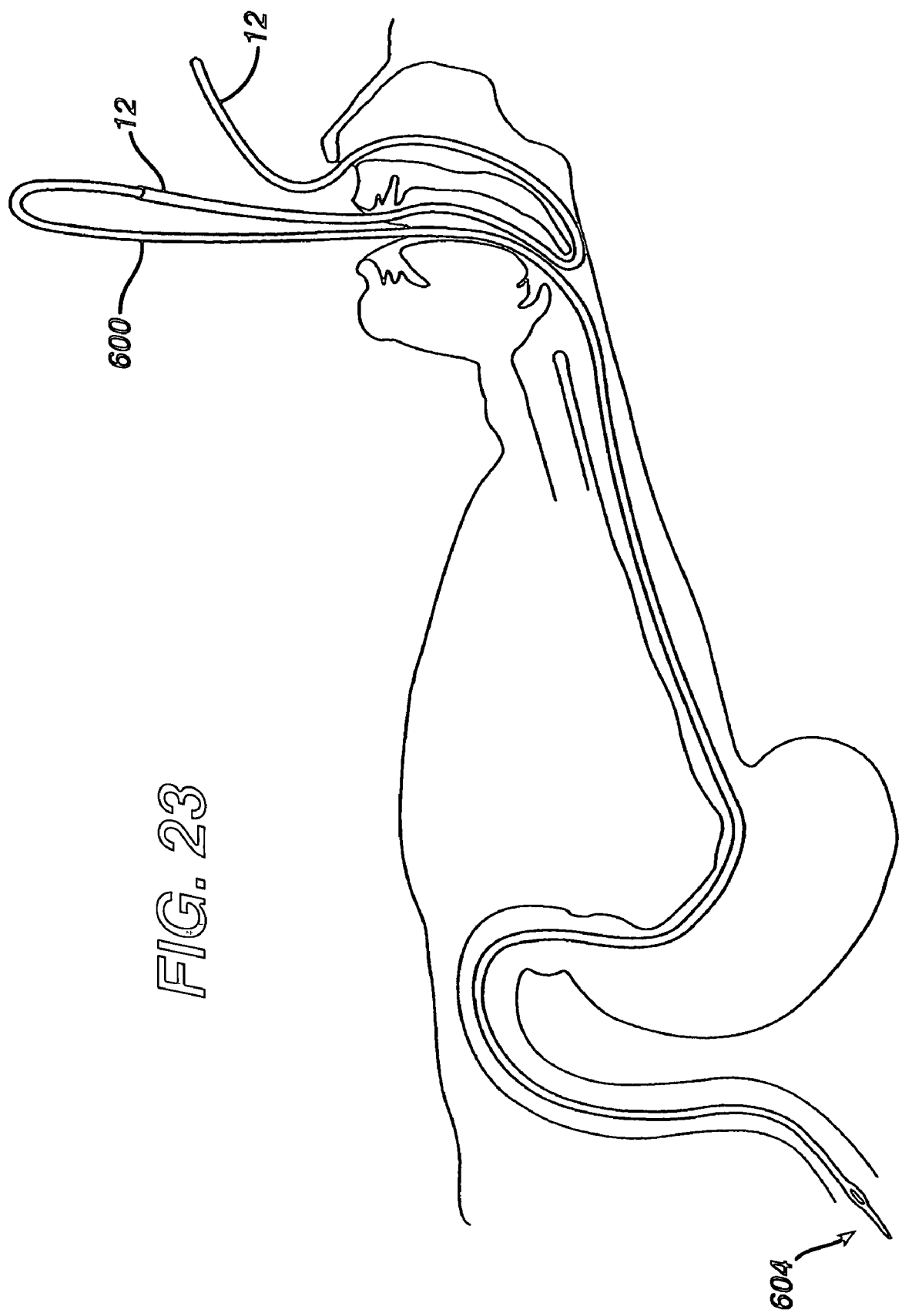
FIG. 23 illustrates associating an end of the transfer tube with the proximal end of the feeding tube.
Figure 24:
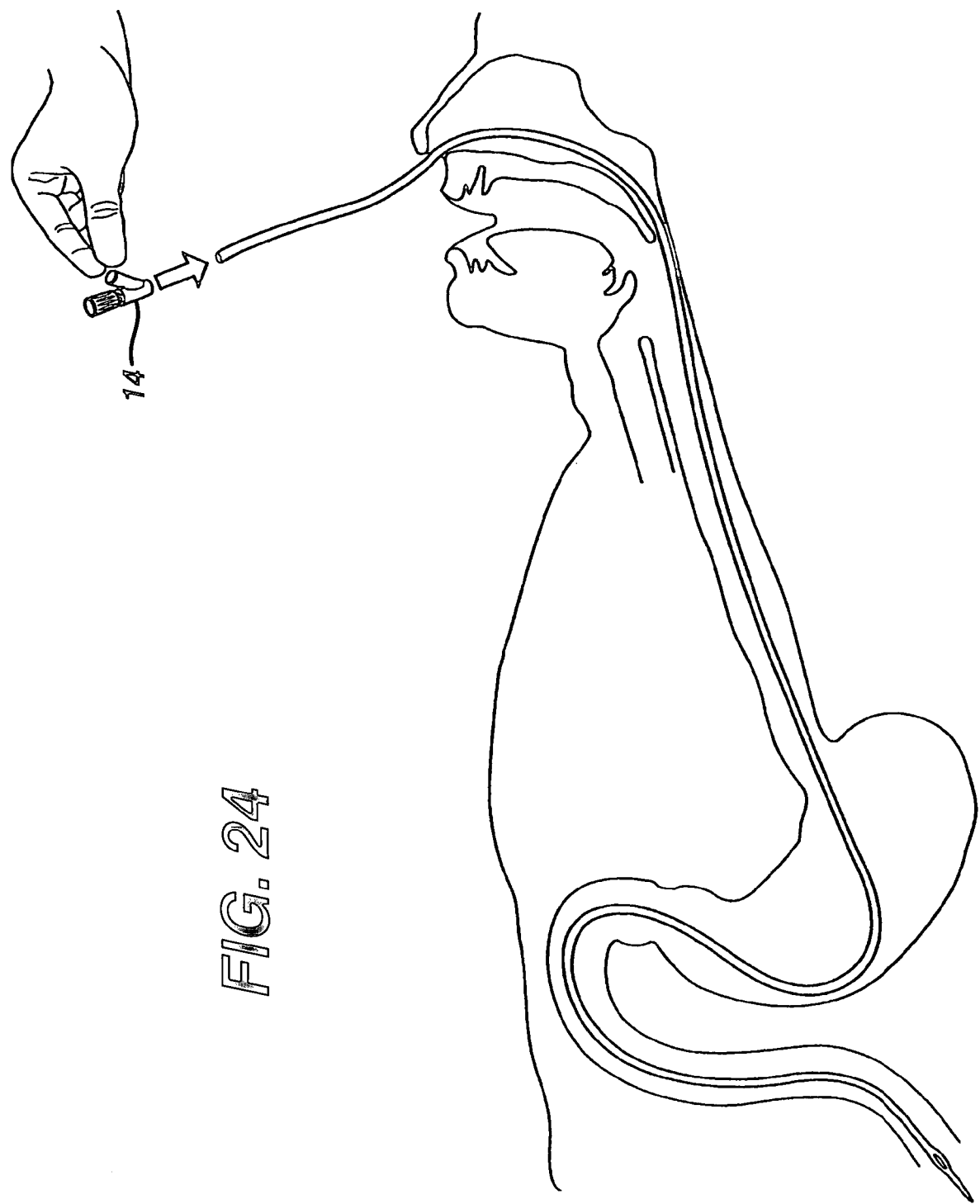
FIG. 24 illustrates the proximal end of the feeding tube pulled through the throat and the nasal cavity (such as with the transfer tube of FIG. 23) such that the proximal end of the feeding tube extends from the patient's nose (from a nostril).

If desired, the feeding tube can be used in the position shown in FIG. 21. However, it may generally be desirable to have the proximal end of the feeding tube extending from the nose. FIG. 22 illustrates use of a transfer tube 12 which may be inserted to extend from the mouth and the nose. The end of the transfer tube extending from the mouth can be coupled to the proximal end 602 of the feeding tube, as shown in FIG. 23. The end of the transfer tube 12 extending from the nose can then be pulled so that the proximal end 602 of the feeding tube is redirected to extend from the nose, as shown in FIG. 24. A suitable fitting 14 can then be attached to the proximal end 602 of the feeding tube, as shown in FIG. 24.

Figure 25:
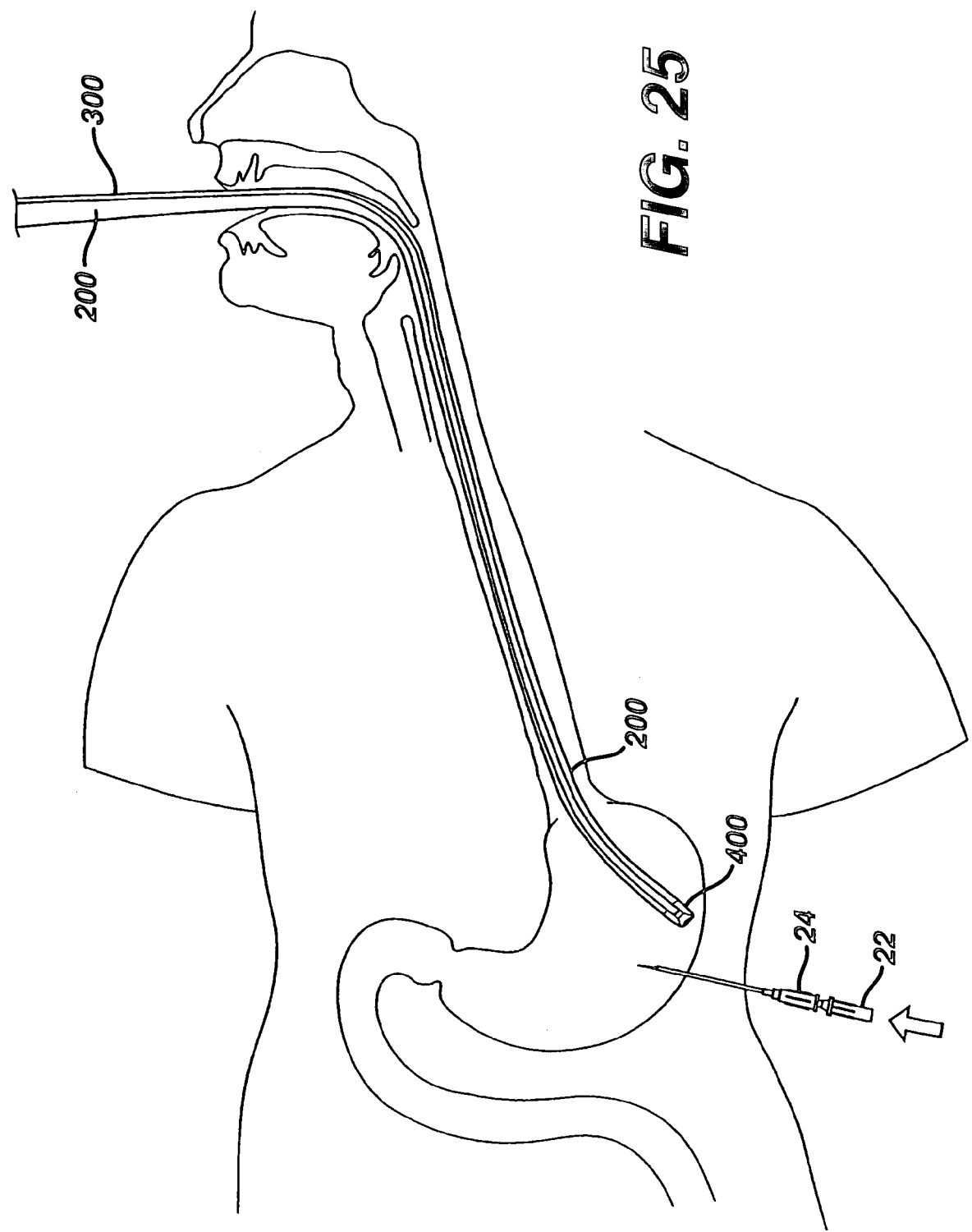
FIG. 25 illustrates positioning an endoscope within a medical device (which medical device can include a handle, sheath, endcap, and track) into the GI tract such that the endcap and the distal end of the track are disposed in the stomach, such as for use in a PEG tube feeding method, and FIG. 25 illustrating a cannula/needle for providing a percutaneous incision through the abdominal wall can be transilluminated with a light source associated with the endoscope.

FIGS. 25-30 illustrate an alternative method for positioning a feeding tube within a patient for providing feeding access through an incision in the patient's abdominal wall. FIGS. 25-30 illustrate a method of placing a feeding tube in the stomach as an alternative to standard PEG procedures. Referring first to FIG. 25, the endoscope disposed within the sheath assembly comprising the handle 100, sheath 200 and endcap 400 can be advanced through the mouth to position the distal end of the endoscope and the endcap 400 within the stomach of the patient. A light source (such as a light source associated with the distal end of the endoscope) can be employed from within the stomach to transilluminate the abdominal wall, so that the position of the endoscope within the stomach can be observed from outside the patient. A small, percutaneous incision can be made through the abdominal wall, and a needle 22/cannula 24, such as a 14 gauge needle 22/cannula 24 can be inserted through the incision so that the distal tip of the needle and the distal end of the cannula can be positioned within the stomach.

Figure 26:
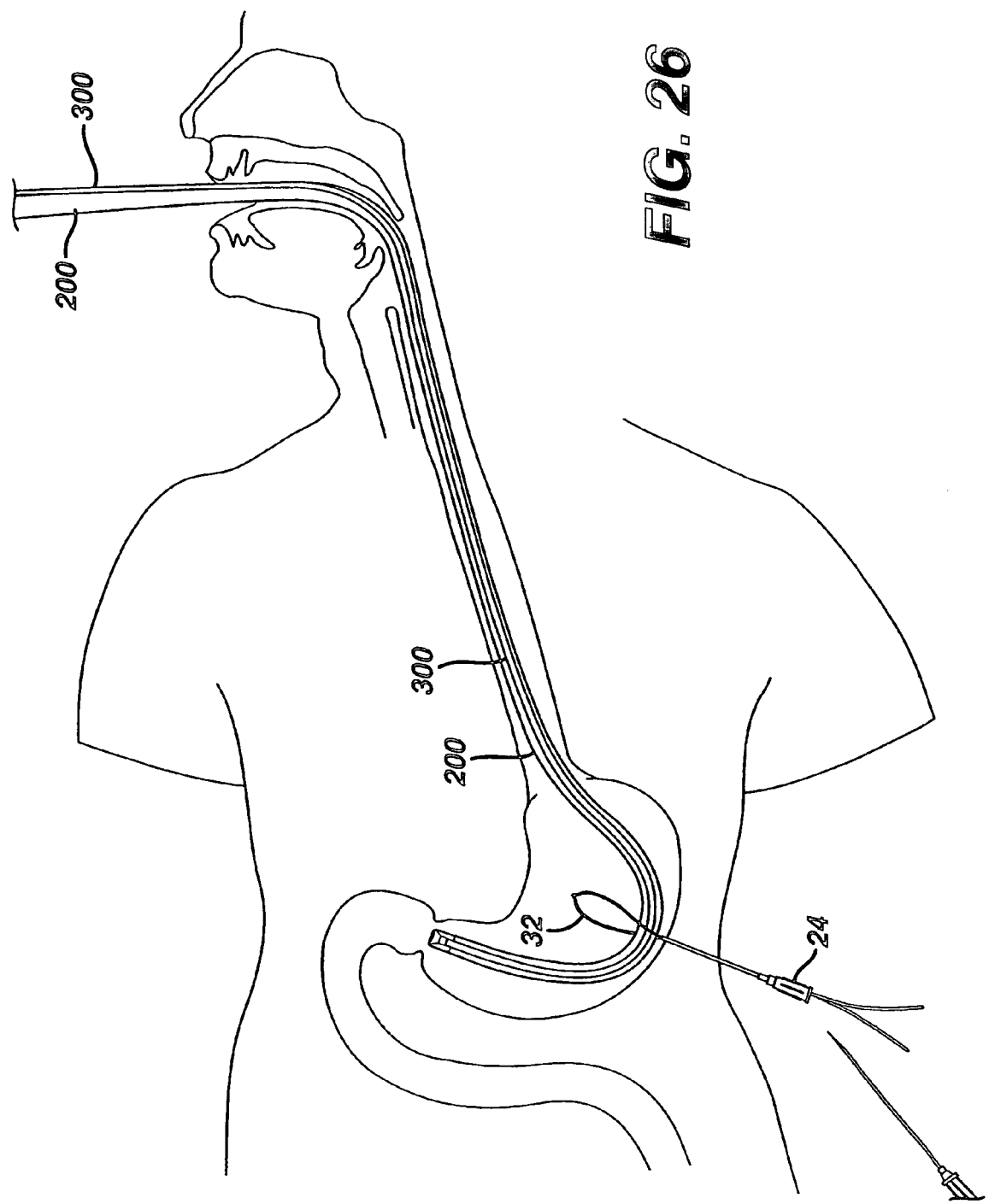
FIG. 26 illustrates removing the needle from the cannula and introducing a looped guidewire through the cannula, and illustrating the distal end of the endoscope, endcap, sheath, and track passing through the loop of the looped guidewire.

Referring to FIG. 26, the needle 22 can be withdrawn, leaving the cannula 24 to provide an access channel extending from inside the stomach to a point outside the patient. A looped guide wire 32 can be passed through the cannula, and the endoscope and sheath assembly can be directed to extend through the loop provided by the guide wire 32.

Figure 27:
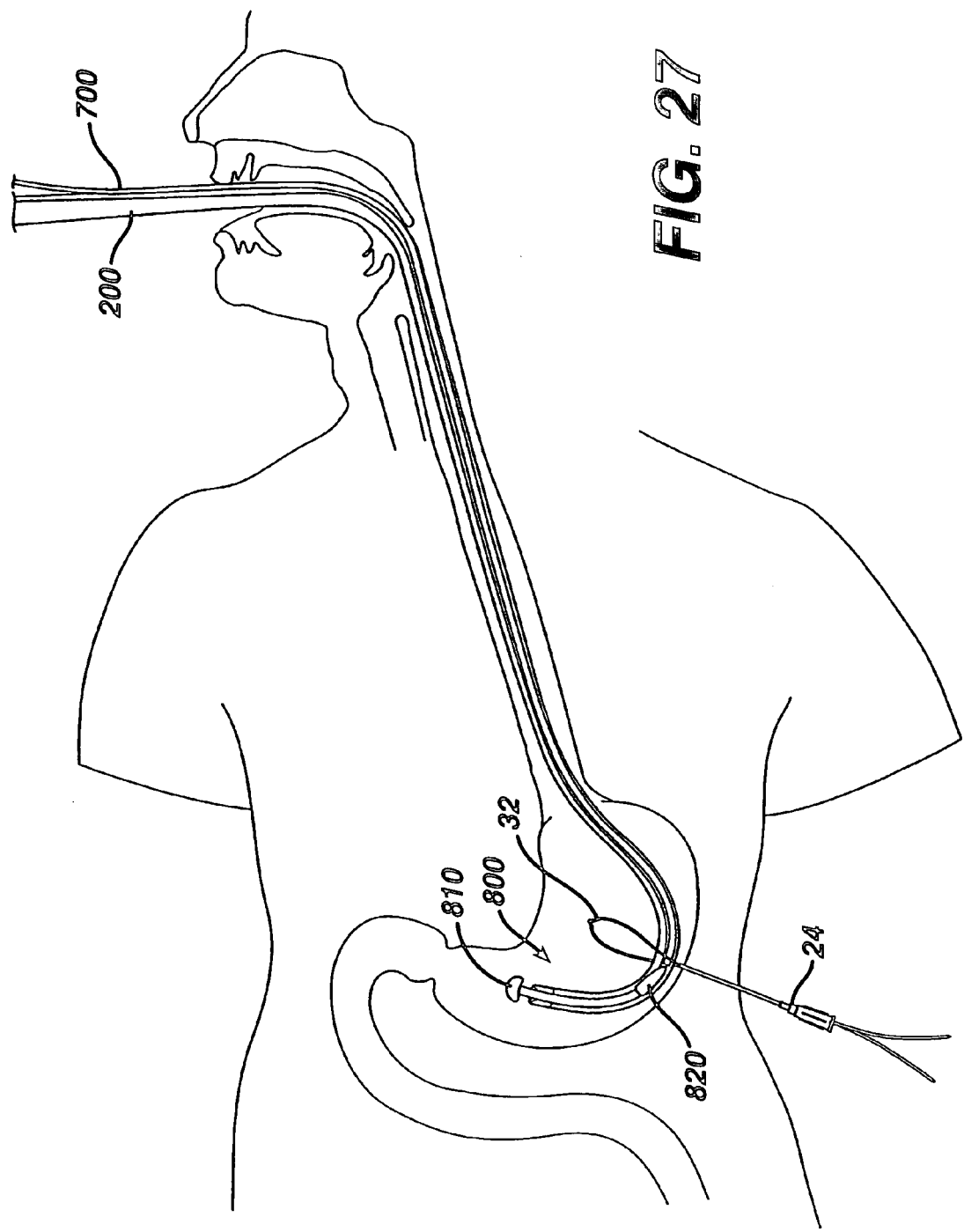
FIG. 27 advancing a PEG tube (such as a PEG tube having a length substantially less than the length of the track) on the track, with the PEG tube disposed on the track such that a first end of the PEG tube to be positioned inside the body is advanced ahead of a second end of the PEG to be positioned through the percutaneous incision, and showing the first end of the PEG tube being advanced off of the track.

Referring to FIG. 27, a relatively short feeding tube 800 is illustrated, the feeding tube having a length substantially less than the length of the track 300. Feeding tube 800 in this embodiment can have a length of less than about 3 feet. The feeding tube 800 can be a commercially available PEG type feeding tube modified to have a feature, such as a rail (not shown), for permitting the feeding tube 800 to slidably engage the track 300 and/or carrier 500. For instance, the feeding tube 800 can be formed by attaching a web and rail to a commercially available PEG feeding tube, such as by bonding or otherwise attaching the web and rail to the feeding tube (alternatively, the feeding tube 800 could be formed by extruding or otherwise forming a feeding tube to have an integral web and rail feature). One suitable commercially available PEG type feeding tube from which feeding tube 800 can be constructed is available from Viasys Healthcare of Wheeling, Ill. as marketed in a Corflo-Max brand PEG kit for use with a Push Technique or Pull Technique. The feeding tube 800 can include a sealing bumper or bolster 810 and a tapered dilating tip 820.

Referring to FIG. 27, with the sheath assembly extending through the loop provided by guide wire 32, the feeding tube 800 can advanced distally along the sheath assembly and into the stomach. The feeding tube 800 can be positioned on track 300 and advanced distally along track 300 to the stomach by using member 700 as a pushing element. Alternatively, the feeding tube can be disposed on carrier 500, and the carrier 500 with feeding tube 800 can be advanced along track 300 to the stomach.

Figure 28:
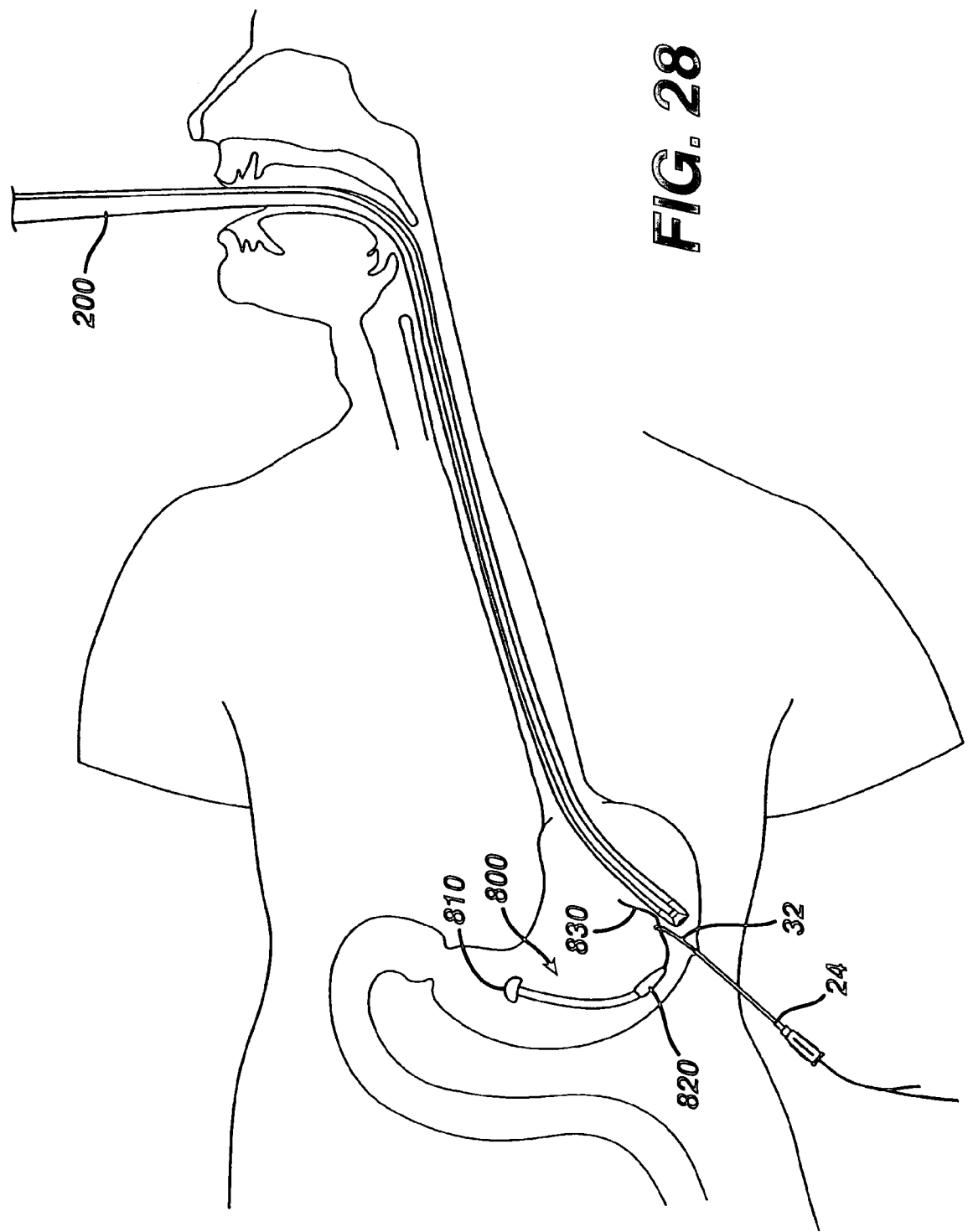
FIG. 28 illustrates the second end of the PEG tube advanced off of the rail and grasping a length of suture extending from the second end of the PEG tube with the looped guidewire.

Referring to FIG. 28, the feeding tube 800 can be pushed off the distal end of the sheath assembly using a member, such as a member 700 described above. As the feeding tube 800 is pushed off the sheath assembly, a suture 830 (or other suitable flexible wire or tether) that extends from the tip 820 can be grasped with the guidewire 32 so that the suture 830 can be pulled through cannula 24.

Figure 29:
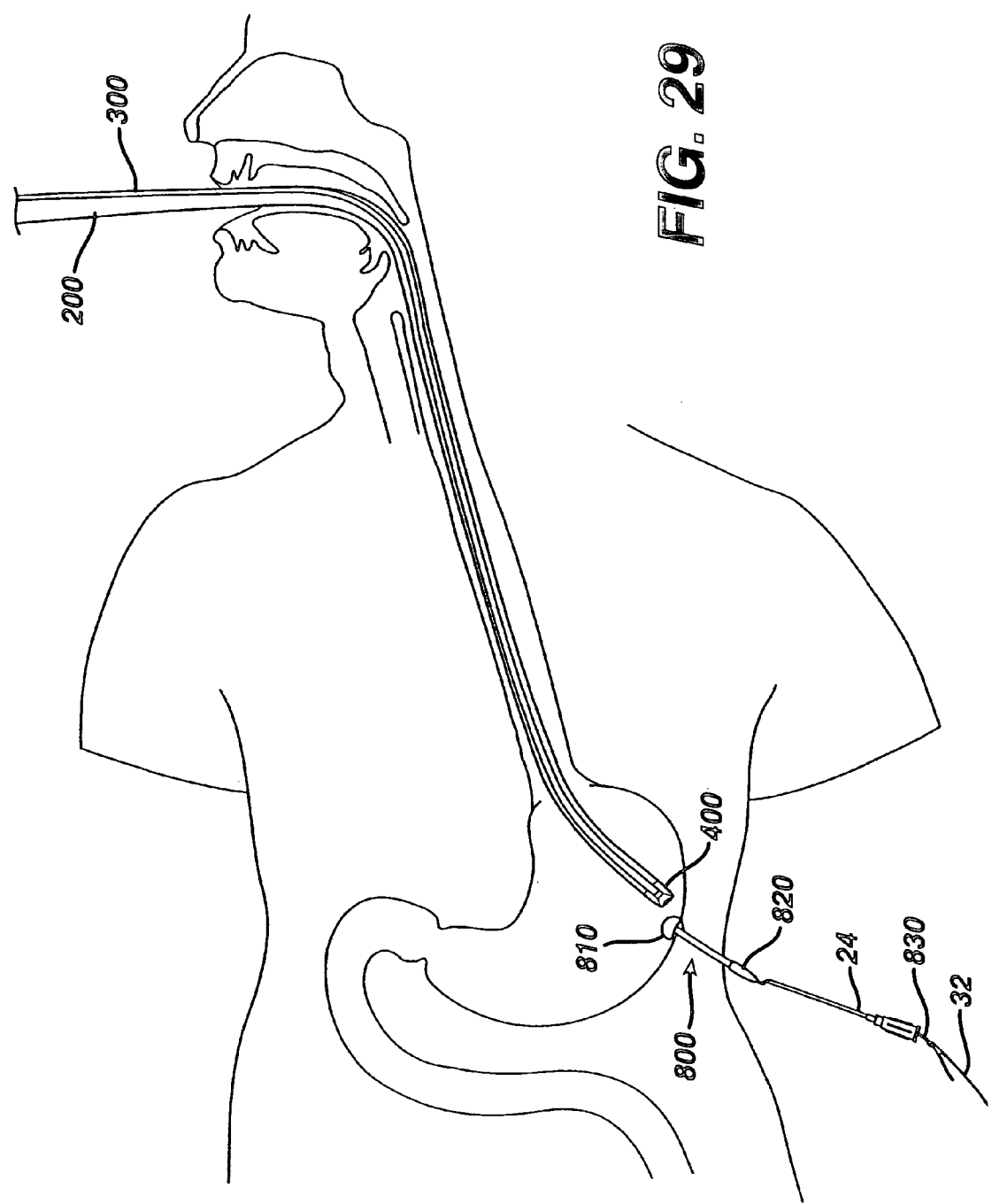
FIG. 29 illustrates pulling the suture loop and the second end of the PEG tube through the percutaneous incision and seating a bumper member at the first end of the PEG tube against the inside surface of the gastric wall, with the endoscope positioned to provide viewing of the seating.

Referring to FIG. 29, the suture 830 can be pulled (such as with forceps or a hemostat) so that tip 820 extends through the percutaneous incision through the abdominal wall and such that the sealing bumper 810 is positioned against the inside surface of gastric wall (inside surface of the stomach).

Figure 30:
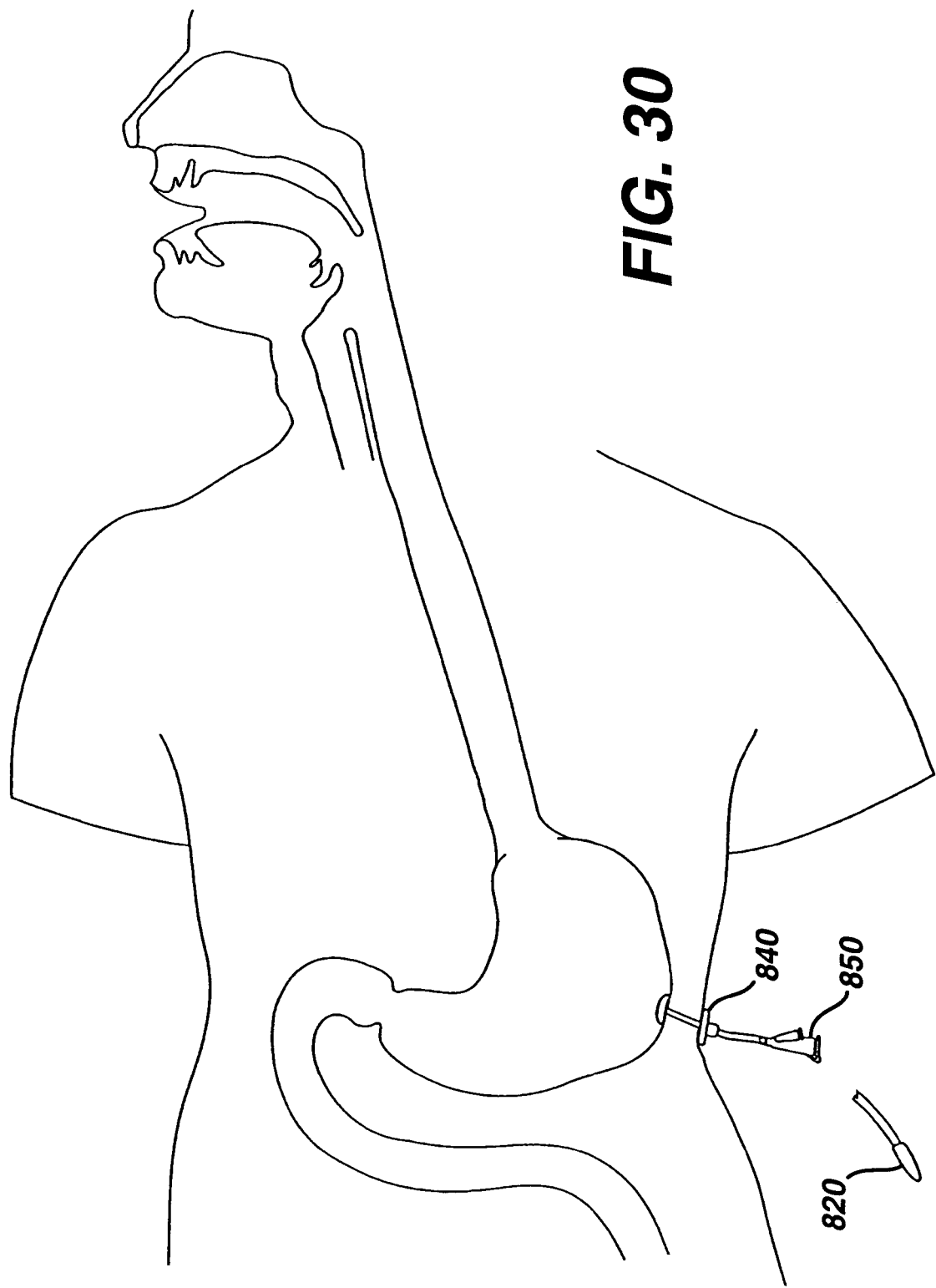
FIG. 30 illustrates the medical device and endoscope removed from the GI tract and the external portion of the PEG tube adapted for introducing nutrients through the abodiminal wall.

Referring to FIG. 30, the sheath assembly can be removed from the patient, and an external seal 840 can be advanced over the feeding tube 800 to fit against the patients skin adjacent the incision. The feeding tube 800 can be cut to sever the tip 820 from the feeding tube, and a fitting 850 can be positioned on the end of the feeding tube external of the patient. In the procedure illustrated in FIGS. 25-30, a feeding tube is introduced into the patient through a naturally occurring orifice and pushed distally along an endoscope after the endoscope has been positioned in the stomach. The feeding tube is then pulled through an incision to provide a feeding access channel that extends through an incision to the patient's GI tract.

FIGS. 31-37 illustrate steps which can be employed in a method for positioning a feeding tube according to another embodiment of the present invention. FIGS. 25-30 illustrate a method of placing a feeding tube in the small intestine as an alternative to standard JET-PEG type procedures.

Figure 31:
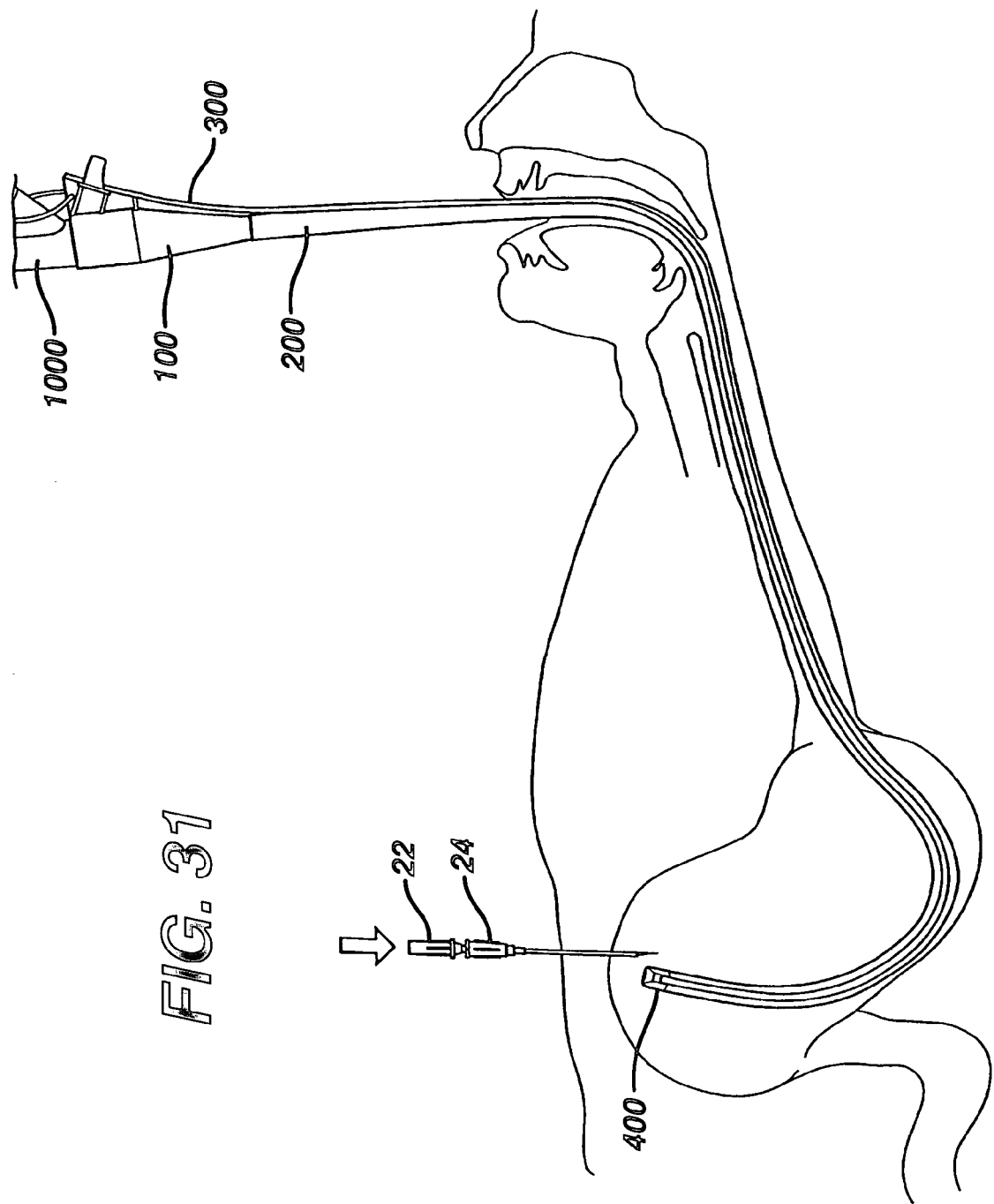
FIG. 31 illustrates positioning an endoscope (such as a gastroscope) disposed in a medical device (which medical device can include a handle, sheath, endcap, and track) into the GI tract such that the endcap, the distal end of the gastroscope, and the distal end of the track are disposed in the stomach, such as for use in a JET-PEG tube feeding method, with FIG. 31 also showing the endoscope can be used to transilluminate the abdominal wall, such that a needle/cannula can be used to make and/or pass through a small incision into the stomach.

Referring first to FIG. 31, the endoscope 1000 disposed within the sheath assembly comprising the handle 100, sheath 200 and endcap 400 can be advanced through the mouth to position the distal end of the endoscope and the endcap 400 within the stomach of the patient. A light source (such as a light source associated with the distal end of the endoscope) can be employed from within the stomach to transilluminate the abdominal wall, so that the position of the endoscope within the stomach can be observed from outside the patient. A small, percutaneous incision can be made through the abdominal wall, and a needle 22/cannula 24, such as a 14 gauge needle 22/cannula 24 can be inserted through the incision so that the distal tip of the needle and the distal end of the cannula can be positioned within the stomach.

Figure 32:
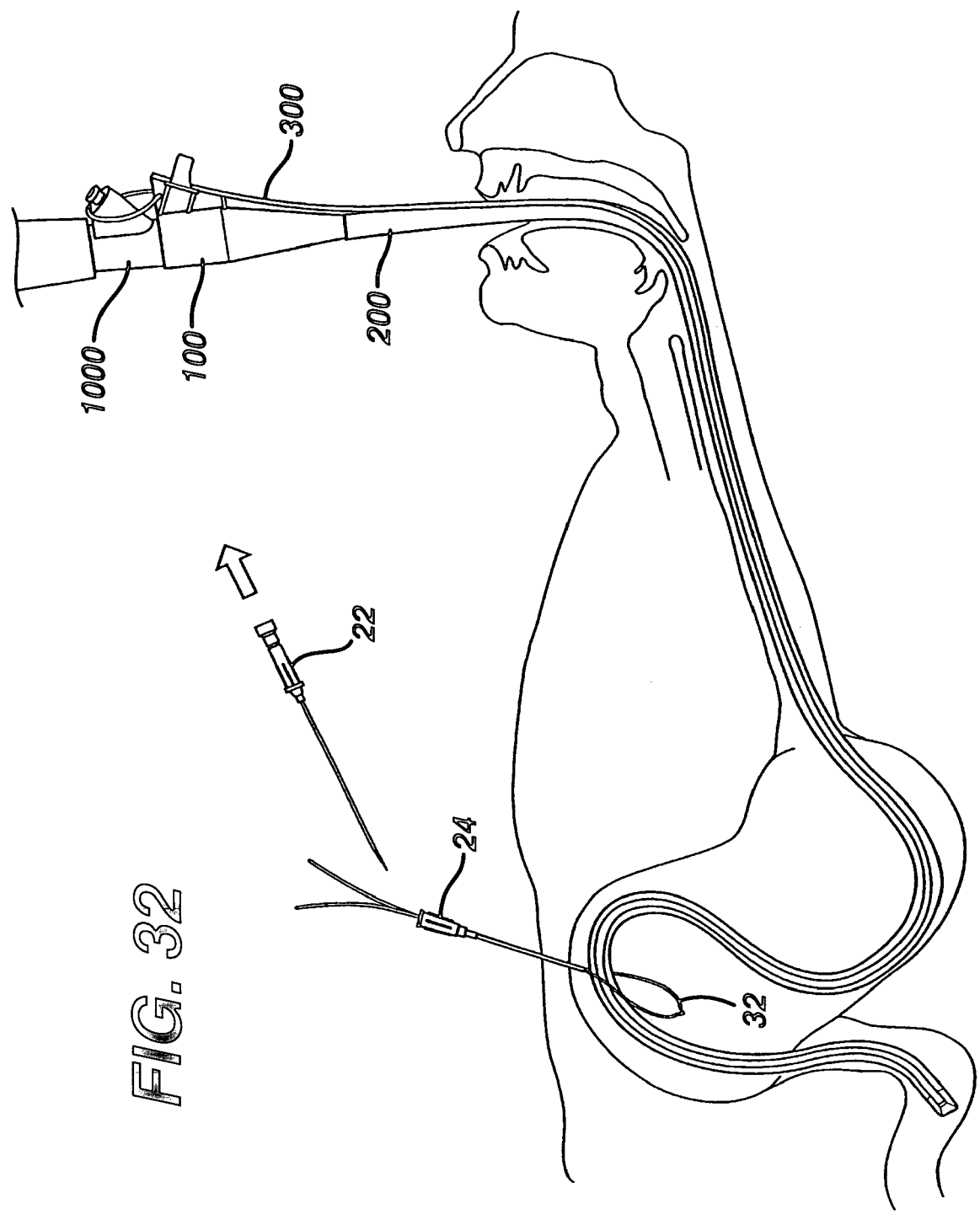
FIG. 32 illustrates removing the needle and introducing a looped guidewire through the cannula, after which the medical device (with gastroscope disposed therein) can be advanced through the looped guidewire, with the distal end of the medical device and the distal end of the gastroscope being advanced into the jejunum (such as past the Ligament of Treitz)

Referring to FIG. 32, the needle 22 can be withdrawn, leaving the cannula 24 to provide an access channel extending from inside the stomach to a point outside the patient. A looped guide wire 32 can be passed through the cannula, and the endoscope and sheath assembly can be directed to extend through the loop provided by the guide wire 32. The endoscope and sheath assembly can be advanced distally from the stomach into the small intestine, as shown in FIG. 32.

Figure 33:
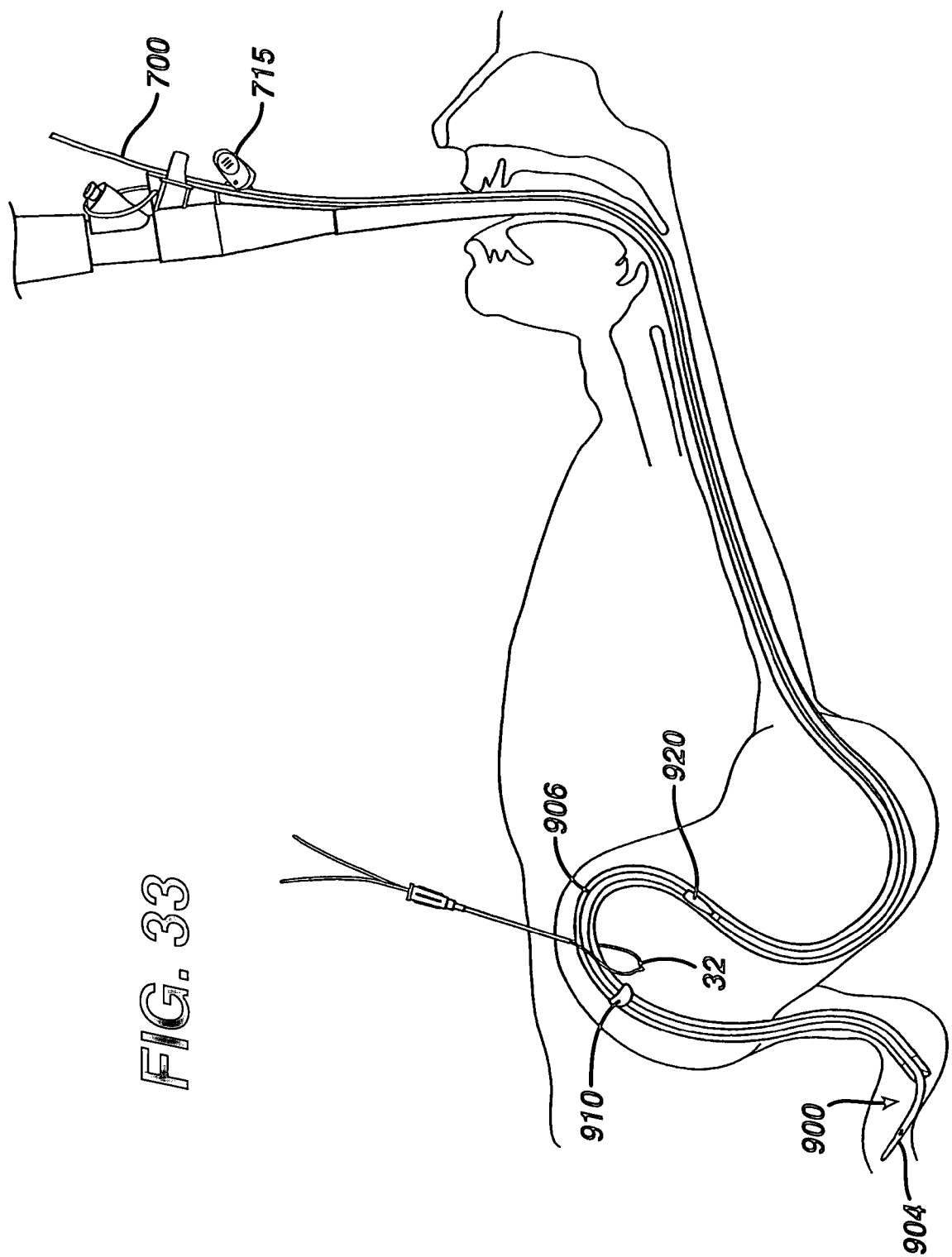
FIG. 33 illustrates positioning a feeding tube (such as a feeding tube having a length substantially less than the length of the track) and carrier on the track, and advancing the feeding tube along the track until the distal end of the feeding tube is positioned in the jejunum and can be viewed by the endoscope.

Referring to FIG. 33, a feeding tube 900 can be advanced along the length of the sheath assembly such that the feeding tube 900 passes through the loop provided by guidewire 32. The feeding tube 900 shown in FIG. 3 can include a distal portion 904 having a construction like that of the feeding tube 600 described above, and a proximal portion 906 having a construction similar to that of the feeding tube 800 described above. The proximal portion 906 can include a tapered dilating tip 920 and a bumper or bolster 910. The proximal portion 906 can be constructed using a PEG feeding tube of the type provided in Corflo-Max brand PEG Kits for Pull Technique or Push Technique, which kits are available from Viasys Healthcare of Wheeling, Ill.

The opening through which food is delivered to the GI tract can be located in the distal portion 904. The feeding tube 900 can include a feature, such as a rail (such as the type shown in FIGS. 10, 11, and 13) on one or both of the portions 904 and 906 such that feeding tube can slidably engage the track 300 and/or the carrier 500. In one embodiment, the feeding tube 900 is positioned on the carrier 500 outside of the patient's body, and the feeding tube 900 and carrier are advanced together along track 300. The positioning member 700 can be advanced along carrier 500 behind feeding tube 900. If desired, the positioning member 700 can include a grasping clip 715 which can clip onto or otherwise be fastened to member 700 to assist in grasping and pushing the member 700 along carrier 500.

Figure 34:
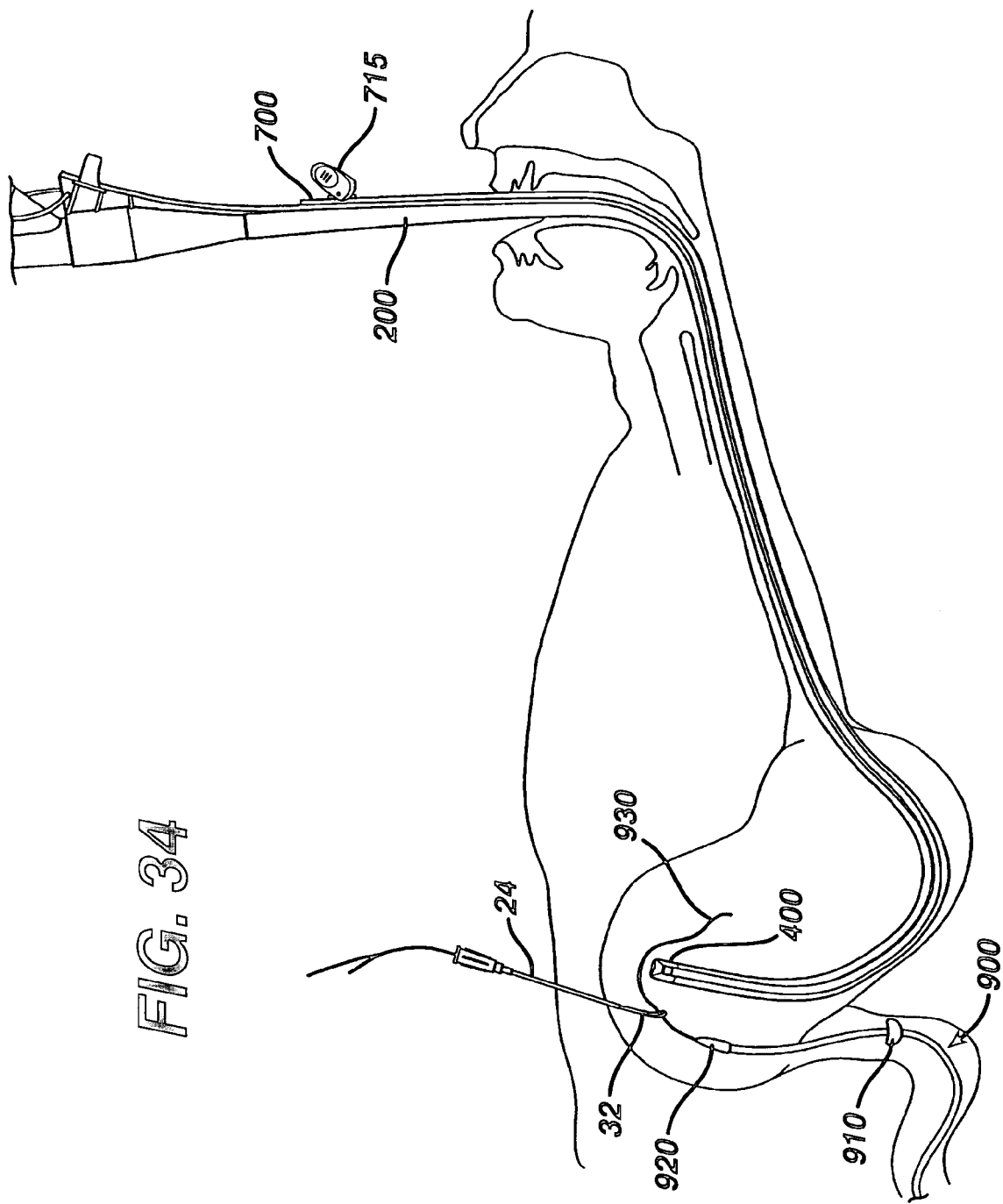
FIG. 34 illustrates retracting the medical device and gastroscope proximally into the stomach, while holding a member positioned proximally behind the feeding tube to push the feeding tube off the distal end of the track, and illustrating grasping a length of suture extending from the feeding tube with the looped guidewire.

Referring to FIG. 34, with the positioning member 700 held in position, the endoscope and sheath assembly can be retracted proximally from the stomach, such that the feeding tube 900 is pushed off the end of the sheath assembly by positioning member 700 as the endoscope and sheath assembly are retracted. A length of suture 930 extending from the tip 920 can be grasped using the looped guide wire 32.

Figure 35:
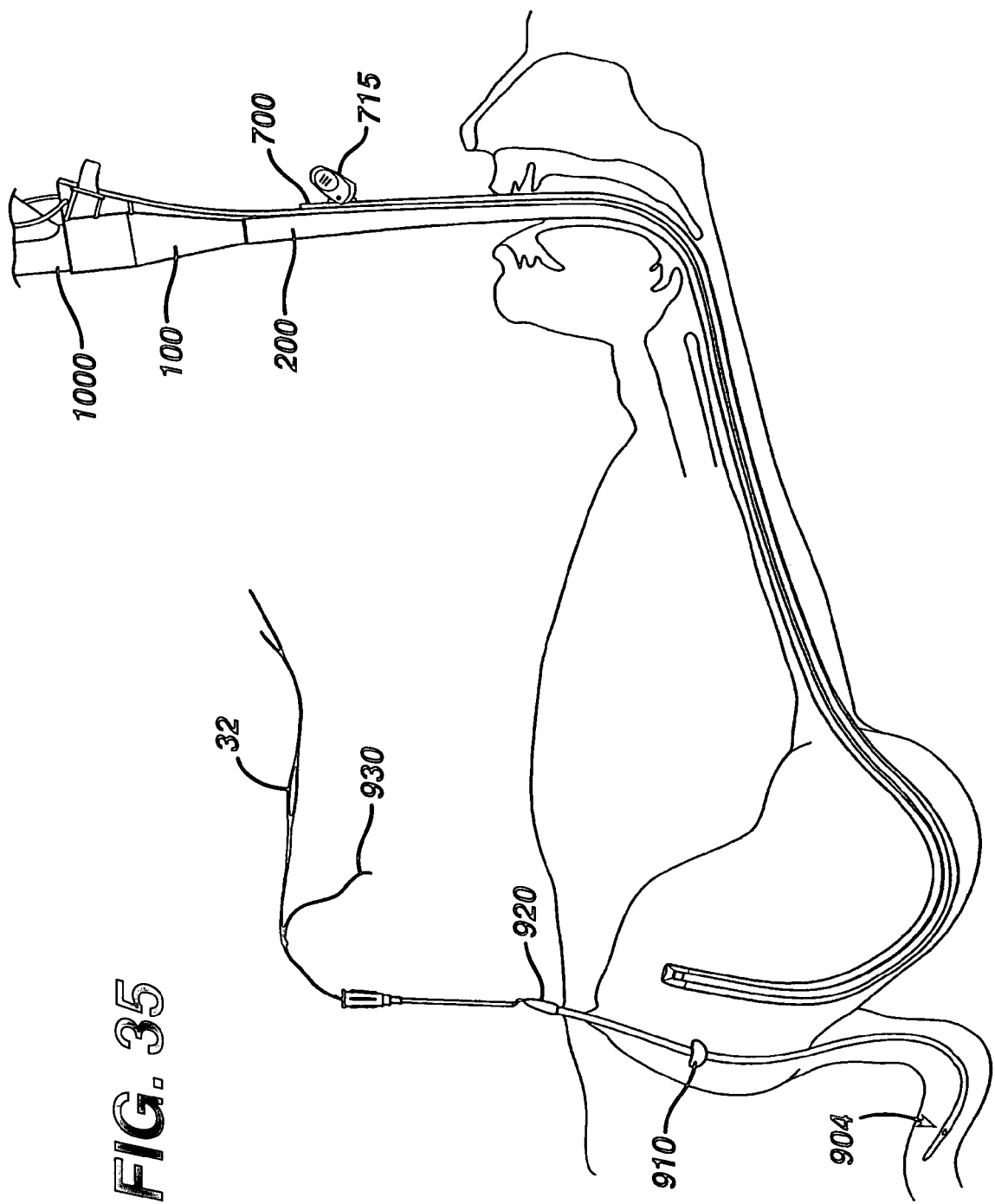
FIG. 35 illustrates pulling the suture and an end of the feeding tube through the incision through the abodiminal wall, and leaving a distal end of the feeding tube in the jejunum.
Figure 36:
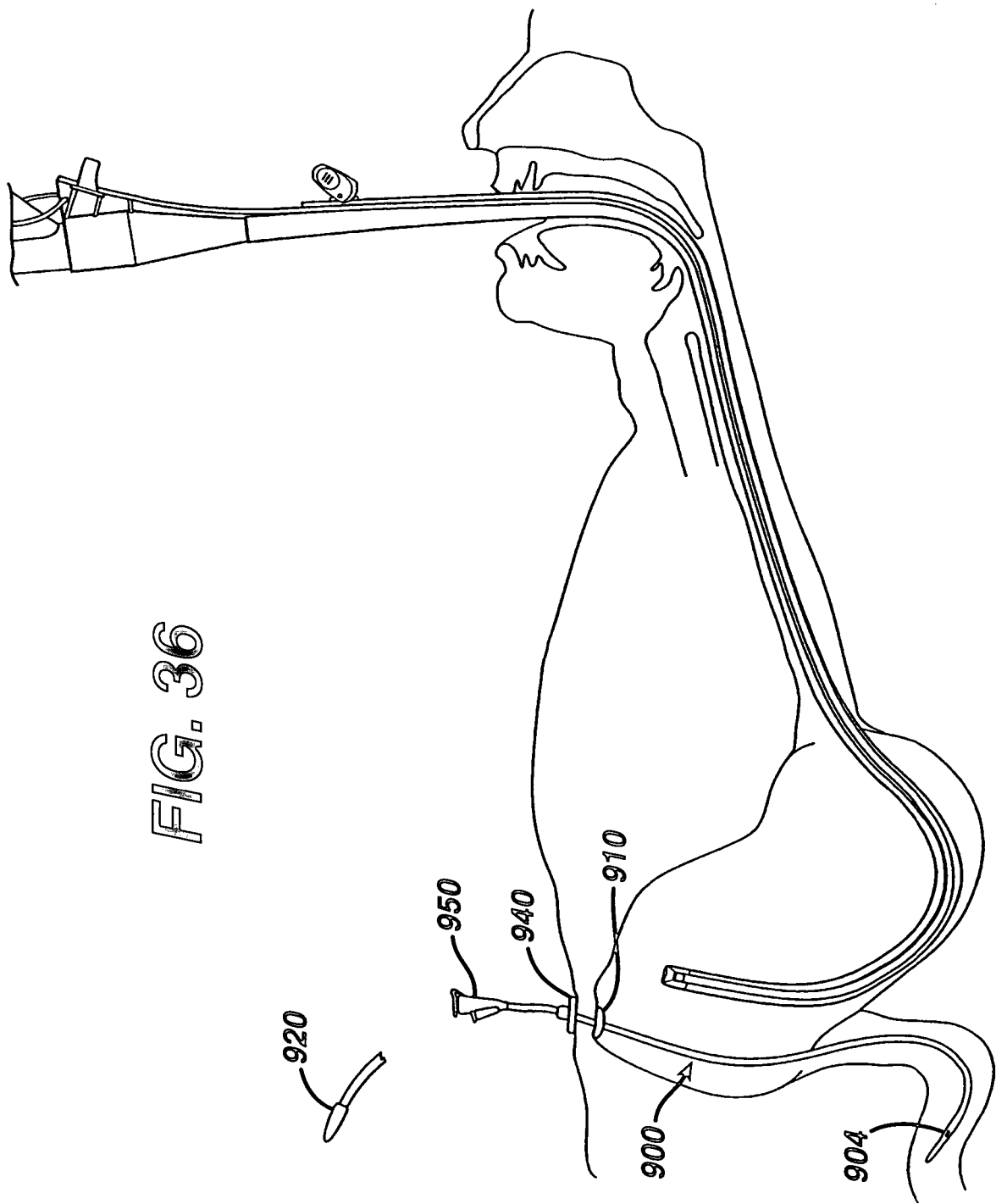
FIG. 36 illustrates the external portion of the feeding tube adapted for introducing nutrients through the abodiminal wall, with the distal end of the feeding tube being positioned in the jejunum.
Figure 37:
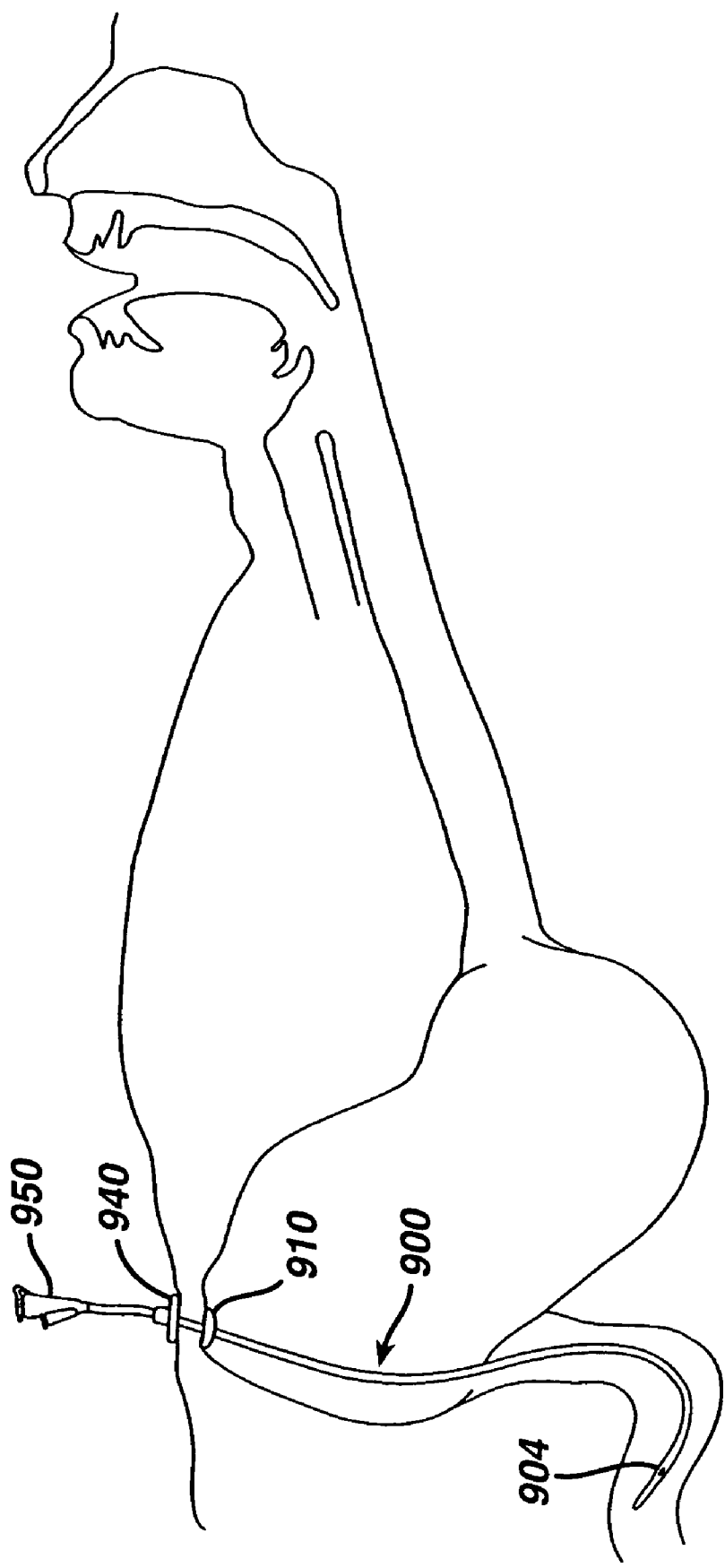
FIG. 37 illustrates the feeding tube in place with the gastroscope and medical device removed.

Referring to FIG. 35, the suture 930 and tip 920 can be pulled through the incision until bumper 910 is positioned against the inside surface of the stomach, with the portion 904 of the feeding tube including the port through which food is provided being positioned in the small intestine (such as the jejunum). Referring to FIG. 36 an external seal 940 can be advanced over the feeding tube 900 to fit against the patients skin adjacent the incision. The feeding tube 900 can be cut to sever the tip 920 from the feeding tube, along with any unneeded length of the tube, and a fitting 950 can be positioned on the end of the feeding tube external of the patient. In FIG. 37, the endoscope and sheath assembly are shown removed from the patient's body, and the feeding tube 900 is shown positioned with the distal portion 904 disposed in the small intestine, and with the feeding tube 900 extending from the small intestine through the stomach to pass through an incision through the stomach and through the patient's abdominal wall and skin.

In the procedure illustrated in FIGS. 31-37, a feeding tube is introduced into the patient through a naturally occurring orifice and pushed distally along an endoscope after the endoscope has been positioned in the stomach. The feeding tube is then pulled through an incision to provide a feeding access channel that extends through a percutaneous incision into the patient's GI tract (eg. small intestine).

FIGS. 38-42 illustrate a method for positioning and endcap 400 (such as an elastomeric endcap 400) and sheath 200 on an endoscope 1000 prior to inserting the endoscope on the sheath assembly into the patient. In some applications, it may be difficult to manually load an endoscope into a sheath having an endcap, such as by gripping the components by hand. For instance, it may be difficult to grip the endoscope through the sheath and apply the appropriate force to urge the endcap to fit over the distal end of the endoscope. Additionally, it may be desirable to maintain a certain angular "o'clock" orientation of the endcap with respect to the endoscope. In the course of applying the force to urge the endcap onto the endoscope, the desired o'clock orientation may be inadvertently lost, requiring re-installation. The method and components illustrated in FIGS. 38-42 can be employed to assist in proper installation of an endcap (and associated sheath and track) onto an endoscope. Additionally, the method and components can be employed to install an endcap on an endoscope even if no sheath and or track is employed.

Referring to FIG. 38, an endcap loading element is shown in the form of a nose cone 2100. The nose cone 2100 can be disposable, and can be formed of a lightweight material, such as a polymeric material. The nose cone 2100 can include a body portion 2110 and a plurality of flexible prongs 2120 (six prongs shown in FIG. 38). The distal end 2102 of the body portion 2110 can be rounded or tapered. The body portion 2110 can include a through hole 2112 which extends through the width of body portion 2110 in a direction transverse to the longitudinal axis of the body portion 2110. The body portion 2110 and the prongs 2120 can be sized and shaped to pass through the central bore opening 420 of endcap 400.

The body portion 2110 can include a plurality of radial splines 2114 which extend along the length of body portion 2110. Each spline 2114 can be associated with a rounded or sloped prong shoulder 2118. Each prong shoulder 2118 can be associated with a flexible prong 2120. Each flexible prong 2120 can extend proximally from a prong shoulder 2118 to a proximal prong end 2122. Each rounded prong shoulder 2118 can extending radially outward from its associated spline 2114 on the body portion 2110 to the flexible prong 2120 associated with that prong shoulder.

The radially outward surfaces of the splines 2114 can define a first diameter of the nose cone 2100, and the radially outward surfaces of the prongs 2120 can define a second diameter of the nose cone, with the second diameter being greater than the first diameter. The radially outer surface of each rounded prong shoulder 2118 can be shaped to provide a smooth radial transition from each spline to its associated prong. Accordingly, the rounded prong shoulders 2118, together, provide a smooth radial transition from the first diameter to the second diameter. The radially inward facing surfaces of the flexible prongs 2120 can be spaced apart (either by being formed in that fashion, or due to an applied force) to receive the distal end of the endoscope 1000.

The splines 2114, rounded prong shoulders 2118, and the prongs 2120 can be circumferentially spaced apart at generally equal angular intervals (e.g. for six splines, six prong shoulders, and six prongs, each associated spline, prong shoulder, flexible prong could be spaced at 60 degree intervals about the circumference of the body portion 2110).

Figure 40A:
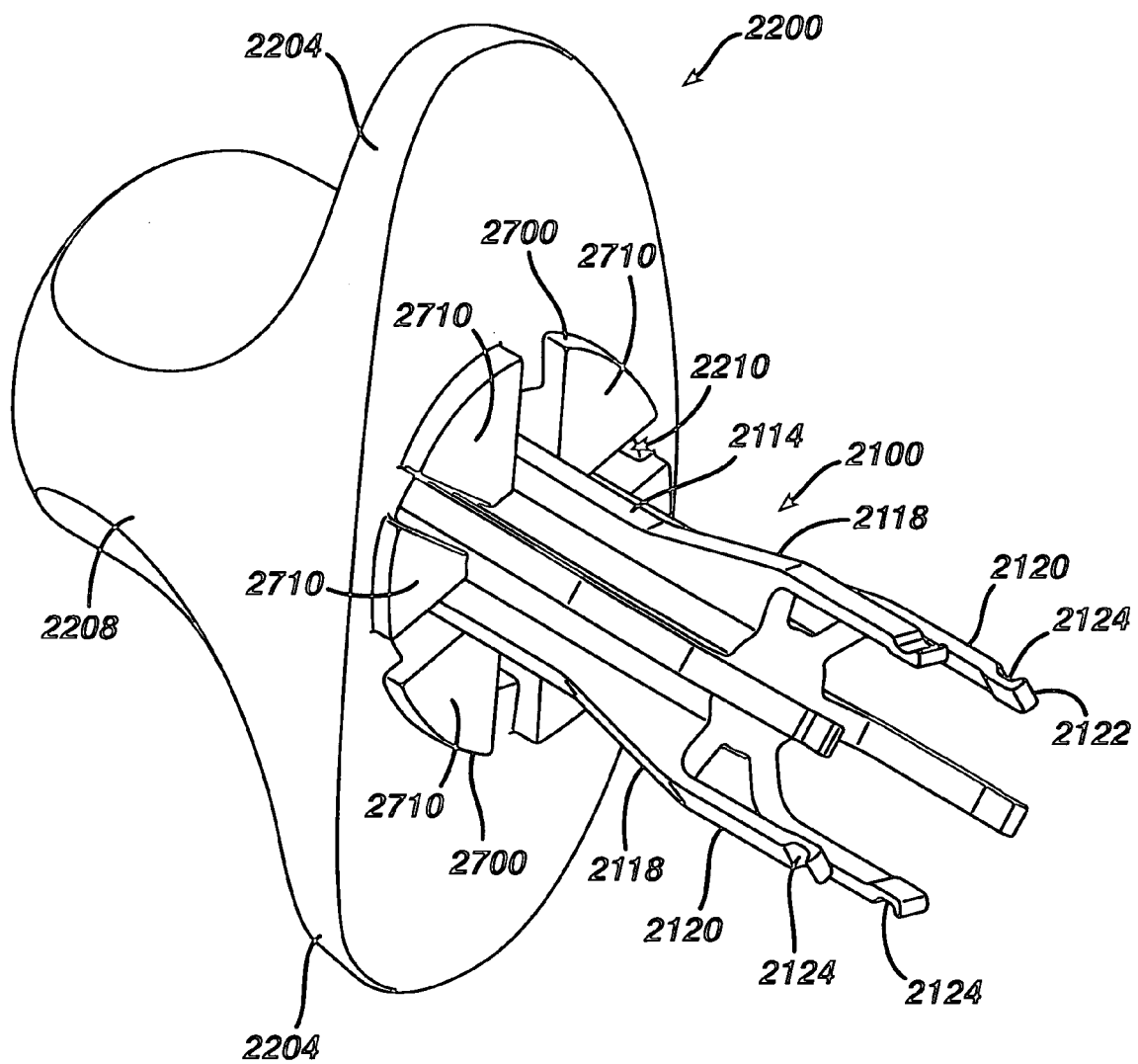
FIG. 40A is a schematic illustration showing the proximal face a handle and showing an endcap loading element extending into a central bore in the handle.

Each prong 2120 can have a slot 2124 formed in the outwardly facing surface, as shown in FIG. 38A and FIG. 40A. Together, the slots 2124 in the prongs 2120 provide a circumferentially interrupted groove in which an expandable ring, such as a silicone O-ring or Teflon O-ring 2160 can be seated. The radial thickness 2123 of the prongs 2120 illustrated in FIG. 38A can be sized to take into account various factors, such as the inner diameter and material of the endcap, the outer diameter of the distal end of the endoscope 1000, and the number of prongs 2120 on nose cone 2100, such that when prongs 2120 are disposed between the outer surface of the distal end of the endoscope, and the inner surface of the endcap, the radially inner surface of the endcap is spaced from the outer surface of the endoscope. One suitable thickness 2123 when six prongs 2120 are employed is about 0.032 inch.

Prior to seating the O-ring 2160 in the slots 2124, the distal end of the endoscope 1000 can be inserted between the prongs 2120. The O-ring 2160 can then be slid over body 2110 of nose cone 2100 and up over the rounded prong shoulders 2118. The O-ring can be stretched over the shoulders 2118 and be seated in the slots 2124 in prongs 2120. The O-ring can thereby provide a radially inward compressive force on the prongs 2120, urging the radially inwardly facing surfaces of the prongs 2120 into engagement with the outer surface of the distal end of the endoscope 1000.

Figure 39:
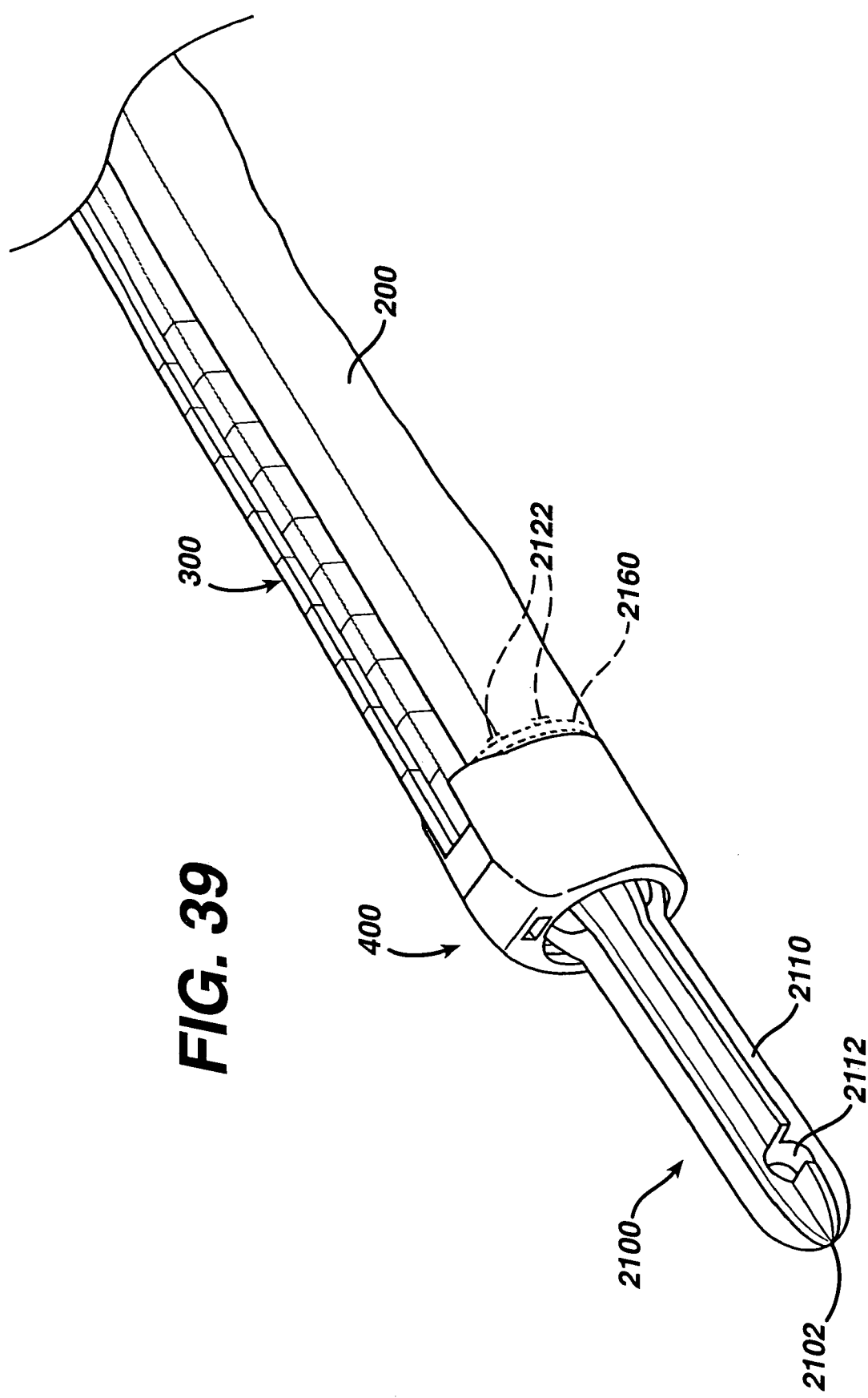
FIG. 39 illustrates the endcap loading element disposed on the distal end of the endoscope, and the endoscope disposed in the sheath, with the flexible prongs of the endcap loading element disposed within the sheath and engaging an outer surface of the endoscope, with an O-ring compressing the flexible prongs and positioned against the proximal face of the endcap, and with a distal portion of the endcap loading element extending through the bore of the endcap.

With the nose cone 2100 positioned on the distal end of the endoscope 1000 the endoscope 1000 is loaded onto the sheath assembly (comprising the handle 100, sheath 200, track 300, and endcap 400). The endoscope is loaded onto the sheath assembly such that the body portion 2110 of nose cone 2100 extends distally from the endcap 400, as shown in FIG. 39, and such that the proximal face of the endcap 400 abuts against prong shoulders. The O-ring 2160 and two proximal prong ends 2122 are shown in phantom in FIG. 39, as the O-ring and prong ends would be inside the sheath (but can be visible when sheath 200 is made of a substantially transparent film material).

Referring now to FIG. 40 and FIG. 40A, a handle 2200 is shown with a pair of outwardling extending arms 2204 extending from a central hub 2208. The hub 2208 includes a grooved through bore 2210. The through bore 2210 has grooves sized and shaped to permit the handle 2200 to slide longitudinally along the splines 2114 of body portion 2110 on nose cone 2100. The engagement of the splines 2114 with the grooved bore 2210 prevents rotation of the handle 2200 with respect to the nose cone 2100 and the endcap 400. While rotation of the handle 2200 with respect to the nose cone 2100 could be permitted in an alternative embodiment that does not employ splines and grooves, it can be advantageous to prevent rotation of the handle 2200 with respect to the nose cone 2100. For instance, it may be desirable to load the endcap 400 and track 300 onto the endoscope in such a way to maintain a desired o'clock orientation of the track 300 with respect to features such as optics and/or working channels in the distal end of the endoscope. Maintaining the handle 2200 rotationally fixed with respect to the nose cone 2100 can aid in avoiding angular misalignment of the track 300 with respect to the distal end of the endoscope 1000.

FIG. 40A illustrates the nose cone 2100 extending into the bore 2210 from the proximal side of the handle 2200. The proximal side of handle 2200 can include one or more surfaces for providing a pressing force against distal surface 412 of endcap 400. In FIG. 40A, the handle 2200 is shown having multiple generally wedge shaped extensions 2700 extending proximally from handle 2200. In FIG. 40A, six extensions 2700 are provided, one for each groove in the through bore 2210. The extensions 2700 can be separated by a distance substantially equal to the width of the grooves in the through bore 2210. The extensions 2700 each have a proximally facing surface 2710. Together, the surfaces 2710 can engage the distal surface 412 of endcap 400 as handle 2200 is advanced proximally along nose cone 2100. Providing separate, spaced apart surfaces 2710 can be beneficial in preventing the material of endcap 400 from being pinched between the nose cone 2100 and the handle 2200 as the handle 2200 provides a pushing force against endcap 400 and prongs 2120 provide a pulling force on the distal end of the endoscope.

Referring to FIG. 41, a pull ring 2300 is shown attached to a distal end of the nose cone 2100, such as with a pin 2308 which extends through a pull ring collar 2304 and into through bore 2112 in nose cone 2100. The combination of the pull ring 2300 mounted on the distal end of the nose cone 2100 and the handle 2200 slidably supported on the nose cone 2100 via the spline and groove arrangement permits a user to provide a distal pulling (tensile) force on the endoscope 1000 through the endcap 400 via the nose cone 2100, while at the same time exerting a proximal pushing (compressive) force on the distal face of the endcap 400 via the surfaces 2710 of handle 2200.

Referring to FIG. 42, the application of such forces is illustrated schematically by arrows 2250 and 2350. By pulling on the pull ring 2300 in the direction indicated by arrow 2350 while pushing on the handle 2200 in the direction indicated by arrows 2250, the endcap 400 is pushed onto the distal end of the endoscope 1000 and the O-ring is forced off the prongs 2120, such that the prongs 2120 can disengage from the distal end of the endoscope 1000 and be pulled through the through bore 420 of the endcap 400. O-ring 2160 can remain positioned about the endoscope proximal of the endcap 400.

In the installation embodiment shown in FIGS. 38-42, a distal pulling force is applied to the outside surface of the endoscope 1000 with flexible prongs 2120 as a proximal pushing force is provided by handle 2200 against the distal face of the endcap 400. FIGS. 43-47 illustrate an alternative apparatus and method for use in positioning an endcap on an endoscope, which can be employed to provide a pulling force at an internal surface of an endoscope, such as an internal surface of a working channel of an endoscope, as a pushing force is applied to the endcap. The sheath and track are omitted from the Figures for clarity, with it being understood that the apparatus and method illustrated in FIGS. 43-47 can be used to position an endcap on the distal end of an endoscope, including in applications where a sheath and/or track is not employed.

Figure 43:
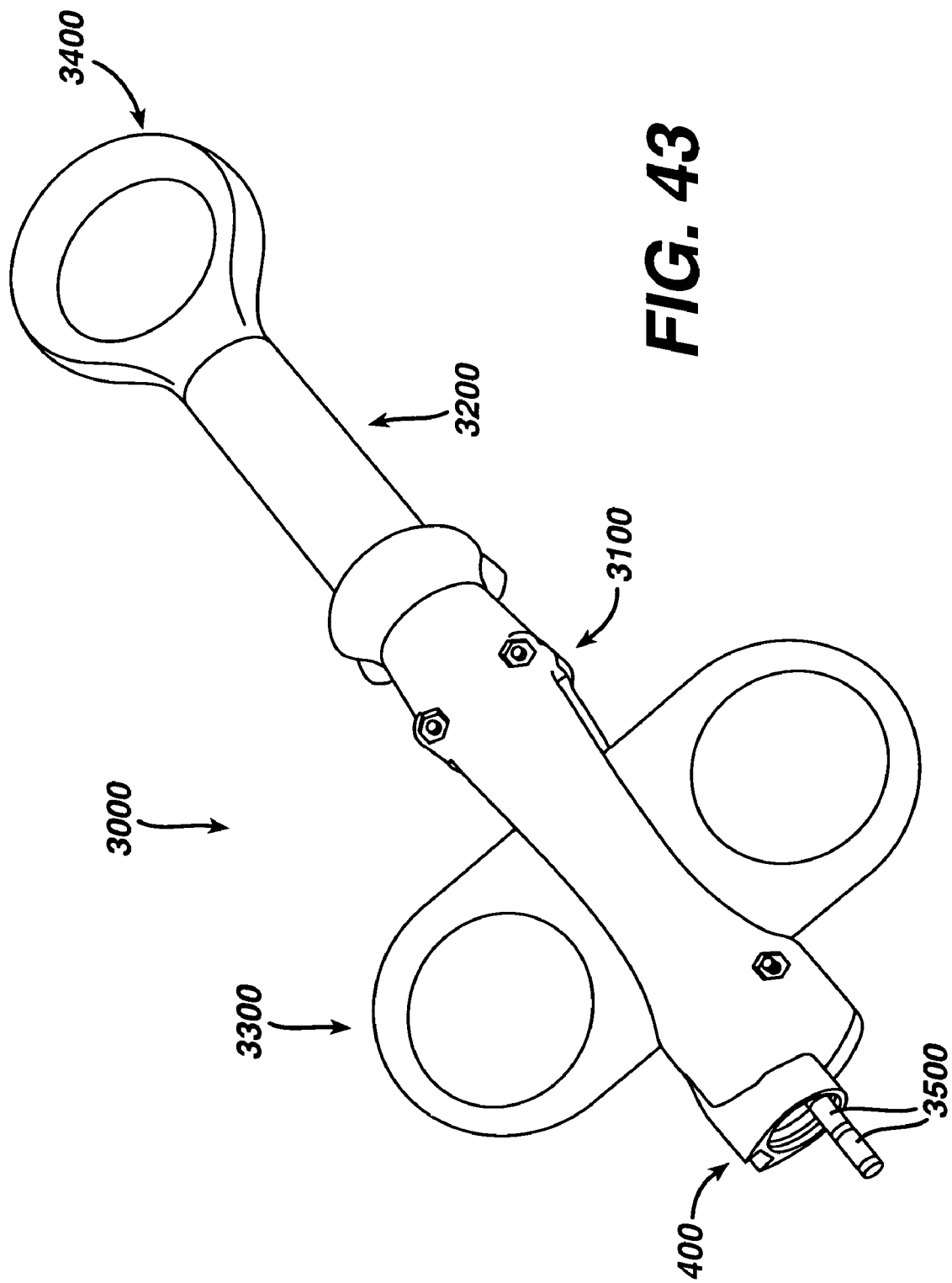
FIG. 43 illustrates a schematic isometric view of an apparatus that engages an internal surface of an endoscope and can be used to push an endcap onto an endoscope.
Figure 44:
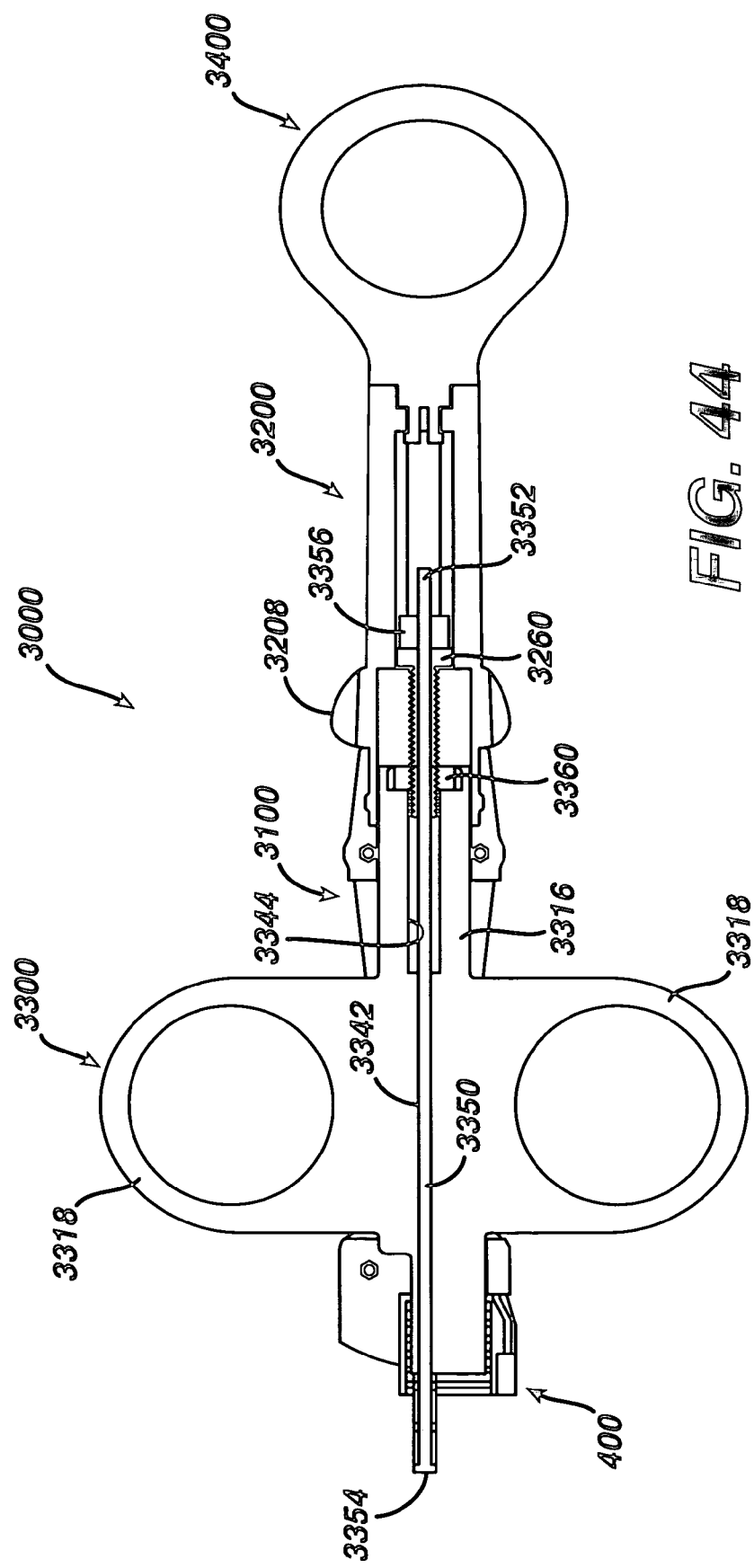
FIG. 44 is cross-sectional, schematic illustration of the apparatus of FIG. 43.
Figure 45:
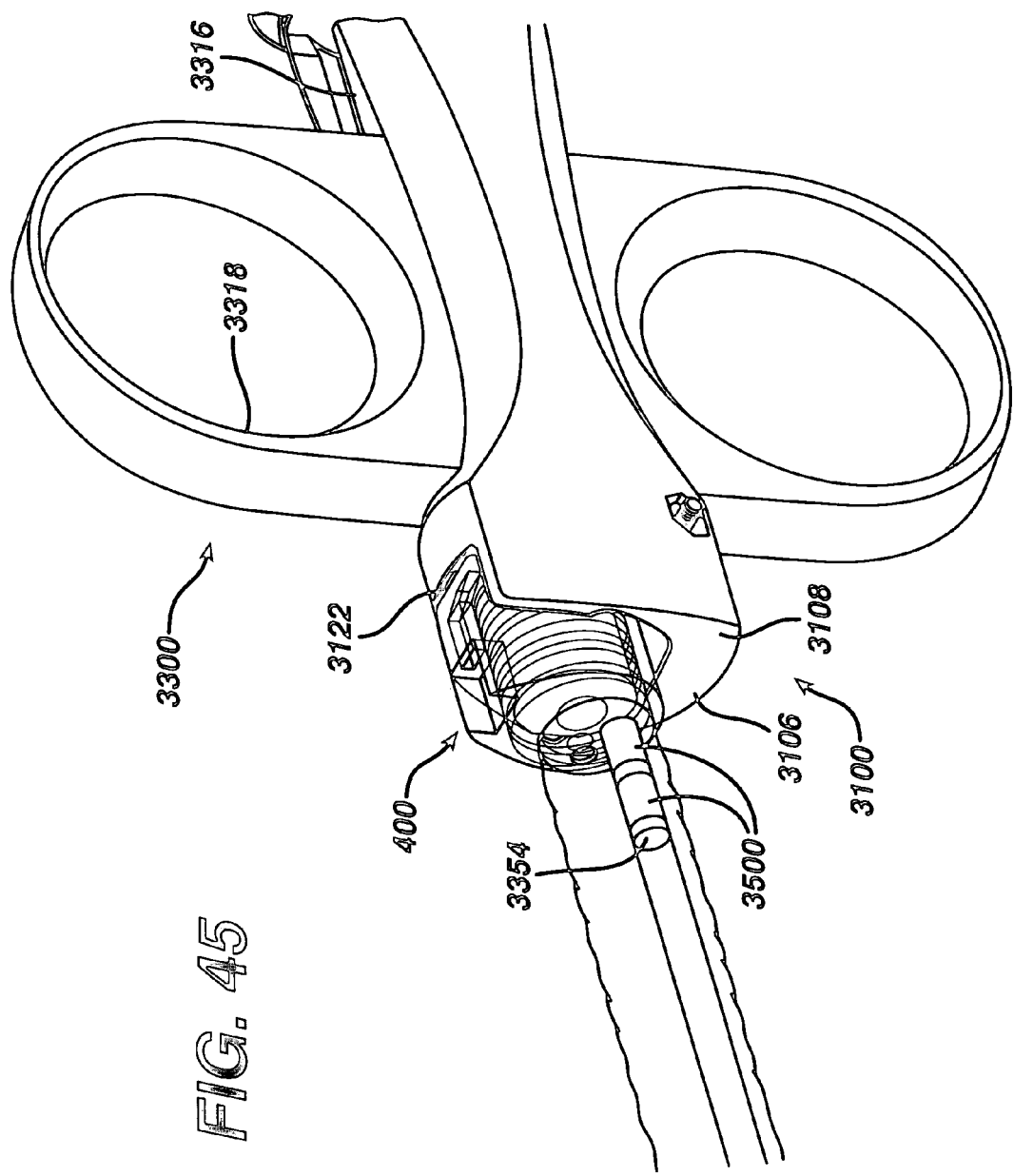
FIG. 45 is a schematic isometric illustration showing the distal end of an endoscope, the endcap, and the forward portion of the apparatus of FIG. 43 with a portion of the apparatus being inserted into a working channel of the endoscope.
Figure 46:
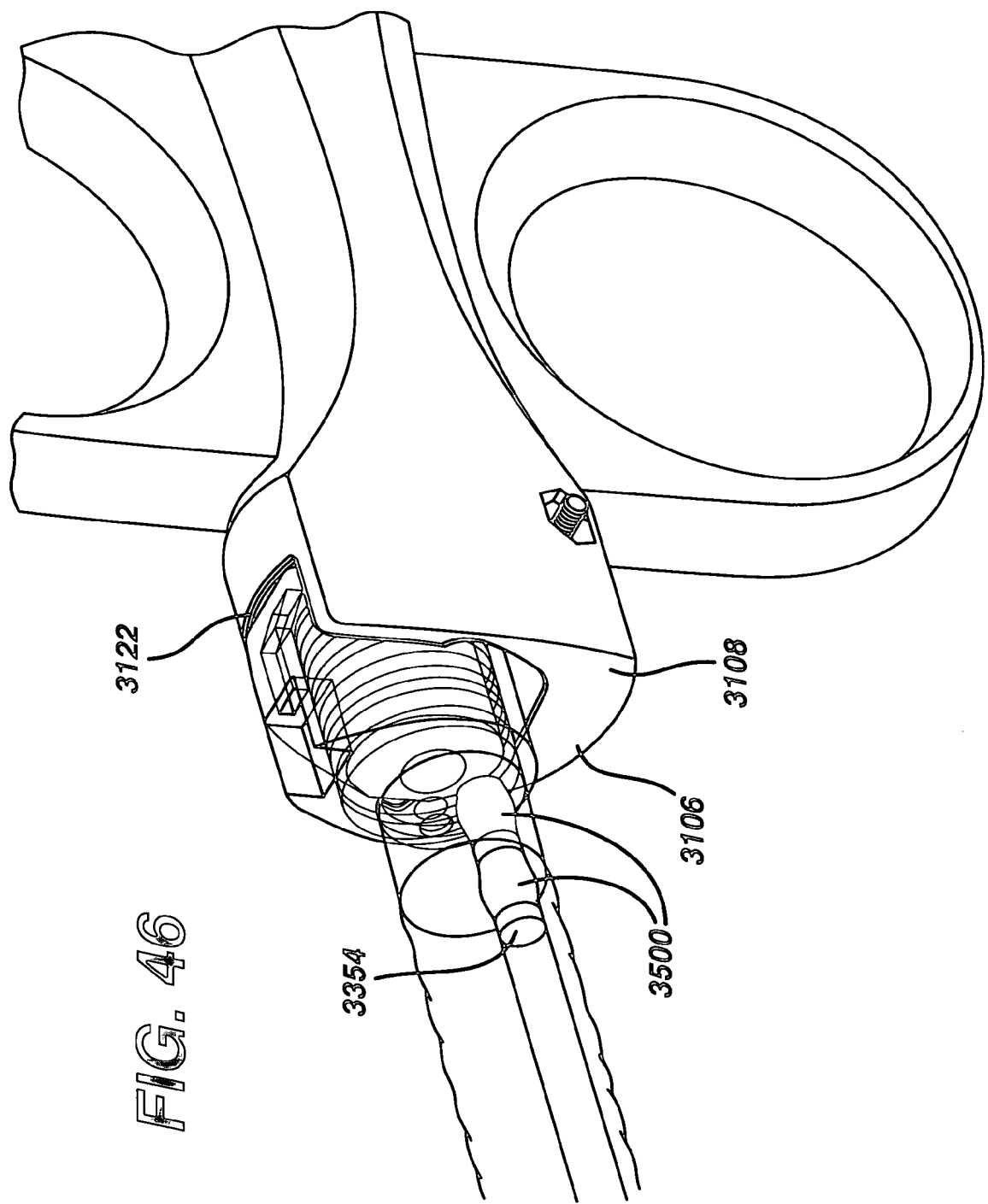
FIG. 46 is a schematic isometric illustration showing expansion of a portion of the apparatus inserted into the working channel of the endoscope.
Figure 47:
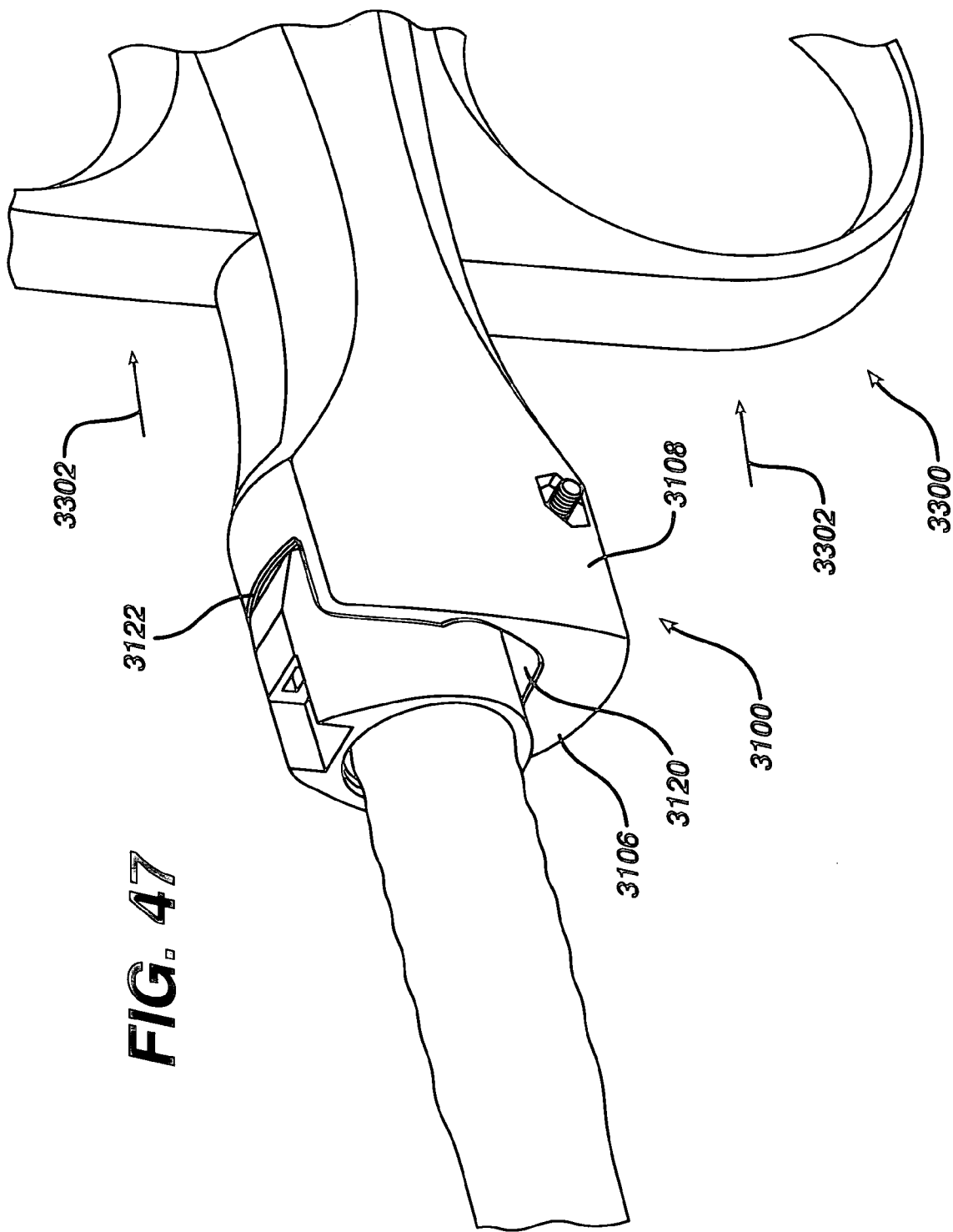
FIG. 47 is a schematic isometric illustration showing rearward movement of an actuator of the apparatus of FIG. 43 to push the endcap onto the endoscope in a first direction while pulling the endoscope in the opposite direction.

FIG. 43 is a schematic isometric view of the loading apparatus 3000, and FIG. 44 is a partial cross-sectional illustration of the apparatus 3000. In FIGS. 43 and 44, the endcap 400 is shown for illustration purposes, with it being understood that the endcap 400 is not part of the apparatus 3000. FIGS. 45, 46, and 47 illustrate steps in employing the apparatus 3000 to load an endcap 400 on and endoscope, with the endoscope and endcap being illustrated to be generally transparent for purposes of illustration and clarity (though endcap 400 and endoscope could be formed of generally transparent materials if desired).

Apparatus 3000 includes a body section 3100, a rotation section 3200, and translating section 3300, and a ring 3400. As shown in FIGS. 45 and 46, the apparatus 3000 can include one or more expandable members, such as resilient cylinders 3500, which can engage an internal surface of the endoscope, such as by being positioned within a working channel of the endoscope. Cylinders 3500 can be formed of any suitable material, such as rubber or synthetic elastomeric materials, which expands radially when compressed axially. Alternatively, other types of expandable members could be employed, such as members which expand by inflation.

Referring to FIG. 46, the cylinders 3500 can be expanded to engage the inside surface of the working channel. Expansion of the rubber cylinders can be provided, in part, in connection with the rotation of rotation section 3200, as described more fully below.

Referring to FIG. 47, with the cylinders 3500 expanded within the working channel of the endoscope to compressively engage the radially inner surface of the working channel, the translating section 3300 can be drawn distally relative to body section 3100 (as indicated by arrows 3302 in FIG. 47). As shown in the Figures, body section 3100 can include a recess 3120 having a proximally facing surface 3122 for engaging the distal surface 412 of endcap 400. As translating section 3300 is drawn distally relative to body section 3100, the cylinders 3500 can be retracted distally relative to body section 3100. Accordingly, the combination of the pulling force provided on the endoscope by the cylinders 3500 being pulled distally while engaging the inside surface of the working channel, and the complementary reactive pushing force exerted on the distal surface 412 of endcap 400 by surface 3122, serves to press the endcap 400 onto the distal end of the endoscope. Accordingly, the apparatus 3000 can be used to install the endcap 400 on the distal end of the endoscope without holding or otherwise contacting the exterior surface of the endoscope or the sheath (if a sheath is employed).

The components and operation of the apparatus 3000 will now be described in more detail with reference to FIGS. 43-47, as well as cross-sectional illustrations 48 and 49. Body portion 3100 can include an outer surface provided by two body halves 3106 and 3108. Body halves can be joined together in any suitable manner, such as with screw type fasteners, rivets, with adhesive, and the like.

The translating section 3300 can be disposed at least partially within the body portion 3100, and can include a hub 3316 and outwardly extending ring grips 3318. The ring grips 3318 can extend outwardly from hub 3316 through slots provided between body portion shell halves 3106 and 3108.

Figure 48:
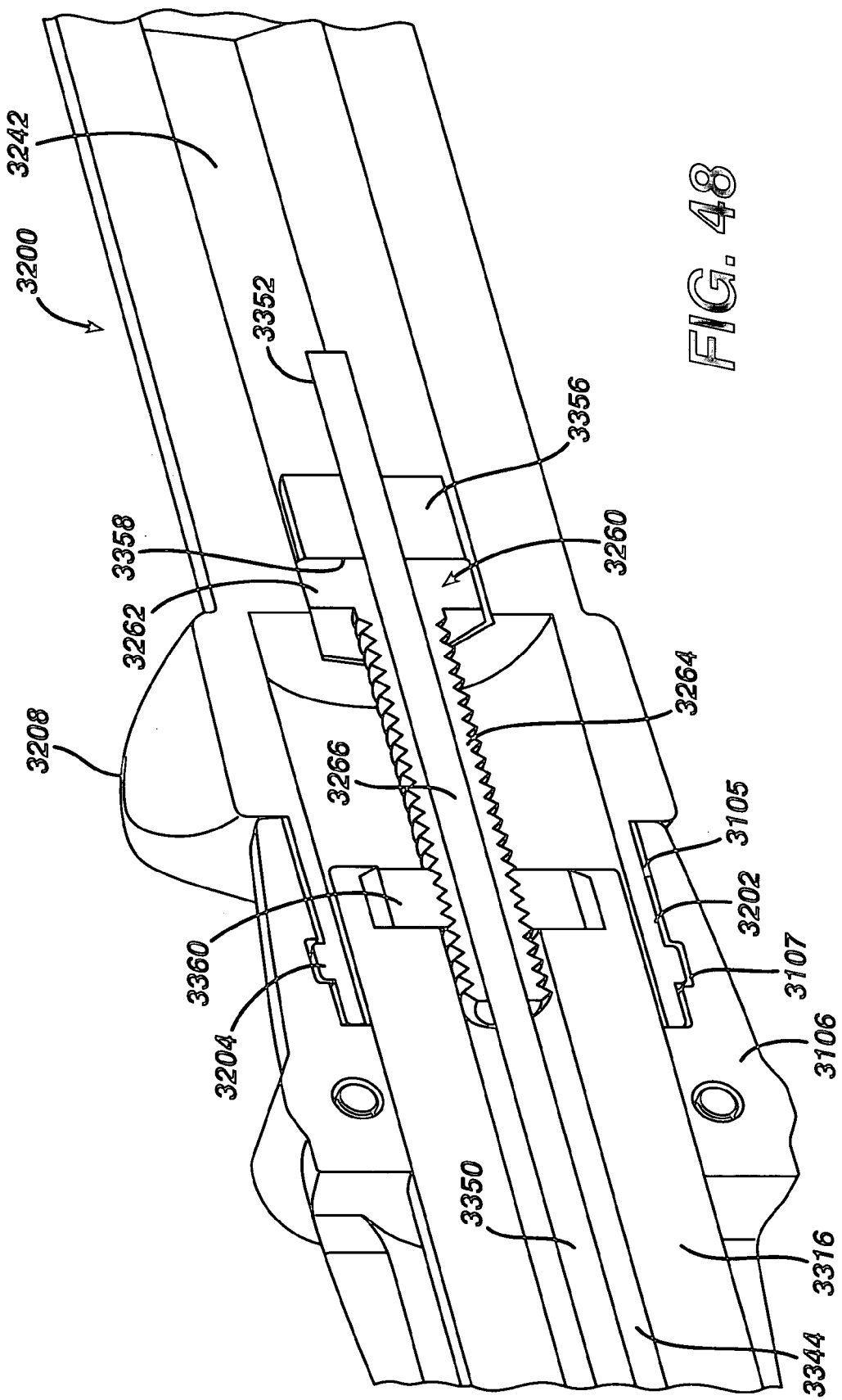
FIG. 48 is a cross-sectional, schematic illustration of a portion of the apparatus of FIG. 43.

Referring to FIG. 44 and FIG. 48, rotating section 3200 can be supported at an end of body portion 3100 such that rotating section 3200 is rotatable with respect to body portion 3100 and such that rotating section is rotatable with respect to translating section 3100. As shown in FIG. 48, rotating section 3200 can have end 3202 received within a recess 3105 provided by body halves 3106 and 3108. End 3202 can include a ring 3204 formed on an outer surface of end 3202. The ring 3204 is received in a groove 3107, which can be formed on an inside surfaces of body halves 3106 and 3108. The mating of ring 3204 in groove 3107 permits section 3200 to rotate with respect to body section 3100, while preventing translation of section 3200 with respect to body section 3100.

Rotating section 3200 can include a collar 3208 which can be gripped by fingers to rotate section 3200. Ring 3400 can be supported at an end of rotating section 3200 such that Ring 3400 can rotate freely about the longitudinal axis of the rotating section 3200 independently of the position of rotating section 3200. Accordingly, the ring 3400 can be aligned to have the same planar orientation as that of ring grips 3318 on translating section 3300, regardless of how rotating section 3200 is rotated.

Figure 49:
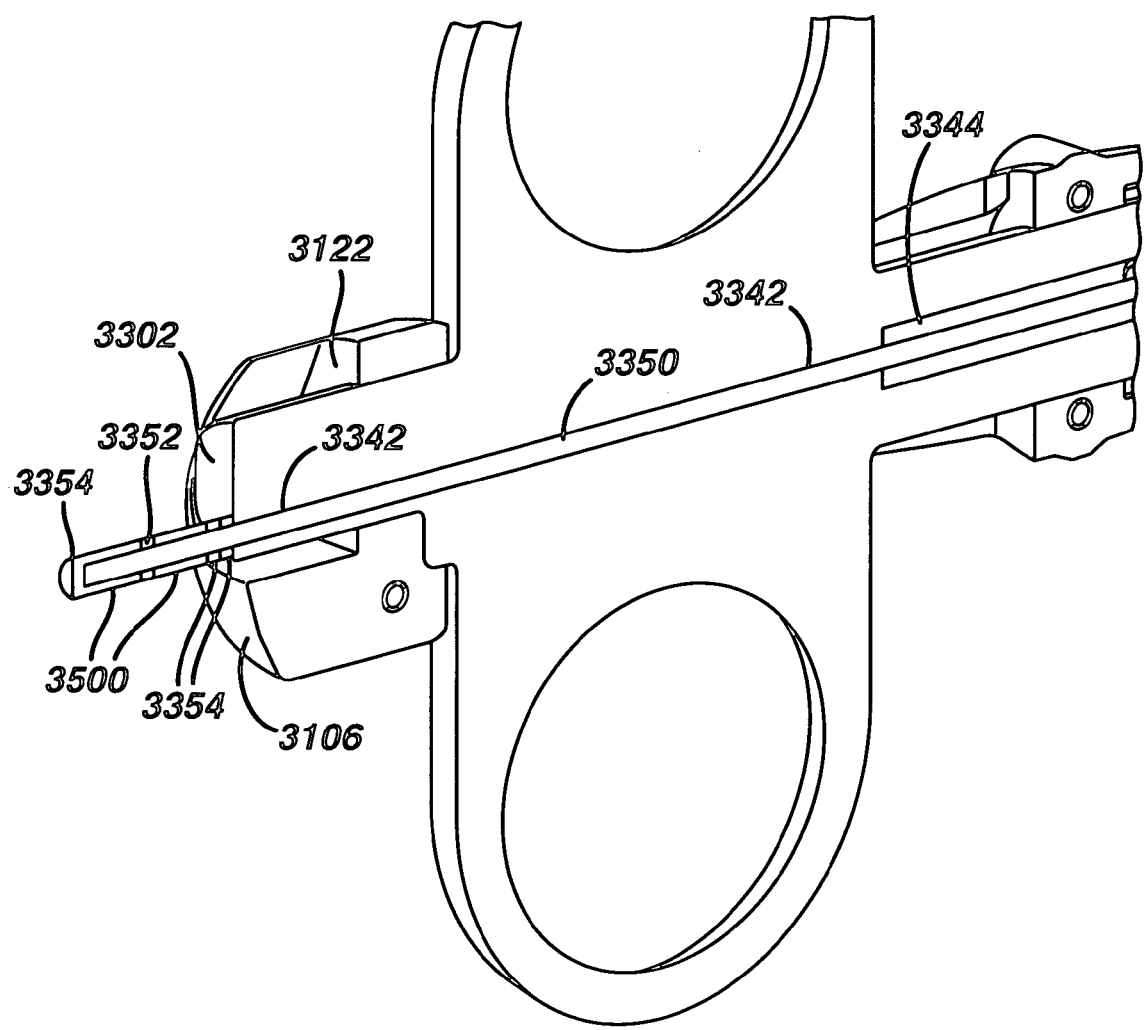
FIG. 49 is a cross-sectional, schematic illustration of a portion of the apparatus of FIG. 43.

FIG. 48 provides an enlarged schematic cross-sectional illustration of portions of the translating section 3300 and the rotating section 3200, and FIG. 49 provides an enlarged schematic cross-sectional illustration of portions of the apparatus which are employed to engage the endcap or endoscope. The translating section 3300 can have a central bore 3342 extending the length of the translating section. The central bore 3342 is shown including an enlarged bore section 3344 extending along the length of hub 3316. A shaft 3350 extends through central bore 3342, and sized with respect to bore 3342 and supported in bore 3342 to rotate freely within bore 3342. The shaft 3350 can extend from a first end 3352, to a second end 3354. Second end 3354 can have an enlarged diameter relative to the remaining length of the shaft 3350, so that the second end 3354 can be employed to compress the cylinders 3350.

Referring to FIG. 48, an internally threaded member 3360 is disposed at an end of the hub 3316. The internally threaded member 3360 can be in the form of a nut having an internally threaded through hole that is generally coaxially aligned with respect to central bore 3342 and enlarged bore section 3344. The internally threaded member 3360 is fixed with respect to translating section 3300.

Rotating section 3200 can include a longitudinally extending internal channel 3242 which is generally coaxially aligned with respect to bore 3342. An externally threaded member 3260 is disposed to slide in bore 3242. The member 3260 can be in the form of a screw having a non-circular head 3262, a longitudinally extended external threaded portion 3264, and a longitudinally extending through bore 3266. Through bore 3266 extends the length of the screw 3260, and can have an internal diameter sized to receive shaft 3350 therethrough. Through bore 3266 can be sized such that shaft 3350 may rotate freely with respect to screw 3260.

The head 3262 of screw 3260 can have the shape of a regular polygon. Bore 3242 in rotating section 3200 can have a non-circular cross-sectional shape similar to that of the head 3262 (e.g. hexagonal cross-section if head 3262 is hexagonal), so that screw 3260 can translate in bore 3242 relative to rotating section 3200, but such that screw 3260 is constrained to rotate with rotating section 3200. Alternatively, screw 3260 could have a head 3262 which includes a key or other feature for permitting sliding translation of screw 3260 within the bore 3242, while ensuring that screw rotates with rotating section 3200.

A shaft collar 3356 is disposed at or near shaft end 3352 of shaft 3350. Shaft collar 3356 can be fixed to shaft 3350, such as with a set screw, pin, adhesive, or any other suitable fastening means for fixing collar 3356 on shaft 3350. Collar 3356 can be disposed in bore 3242, and has an outer diameter sized to permit collar 3356 to freely translate and rotate with respect to rotating section 3200. A surface 3358 of collar 3356 can abut or otherwise engage an end surface of screw head 3262, as shown in FIG. 48.

Referring to FIG. 49, cylinders 3500 can be supported on a portion of the shaft 3350 which extends from bore 3342.

Cylinders 3500 can be supported on a portion of the shaft 3350 which extends outwardly from an end face 3302 of translating section 3300. One cylinder 3500 can be disposed on shaft 3350 between shaft end 3354 and a spacer 3352. Spacer 3352 is formed of a material which is relatively harder and less resilient than cylinders 3500, and spacer 3352 can be in the form of a metallic washer. The second cylinder 3500 can be disposed on shaft 3350 between spacer 3352 and a pair of spacers 3354. Spacers 3354 can be disposed on shaft 3350 between the second cylinder 3500 and end face 3302, as shown in FIG. 49.

To employ the apparatus 3000 to load an endcap onto an endoscope, the apparatus 3000 is positioned with respect to the endcap and endoscope as shown in FIG. 45, with the translating section 3300 in a forward position with respect to the body section 3100, with shaft end 3350 and cylinders 3500 disposed in the working channel of the endoscope; with the endface 3302 of translating section 3300 against the distal end face of the endoscope, and with surface 3122 of body section 3100 against the distal face of the endcap. Rotating section 3200 is then rotated (such as via collar 3208), which rotation causes screw 3260 to rotate within nut 3360. As screw 3260 rotates, screw 3260 translates in a rearward direction in bore 3242, in accordance with the pitch of the threads on screw 3260. Rearward movement of screw 3260 pushes shaft collar 3356 rearward, which in turn causes the shaft 3350 and shaft end 3354 to move rearward relative to the translation section 3100, thereby compressing the cylinders 3500 and causing the cylinders to expand radially and compressively engage the inside surface of the working channel of the endoscope.

Then, with the cylinders 3500 expanded in the working channel of the endoscope, the thumb can be inserted in ring 3400 and two fingers can be inserted in ring grips 3318. The fingers in ring grips 3318 can exert a rearward force on translating section 3300 such that section 3300 is drawn rearward with respect to body section 3100. Drawing the translating section 3300 rearward as shown in FIG. 47 (in the direction of arrows 3302) also results in the shaft 3350 and cylinders 3500 moving rearward. Because the shaft 3350 and cylinders 3500 move rearward together with translating section 3300, the cylinders are not expanded further. The rearward force on shaft 3350 (tensile force in shaft 3350) and cylinders 3500 (which engage the internal surface of the endoscope) exerts a rearward force on the endoscope (pulling force on endoscope), while surface 3122 on body section 3100 pushes on the distal face of the endcap. Accordingly, as the section 3300 is drawn rearward with respect to body section 3100, a pulling force is exerted on an inner surface of the endoscope, while a pushing force is exerted on a distal face of the endcap, thereby urging the endcap onto the distal end of the endoscope.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to deployment of a feeding tube through the mouth and esophagus, but it will be understood the present invention has applicability to other portions of the body, and for instance, could be used to direct medical accessories into the body through other openings, including other naturally occurring openings in the body. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended claims.

What is claimed:

1. An apparatus for positioning a device on an end of an endoscope, the apparatus comprising:
   a first component for applying a proximally directed axial force to the device, wherein the first component is configured to releasably engage the device; and
   a second component operatively associated with the first component and movable with respect to the first component, wherein the second component is configured to releasably engage the endoscope, wherein the second component is adapted to apply a force to an outer surface of the endoscope, and wherein the second component is adapted to apply a distally directed axial force to the endoscope through an opening in the device.

2. The apparatus of claim 1 wherein the first component is adapted to apply a force to the device simultaneously with the second component applying the force to the endoscope.

3. The apparatus of claim 1 wherein the first component is adapted to apply a pushing force to the device, and wherein the second component is operatively associated with the first component to apply a pulling force to the endoscope simultaneously with the application of the pushing force.

\* \* \* \* \*